(12) United States Patent
Dickinson et al.

(10) Patent No.: US 8,741,630 B2
(45) Date of Patent: Jun. 3, 2014

(54) METHODS OF DETECTING TARGETS ON AN ARRAY

(75) Inventors: Todd Dickinson, San Diego, CA (US); Kenneth D. Coblentz, San Diego, CA (US); Edward Carlson, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 362 days.

(21) Appl. No.: 12/971,996

(22) Filed: Dec. 17, 2010

(65) Prior Publication Data

US 2011/0092389 A1 Apr. 21, 2011

Related U.S. Application Data

(63) Continuation of application No. 10/856,039, filed on May 27, 2004, now abandoned, which is a continuation of application No. 09/931,271, filed on Aug. 16, 2001, now Pat. No. 6,770,441, which is a continuation-in-part of application No. 09/782,588, filed on Feb. 12, 2001, now abandoned.

(60) Provisional application No. 60/181,631, filed on Feb. 10, 2000.

(51) Int. Cl.
*C12M 1/34* (2006.01)
*C12Q 1/68* (2006.01)
*G01N 15/06* (2006.01)

(52) U.S. Cl.
USPC ......... 435/287.2; 422/68.1; 435/6.1; 435/7.1; 435/283.1; 435/287.8; 435/288.2

(58) Field of Classification Search
None
See application file for complete search history.

(56) References Cited

U.S. PATENT DOCUMENTS

| | | | |
|---|---|---|---|
| 4,200,110 A | 4/1980 | Peterson et al. | |
| 4,349,510 A | 9/1982 | Kohlemainen et al. | |
| 4,499,052 A | 2/1985 | Fulwyler | |
| 4,682,895 A | 7/1987 | Costello | |
| 4,785,814 A | 11/1988 | Kane | |
| 4,812,216 A * | 3/1989 | Hurd et al. | 204/464 |
| 4,822,746 A | 4/1989 | Walt | |
| 4,824,789 A | 4/1989 | Yafuso et al. | |
| 4,879,097 A | 11/1989 | Whitehead et al. | |
| 4,971,903 A | 11/1990 | Hyman | |
| 4,999,306 A | 3/1991 | Yafuso et al. | |
| 5,002,867 A | 3/1991 | Macevicz | |
| 5,028,545 A | 7/1991 | Soini | |
| 5,100,775 A | 3/1992 | Smyczek et al. | |
| 5,105,305 A | 4/1992 | Betzig et al. | |
| 5,114,864 A | 5/1992 | Walt | |
| 5,132,242 A | 7/1992 | Cheung | |
| 5,143,853 A | 9/1992 | Walt | |
| 5,194,300 A | 3/1993 | Cheung | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,281,540 A | 1/1994 | Merkh et al. | |
| 5,288,514 A | 2/1994 | Ellman | |
| 5,298,741 A | 3/1994 | Walt et al. | |
| 5,302,509 A | 4/1994 | Cheeseman | |
| 5,314,829 A | 5/1994 | Coles | |
| 5,320,808 A | 6/1994 | Holen et al. | |
| 5,320,814 A | 6/1994 | Walt et al. | |
| 5,357,590 A | 10/1994 | Auracher | |
| 5,380,489 A | 1/1995 | Sutton et al. | |
| 5,435,724 A | 7/1995 | Goodman et al. | |
| 5,445,934 A | 8/1995 | Fodor et al. | |
| 5,466,319 A | 11/1995 | Zager et al. | |
| 5,474,895 A | 12/1995 | Ishii et al. | |
| 5,481,629 A | 1/1996 | Tabuchi | |
| 5,494,798 A | 2/1996 | Gerdt et al. | |
| 5,494,810 A | 2/1996 | Barany et al. | |
| 5,496,997 A | 3/1996 | Pope | |
| 5,512,490 A | 4/1996 | Walt et al. | |
| 5,516,635 A | 5/1996 | Ekins et al. | |
| 5,518,883 A | 5/1996 | Soini | |
| 5,534,424 A | 7/1996 | Uhlen et al. | |
| 5,545,531 A | 8/1996 | Rava et al. | |
| 5,565,324 A | 10/1996 | Still et al. | |
| 5,573,909 A | 11/1996 | Singer et al. | |
| 5,575,849 A | 11/1996 | Honda et al. | |
| 5,578,832 A | 11/1996 | Trulson et al. | |
| 5,633,972 A | 5/1997 | Walt et al. | |

(Continued)

FOREIGN PATENT DOCUMENTS

| | | |
|---|---|---|
| EP | 0 392 546 | 10/1990 |
| EP | 0 478 319 | 4/1992 |
| EP | 0 723 146 | 7/1996 |
| EP | 0 269 764 | 6/1998 |
| GB | 2349349 | 11/2000 |
| WO | WO 89/11101 | 11/1989 |
| WO | WO 91/06678 | 5/1991 |
| WO | WO 93/02360 | 2/1993 |
| WO | WO 93/21340 | 10/1993 |
| WO | WO 93/22058 | 11/1993 |
| WO | WO 93/23564 | 11/1993 |

(Continued)

OTHER PUBLICATIONS

Abel et al., "Fiber-optic evanescent wave biosensor for the detection of oligonucleotides," Anal Chem. (1996) 68(17):2905-2912.

(Continued)

*Primary Examiner* — Sarae Bausch
(74) *Attorney, Agent, or Firm* — Knobbe, Martens, Olson & Bear LLP

(57) ABSTRACT

The invention relates to methods of detecting a target analyte in a biological sample using composite microsphere arrays having first and second assay locations. Preferred target analytes include nucleic acid, and more specifically, nucleic acid having one or more single nucleotide polymorphisms (SNPs).

29 Claims, 18 Drawing Sheets

(56) References Cited

U.S. PATENT DOCUMENTS

| | | | |
|---|---|---|---|
| 5,639,603 A | 6/1997 | Dower et al. | |
| 5,649,576 A | 7/1997 | Kirk et al. | |
| 5,649,924 A | 7/1997 | Everett et al. | |
| 5,656,241 A | 8/1997 | Seifert et al. | |
| 5,679,524 A | 10/1997 | Nikiforov et al. | |
| 5,690,894 A | 11/1997 | Pinkel et al. | |
| 5,733,729 A | 3/1998 | Lipshutz et al. | |
| 5,744,305 A | 4/1998 | Fodor et al. | |
| 5,795,716 A | 8/1998 | Chee et al. | |
| 5,800,992 A | 9/1998 | Fodor et al. | |
| 5,807,522 A | 9/1998 | Brown et al. | |
| 5,814,524 A | 9/1998 | Walt et al. | |
| 5,830,663 A | 11/1998 | Embleton et al. | |
| 5,830,711 A | 11/1998 | Barany et al. | |
| 5,834,758 A | 11/1998 | Trulson et al. | |
| 5,840,256 A | 11/1998 | Demers et al. | |
| 5,843,767 A | 12/1998 | Beattie | |
| 5,854,684 A | 12/1998 | Stabile et al. | |
| 5,856,083 A | 1/1999 | Chelsky et al. | |
| 5,858,732 A | 1/1999 | Solomon et al. | |
| 5,863,708 A | 1/1999 | Zanzucchi et al. | |
| 5,863,722 A | 1/1999 | Brenner | |
| 5,871,928 A | 2/1999 | Fodor et al. | |
| 5,874,219 A | 2/1999 | Rava et al. | |
| 5,888,723 A | 3/1999 | Sutton et al. | |
| 5,888,834 A | 3/1999 | Ishikawa et al. | |
| 5,900,481 A | 5/1999 | Lough et al. | |
| 5,922,617 A | 7/1999 | Wang et al. | |
| 5,935,793 A | 8/1999 | Wong | |
| 5,974,164 A | 10/1999 | Chee | |
| 6,008,892 A | 12/1999 | Kain et al. | |
| 6,013,456 A | 1/2000 | Akhavan-Tafti | |
| 6,023,540 A | 2/2000 | Walt et al. | |
| 6,025,601 A | 2/2000 | Trulson et al. | |
| 6,027,889 A | 2/2000 | Barany et al. | |
| 6,040,138 A | 3/2000 | Lockhart et al. | |
| 6,051,380 A | 4/2000 | Sosnowski et al. | |
| 6,054,564 A | 4/2000 | Barany et al. | |
| 6,066,454 A | 5/2000 | Lipshutz et al. | |
| 6,083,763 A | 7/2000 | Balch | |
| 6,085,004 A * | 7/2000 | Dower et al. | 385/80 |
| 6,110,678 A | 8/2000 | Weisburg et al. | |
| 6,124,102 A | 9/2000 | Fodor et al. | |
| 6,129,896 A | 10/2000 | Noonan et al. | |
| 6,143,496 A | 11/2000 | Brown et al. | |
| 6,147,205 A | 11/2000 | McGall et al. | |
| 6,172,218 B1 | 1/2001 | Brenner | |
| 6,185,561 B1 | 2/2001 | Balaban et al. | |
| 6,188,783 B1 | 2/2001 | Balaban et al. | |
| 6,191,852 B1 | 2/2001 | Paffhausen et al. | |
| 6,197,506 B1 | 3/2001 | Fodor et al. | |
| 6,198,577 B1 | 3/2001 | Kedar et al. | |
| 6,210,891 B1 | 4/2001 | Nyren et al. | |
| 6,225,625 B1 | 5/2001 | Pirrung et al. | |
| 6,229,911 B1 | 5/2001 | Balaban et al. | |
| 6,232,066 B1 | 5/2001 | Felder et al. | 435/6 |
| 6,248,521 B1 | 6/2001 | Van Ness et al. | |
| 6,251,639 B1 | 6/2001 | Kurn | |
| 6,258,568 B1 | 7/2001 | Nyren | |
| 6,261,523 B1 * | 7/2001 | Schembri | 422/559 |
| 6,261,776 B1 | 7/2001 | Pirrung et al. | |
| 6,268,148 B1 | 7/2001 | Barany et al. | |
| 6,274,320 B1 | 8/2001 | Rothberg et al. | |
| 6,291,183 B1 | 9/2001 | Pirrung et al. | |
| 6,306,643 B1 | 10/2001 | Gentalen et al. | |
| 6,308,170 B1 | 10/2001 | Balaban | |
| 6,309,822 B1 | 10/2001 | Fodor et al. | |
| 6,310,189 B1 | 10/2001 | Fodor et al. | 536/22.1 |
| 6,327,410 B1 * | 12/2001 | Walt et al. | 385/115 |
| 6,340,588 B1 | 1/2002 | Nova et al. | |
| 6,342,349 B1 | 1/2002 | Virtanen | |
| 6,346,413 B1 | 2/2002 | Fodor et al. | |
| 6,355,432 B1 | 3/2002 | Fodor et al. | |
| 6,396,995 B1 | 5/2002 | Stuelpnagel et al. | |
| 6,399,365 B2 | 6/2002 | Besemer et al. | |
| 6,403,320 B1 | 6/2002 | Read et al. | |
| 6,416,952 B1 | 7/2002 | Pirrung et al. | |
| 6,429,027 B1 | 8/2002 | Chee et al. | 436/518 |
| 6,440,677 B2 | 8/2002 | Lipshutz et al. | |
| 6,451,536 B1 | 9/2002 | Fodor et al. | |
| 6,458,533 B1 | 10/2002 | Felder et al. | |
| 6,489,103 B1 | 12/2002 | Griffiths et al. | |
| 6,491,871 B1 | 12/2002 | Fodor et al. | |
| 6,544,732 B1 * | 4/2003 | Chee et al. | 435/6 |
| 6,544,739 B1 | 4/2003 | Fodor et al. | |
| 6,551,817 B2 | 4/2003 | Besemer et al. | |
| 6,555,361 B1 | 4/2003 | Lyman et al. | 435/287.2 |
| 6,576,424 B2 | 6/2003 | Fodor et al. | |
| 6,589,779 B1 | 7/2003 | McDevitt et al. | |
| 6,604,902 B2 | 8/2003 | Norris et al. | |
| 6,610,482 B1 | 8/2003 | Fodor et al. | |
| 6,646,243 B2 | 11/2003 | Pirrung et al. | |
| 6,680,206 B1 * | 1/2004 | McDevitt et al. | 436/172 |
| 6,703,247 B1 | 3/2004 | Chu | |
| 6,770,441 B2 | 8/2004 | Dickinson et al. | 435/6 |
| 6,824,738 B1 * | 11/2004 | Neeper et al. | 422/72 |
| 6,828,100 B1 | 12/2004 | Ronaghi | |
| 6,998,274 B2 | 2/2006 | Chee et al. | 436/518 |
| 7,041,510 B2 | 5/2006 | Seul et al. | |
| 7,612,020 B2 | 11/2009 | Stuelpnagel et al. | |
| 7,803,537 B2 | 9/2010 | Fan et al. | |
| 2001/0053849 A1 | 12/2001 | Kreek et al. | |
| 2002/0132241 A1 | 9/2002 | Fan et al. | |
| 2003/0157499 A1 | 8/2003 | Lundeberg et al. | |
| 2003/0162210 A1 | 8/2003 | Chetverin et al. | |
| 2003/0162217 A1 | 8/2003 | Rothberg et al. | |
| 2004/0137465 A1 | 7/2004 | Kain et al. | |
| 2005/0064460 A1 | 3/2005 | Holliger et al. | |

FOREIGN PATENT DOCUMENTS

| | | |
|---|---|---|
| WO | WO 93/25563 | 12/1993 |
| WO | WO 96/03212 | 2/1996 |
| WO | WO 97/14028 | 4/1997 |
| WO | WO 97/14928 | 4/1997 |
| WO | WO 97/31256 | 8/1997 |
| WO | WO 97/40385 | 10/1997 |
| WO | WO 98/13523 | 4/1998 |
| WO | WO 98/40726 | 9/1998 |
| WO | WO 98/50782 | 11/1998 |
| WO | WO 98/53093 | 11/1998 |
| WO | WO 98/53300 | 11/1998 |
| WO | WO 99/18434 | 4/1999 |
| WO | WO 99/60170 | 11/1999 |
| WO | WO 99/67414 | 12/1999 |
| WO | WO 99/67641 | 12/1999 |
| WO | WO 00/04372 | 1/2000 |
| WO | WO 00/13004 | 3/2000 |
| WO | WO 00/16101 | 3/2000 |
| WO | WO 00/39587 | 7/2000 |
| WO | WO 00/47996 | 8/2000 |
| WO | WO 00/48000 | 8/2000 |
| WO | WO 00/58516 | 10/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 02/00336 | 1/2002 |

OTHER PUBLICATIONS

Anonymous, "Fluorescent microspheres," Techn. Note 19, Bang Laboratories (Fisher, In) (Feb. 1997).

Anonymous, "Microsphere selection guide," Bang Laboratories, (Fisher, In) (Sep. 1998).

Ahmadian et al., "Analysis of the p53 tumor suppressor gene by pyrosequencing," *BioTechniques* (2000) 28(1):140-4, 146-7.

Bangs, "Immunological applications of microspheres," The Latex Course, Bangs Laboratories (Carmel, IN) (Apr. 1996).

Barker et al., "Development and cellular applications of fiber optic nitric oxide sensors based on a gold-adsorbed fluorophore," Anal Chem. (1998) 70(23):4902-4906.

(56) References Cited

OTHER PUBLICATIONS

Barnard et al., "A fibre-optic chemical sensor with discrete sensing sites," Nature (1991) 353:338-340.
Barshop et al., "Luminescent immobilized enzyme test systems for inorganic pyrophosphate: assays using firefly luciferase and nicotinamide-mononucleotide adenylyl transferase or adenosine-5'-triphosphate sulfurylase," *Anal. Biochem.* (1991) 197(1):266-272.
Chen et al., "A microsphere-based assay for multiplexed single nucleotide polymorphism analysis using single base chain extension," Genome Res. (2000) 10(4):549-557.
Cook et al., "A rapid, enzymatic assay for the measurement of inorganic pyrophosphate in animal tissues," *Anal. Biochem.* (1978) 91:557-565.
Czamik, "Illuminating the SNP genomic code," Modern Drug Discovery (1998) 1(2):49-55.
Drake et al., "A New, Convenient Method for the Rapid Analysis of Inorganic Pyrophosphate," *Anal. Biochem.* (1979) 94:117-120.
Drmanac et al., "Sequencing by oligonucleotide hybridization: a promising framework in decoding of the genome project," The First International Conf. on Electrophoresis, Apr. 10-13, 1990 Florida State University.
Drmanac et al., "Prospects for a miniaturized, simplified and frugal human genome project," Scientia Yugoslavica (1990) 16(1-2):97-107.
Drmanac et al., "Sequencing by hybridization (SBH) with oligonucleotide probes as an integral approach for the analysis of complex genomes," Inter. J. of Genome Research (1992) 1(1):59-79.
Drmanac et al., "Sequencing by hybridization," Automated DNA Sequencing and Analysis ed. M. Adams, C. Fields and J. Venter (1994).
Ferguson et al., "A fiber-optic DNA biosensor microarray for the analysis of gene expression," Nat Biotechnol. (1996) 14(13):1681-1684.
Fuh et al., "Single fibre optic fluorescence pH probe," Analyst (1987) 112:1159-1163.
Guillory et al., "Measurement of simultaneous synthesis of inorganic pyrophosphate and adenosine triphosphate," *Anal. Biochem.* (1971) 39:170-180.
Healey et al., "Development of a penicillin biosensor using a single optical imaging fiber," SPIE Proc. (1995) 2388:568-573.
Healey et al., "Improved fiber-optic chemical sensor for penicillin," Anal Chem. (1995) 67(24):4471-4476.
Healey et al., "Fiberoptic DNA sensor array capable of detecting point mutations," Anal Biochem. (1997) 251(2):270-279.
Hirschfeld et al., "Laser-fiber-optic optrode for real time in vivo blood carbon dioxide level monitoring," J. of Lightwave Tech. (1987) LT-5(7):1027-1033.
Iannone et al., "Multiplexed single nucleotide polymorphism genotyping by oligonucleotide ligation and flow cytometry," Cytometry. (2000) 39(2):131-140.
Johnson et al., "An enzyme method for determination of inorganic pyrophosphate and its use as an assay for rna polymerase," *Anal. Biochem.* (1968) 26:137-145.
Jones, "An iterative and regenerative method for DNA sequencing," *Bio Techniques* (1997) 22:938-946.
Justesen et al., "Spectrophotometric pyrophosphate assay of 2',5'-oligoadenylate synthetase," *Anal. Biochem.* (1992) 207(1):90-93.
Karamohamed et al., "Real-time detection and quantification of adenosine triphosphate sulfurylase activity by a bioluminometric approach," *Anal. Biochem.* (1999) 271:81-85.
Kephart et al., "Molecular diagnostics: isolation and analysis of RNA from human blood," Promega Notes (1998) 68:23-28.
Lust et al., "A rapid, enzymatic assay for measurement of inorganic pyrophosphate in biological samples," Clin. Chimica Acta (1976) 66(2):241-249.
Lyamichev et al., "Polymorphism identification and quantitative detection of genomic DNA by invasive cleavage of oligonucleotide probes," Nat Biotechnol. (1999) 17(3):292-296.

Metzker et al., "Termination of DNA synthesis by novel 3'-modified deoxyribonucleoside 5'triphosphates," *Nucl. Acids Res.* (1994) 22(20):4259-4267.
Michael et al., "Fabrication of micro-and nanostructures using optical imaging fibers and their use as chemical sensors," Proc. $3^{rd}$ Intl. Symp. Microstructures and Microfabricated Systems, ed. P.J. Hesketh, et al., v. 95-7, Electrochem. Soc., (1997) 152-157.
Michael et al., "Making sensors out of disarray: optical sensor microarrays," Proc. SPIE (1998) 3270:34-41.
Michael et al., "Randomly ordered addressable high-density optical sensor arrays," Anal Chem. (1998) 70(7):1242-1248.
Mignani et al., "In-vivo biomedical monitoring by fiber-optic systems," J. of Lightwave Tech. (1995) 13(7):1396-1406.
Nyren et al., "Detection of single-base changes using a bioluminometric primer extension assay," *Anal. Biochem.* (1997) 244(2):367-373.
Nyren, "Apyrase immobilized on paramagnetic beads used to improve detection limits in bioluminometric ATP monitoring," J Biolumin Chemilumin (1994) 9(1):29-34.
Nyren et al., "Solid phase DNA minisequencing by an enzymatic luminometric inorganic pyrophosphate detection assay," *Anal. Biochem.* (1993) 208(1):171-175.
Nyren et al., "Enzymatic method for continuous monitoring of inorganic pyrophosphate synthesis," *Anal. Biochem.* (1985) 151:504-509.
Pantano et al., "Ordered nanowell arrays," Chem. Mater. (1996) 8(12):2832-2835.
Peterson et al., "Fiber optic pH probe for physiological use," Anal Chem. (1980) 52(6):864-869.
Peterson et al., "Fiber-optic sensors for biomedical applications," Science. (1984) 224(4645):123-127.
Piunno et al., "Fiber-optic DNA sensor for fluorometric nucleic acid determination," Anal Chem. (1995) 67(15):2635-2643.
Pope, "Fiber optic chemical microsensors employing optically active silica miscrospheres," SPIE (1995) 2388:245-256.
Reeves et al., "Enzymatic assay method for inorganic pyrophosphate," *Anal. Biochem.* (1969) 28: 282-287.
Ronaghi et al., "Analyses of secondary structures in DNA by Pyrosequencing," *Anal. Biochem.* (1999) 267(1): 65-71.
Ronaghi et al., "A sequencing method based on real-time pyrophosphate," *Science* (1998) 281(5375):363, 365.
Ronaghi et al., "Real-time DNA sequencing using detection of prophosphate release," *Anal. Biochem.* (1996) 242(1) 84-89.
Shoemaker et al., "Quantitative phenotypic analysis of yeast deletion mutants using a highly parallel molecular bar-coding strategy," Nat Genet. (1996) 14(4):450-456.
Strachan et al., "A rapid general method for the identification of PCR products using a fibre-optic biosensor and its application to the detection of Listeria," Lett Appl Microbiol. (1995) 21(1):5-9.
Walt, "Fiber-optic sensors for continuous clinical monitoring," Proc. IEEE (1992) 80(6):903-911.
Walt, "Fiber optic imaging sensors," Accounts of Chem. Research (1998) 31(5):267-278.
Definition of "seal," Merriam-Webster online Dictionary, www.meriam-webster.com, pp. 1-2.
Office Action from U.S. Appl. No. 09/782,588 dated Mar. 16, 2005.
Office Action from U.S. Appl. No. 09/782,588 dated Jan. 10, 2005.
Office Action from U.S. Appl. No. 09/782,588 dated Apr. 9, 2004.
Office Action from U.S. Appl. No. 09/782,588 dated Jan. 5, 2004.
Office Action from U.S. Appl. No. 09/782,588 dated Oct. 30, 2003.
Office Action from U.S. Appl. No. 09/782,588 dated Feb. 6, 2003.
Office Action from U.S. Appl. No. 09/782,588 dated Jun. 13, 2002.
Office Action from U.S. Appl. No. 10/638,173 dated Mar. 15, 2007.
Office Action from U.S. Appl. No. 10/638,173 dated Sep. 14, 2006.
Office Action from U.S. Appl. No. 10/638,173 dated Apr. 25, 2006.
Office Action from U.S. Appl. No. 09/931,271 dated Oct. 16, 2003.
Office Action from U.S. Appl. No. 09/931,271 dated May 30, 2003.
Office Action from U.S. Appl. No. 09/931,271 dated Sep. 5, 2002.

* cited by examiner

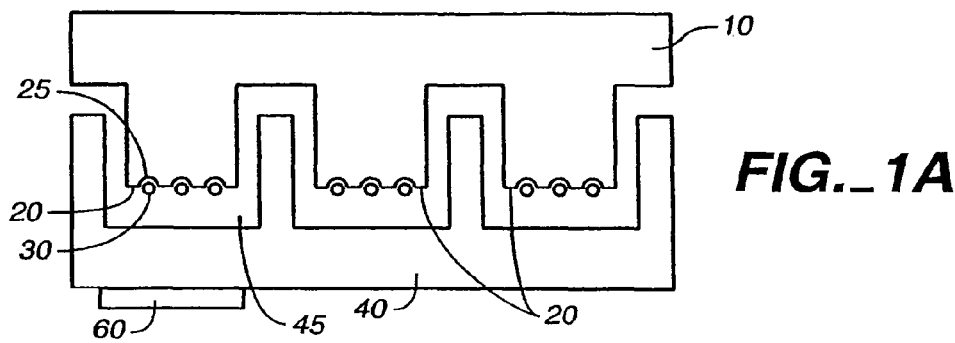
FIG._1A
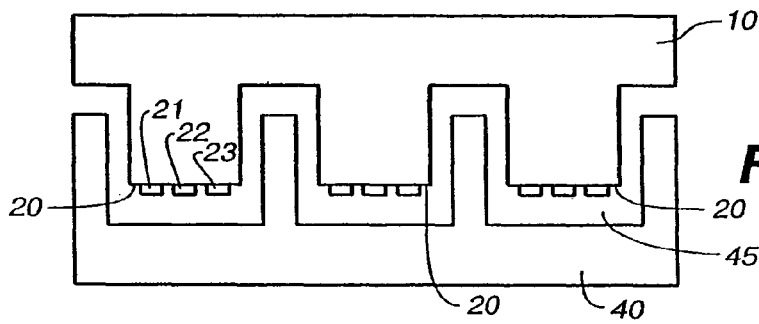
FIG._1B
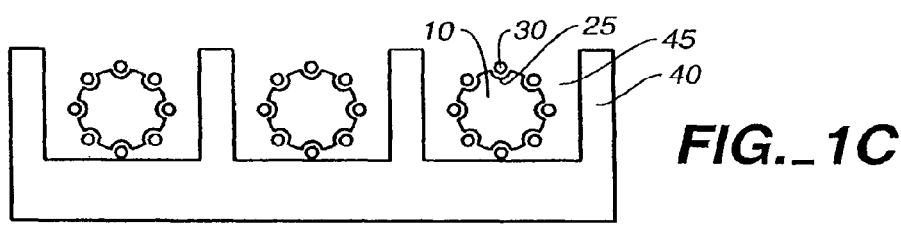
FIG._1C
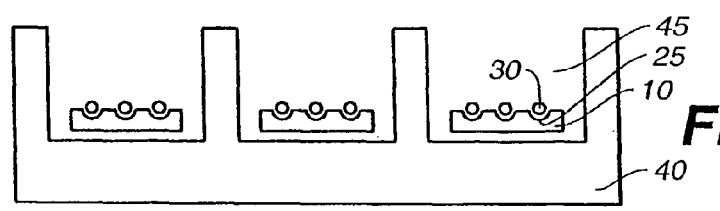
FIG._1D
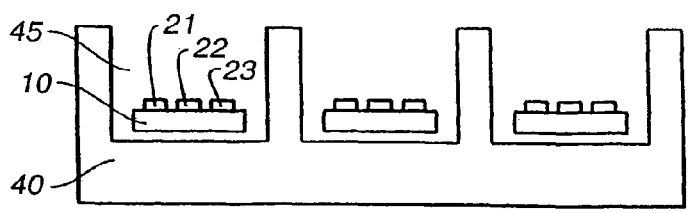
FIG._1E

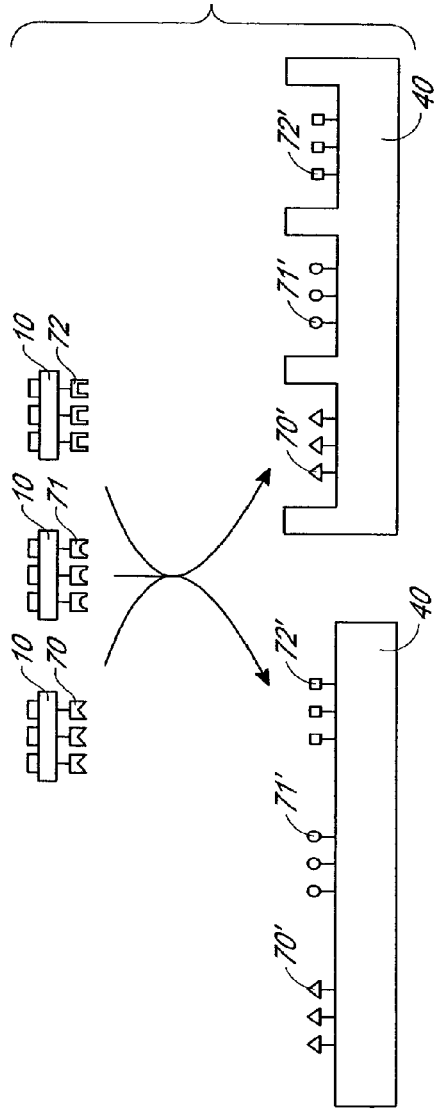
FIG. 1F
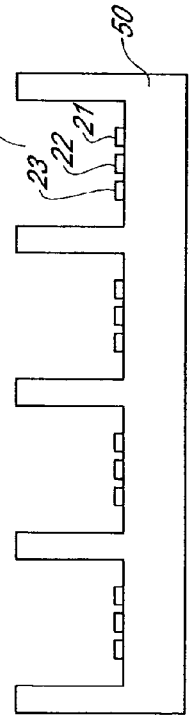
FIG. 2A
FIG. 2B

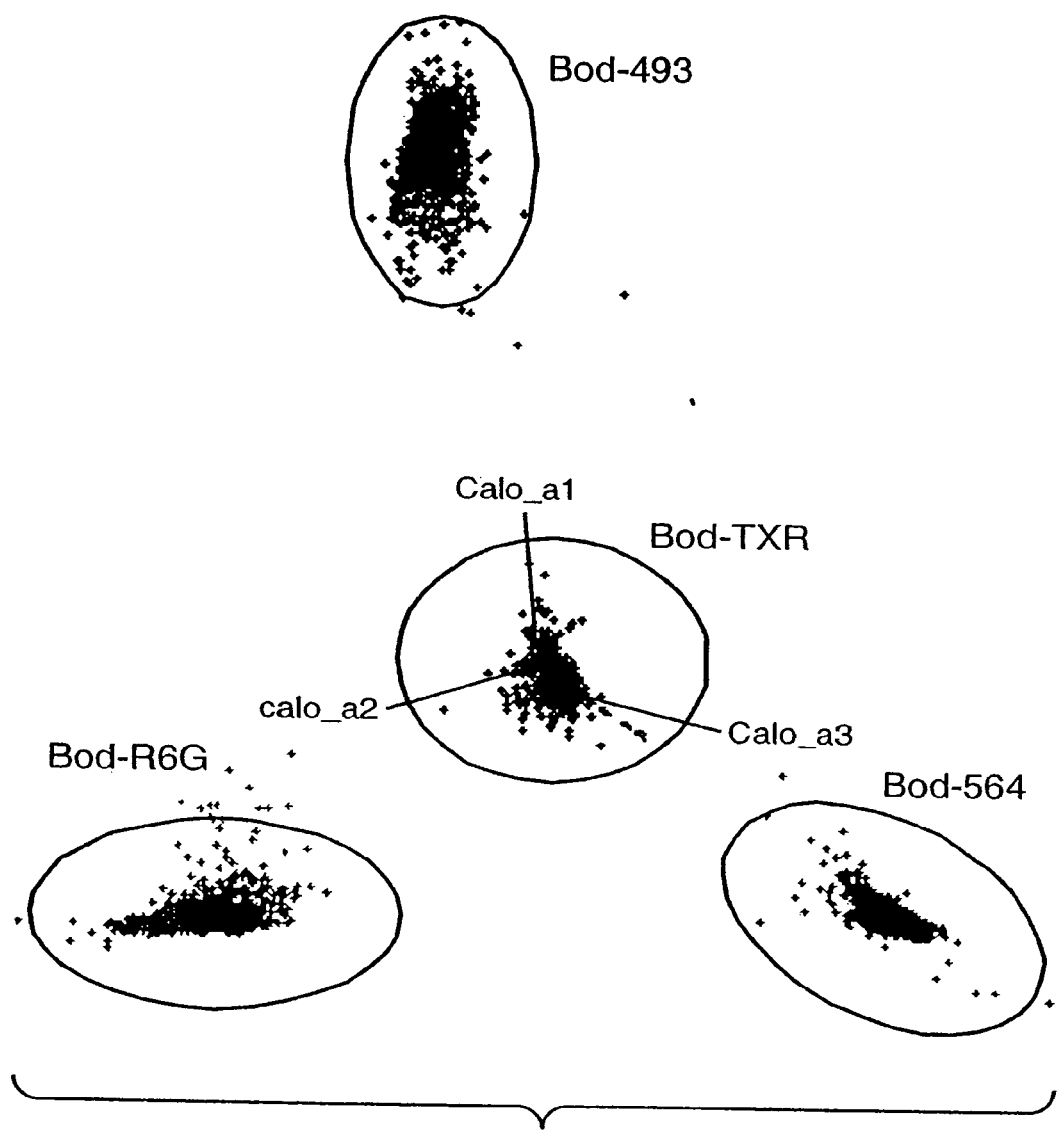
FIG._3

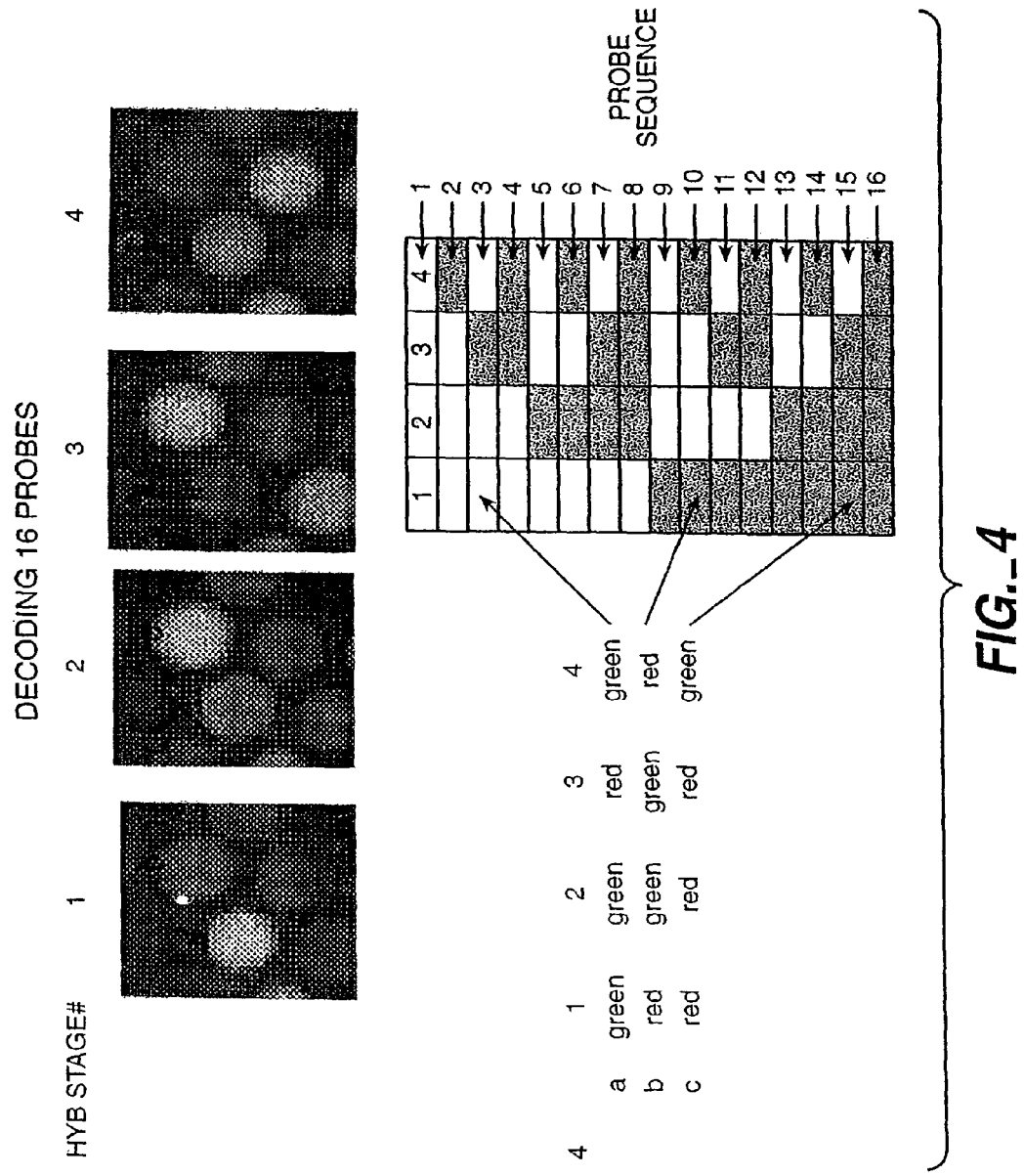
FIG._4

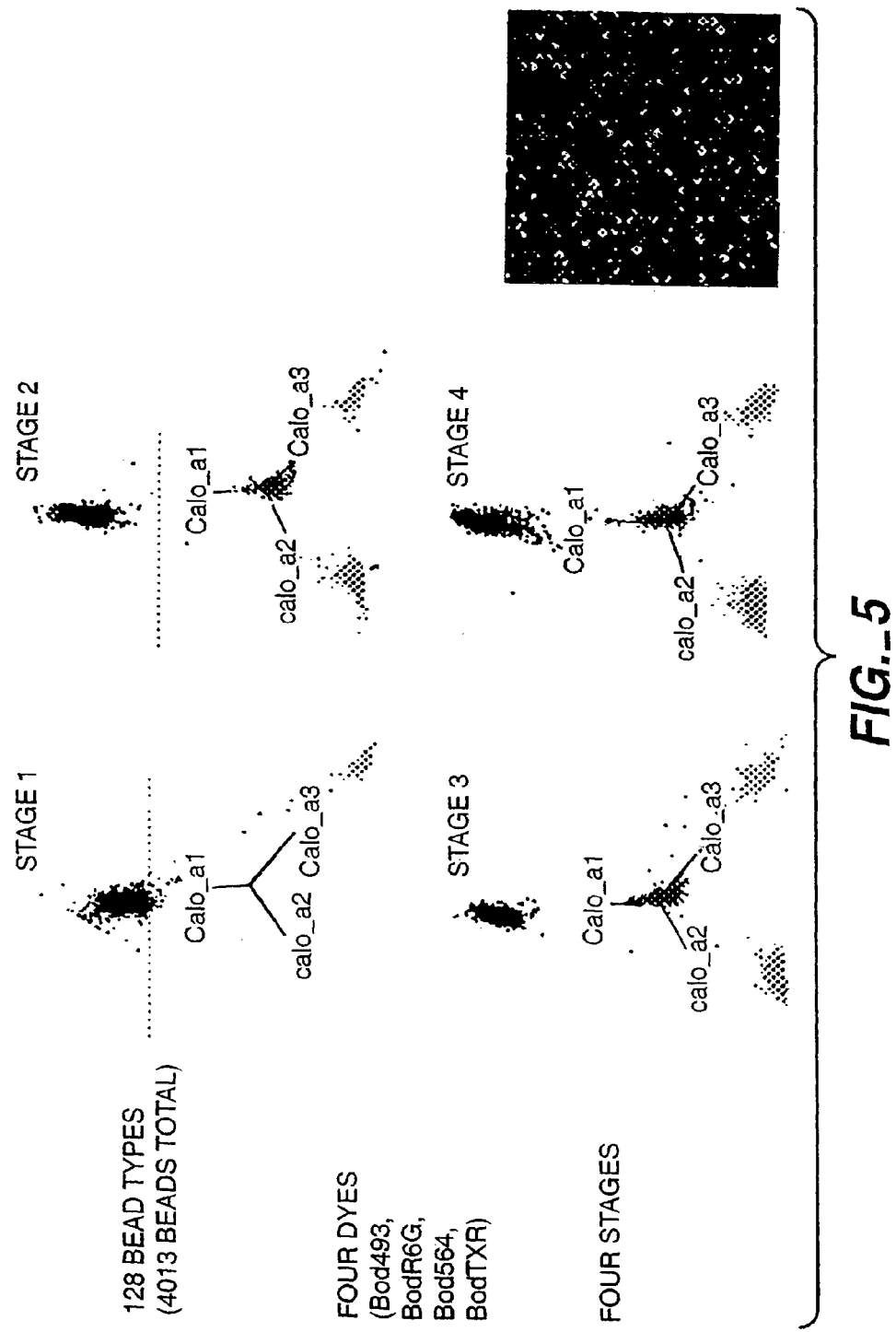
FIG._5

GREYSCALE DECODING
| Code | S1 | S2 | S3 |
|---|---|---|---|
| 1 | 100 | 100 | 100 |
| 2 | 100 | 100 | 40 |
| 3 | 100 | 100 | 10 |
| 4 | 100 | 40 | 100 |
| 5 | 100 | 40 | 40 |
| 6 | 100 | 40 | 10 |
| 7 | 100 | 10 | 100 |
| 8 | 100 | 10 | 40 |
| 9 | 100 | 10 | 10 |
| 10 | 40 | 100 | 100 |
| 11 | 40 | 100 | 40 |
| 12 | 40 | 100 | 10 |
| 13 | 40 | 40 | 100 |
| 14 | 40 | 40 | 40 |
| 15 | 40 | 40 | 10 |
| 16 | 40 | 10 | 100 |
| 17 | 40 | 10 | 40 |
| 18 | 40 | 10 | 10 |
| 19 | 10 | 100 | 100 |
| 20 | 10 | 100 | 40 |
| 21 | 10 | 100 | 10 |
| 22 | 10 | 40 | 100 |
| 23 | 10 | 40 | 40 |
| 24 | 10 | 40 | 10 |
| 25 | 10 | 10 | 100 |
| 26 | 10 | 10 | 40 |
| 27 | 10 | 10 | 10 |
*FIG._6A*
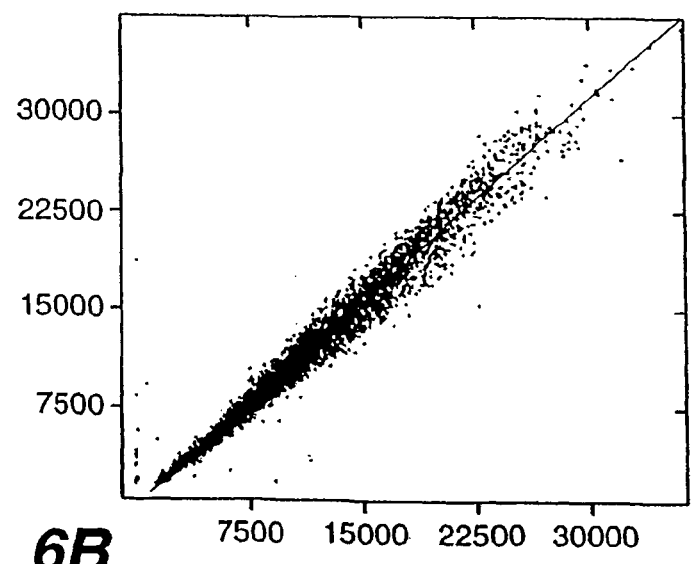
*FIG._6B*

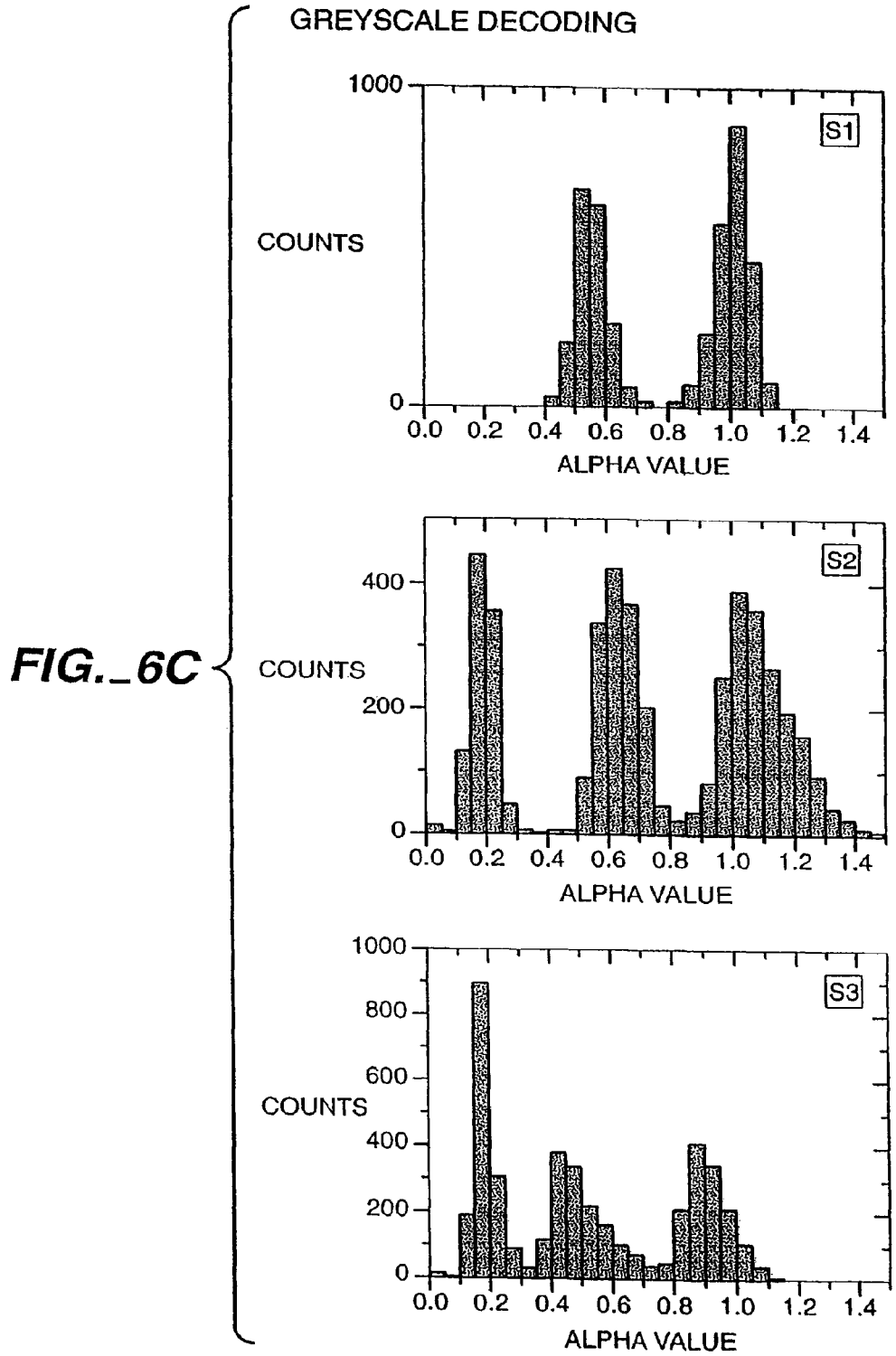
FIG._6C

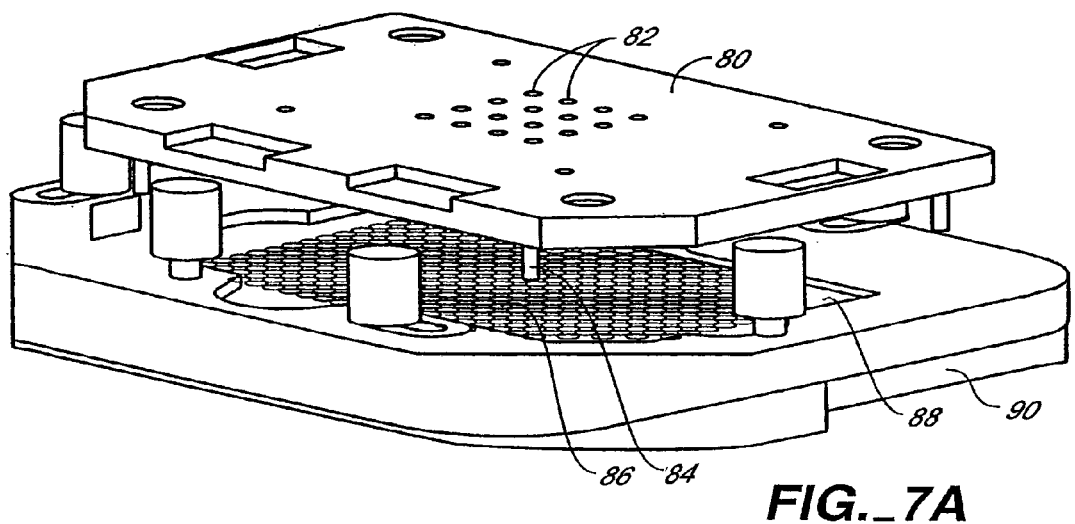
FIG._7A
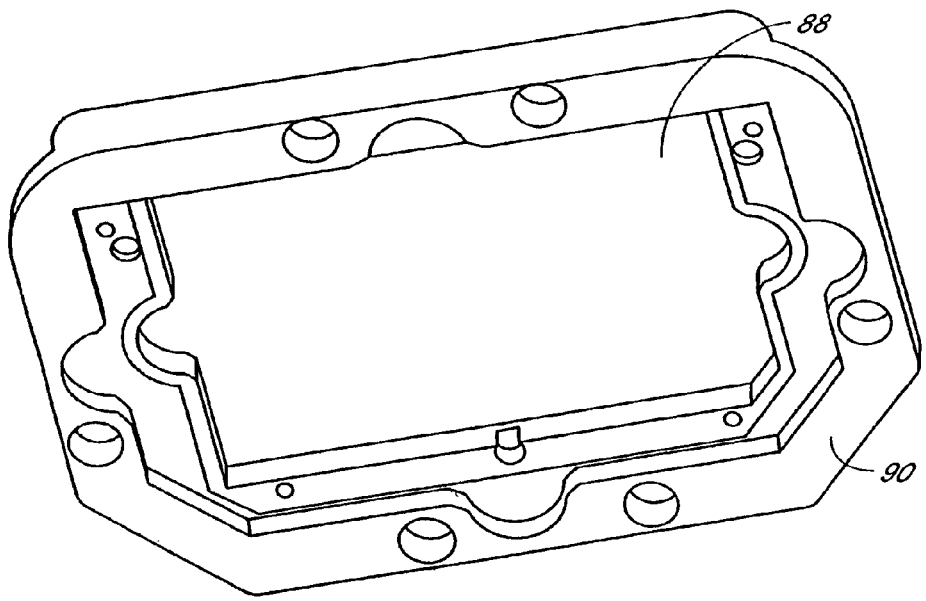
FIG._7B

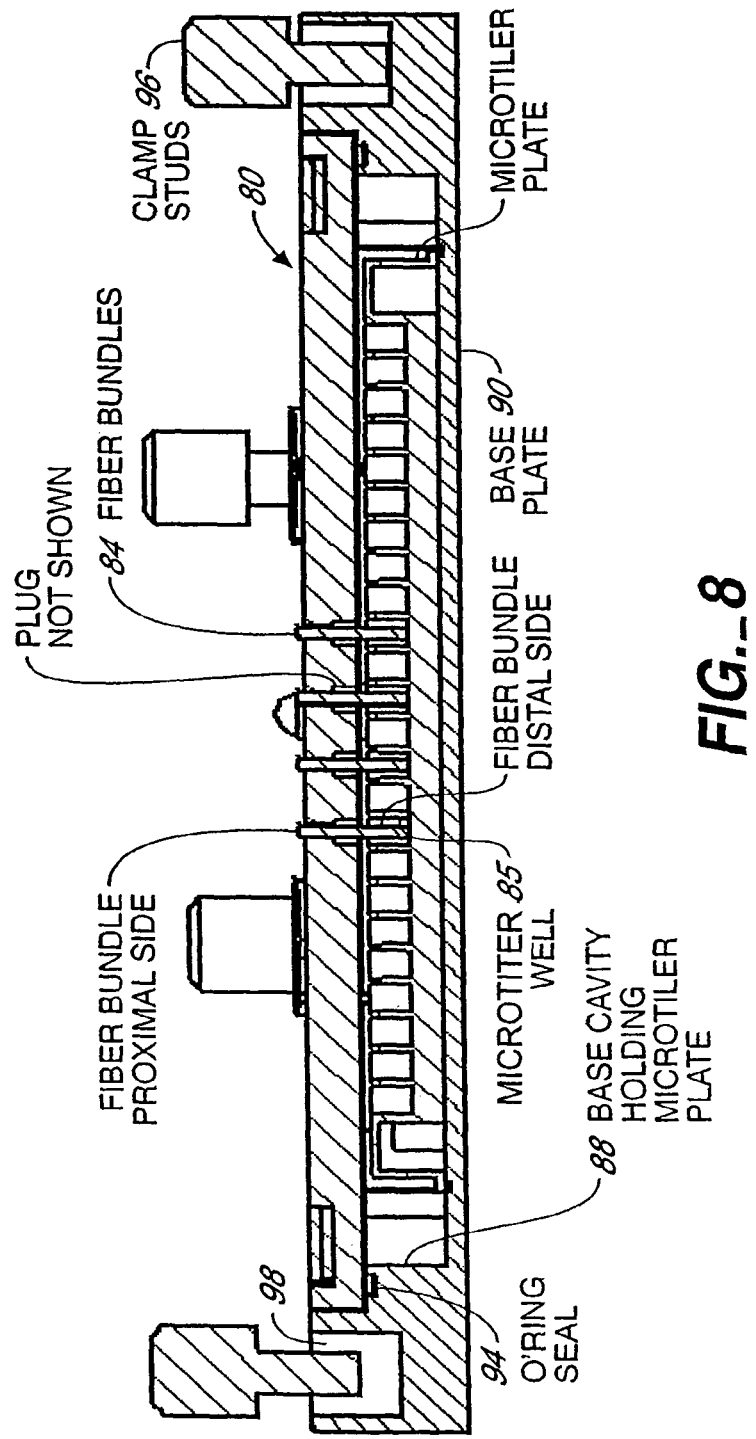

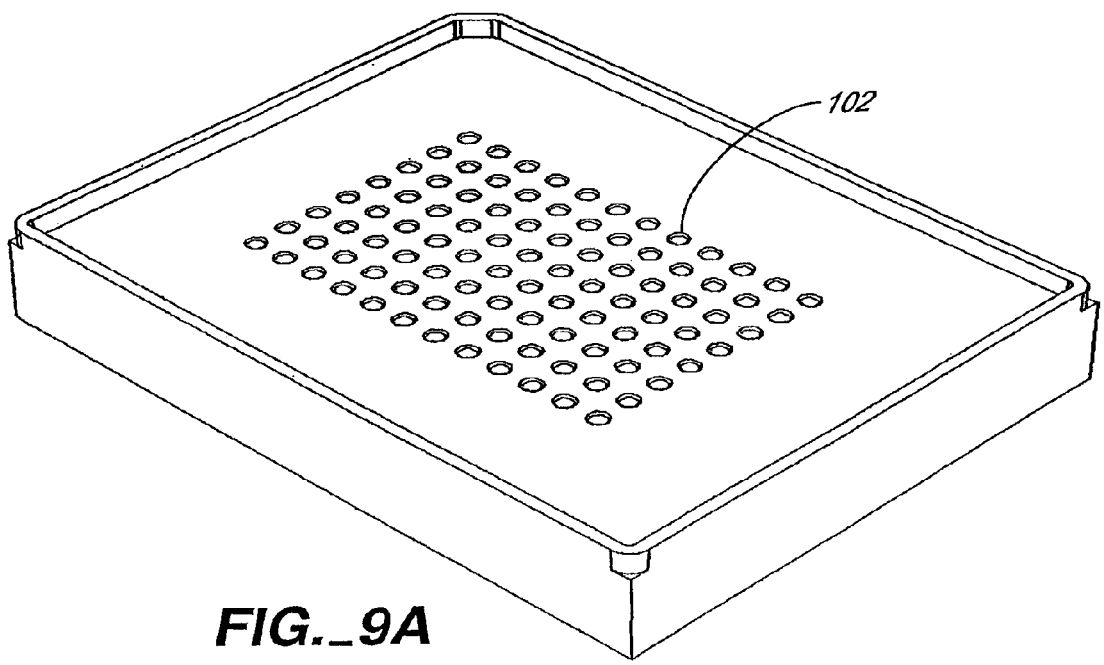
FIG._9A
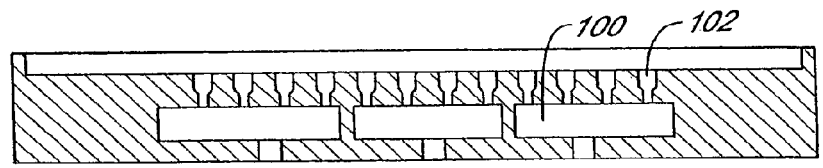
FIG._9B

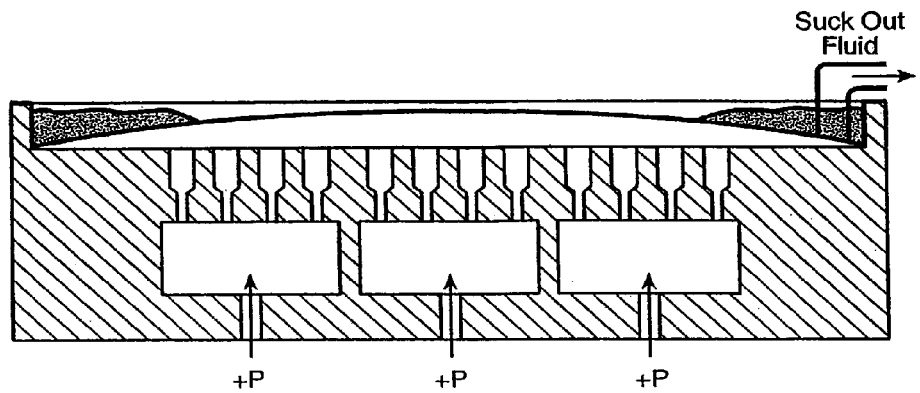
FIG._10A
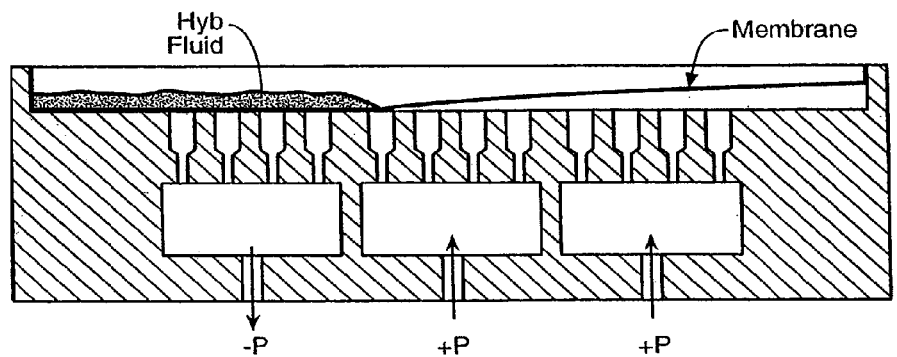
FIG._10B
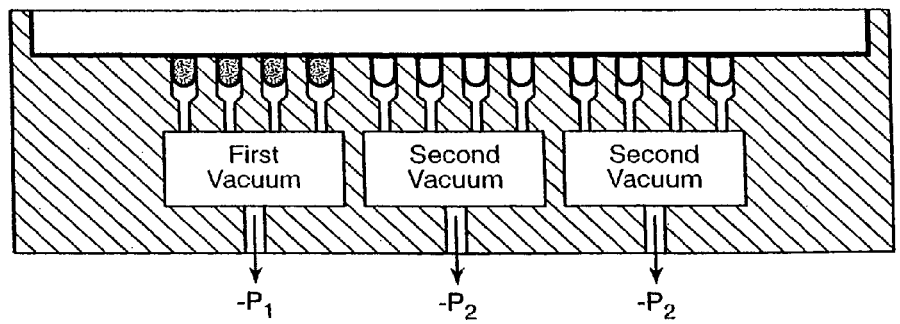
FIG._10C

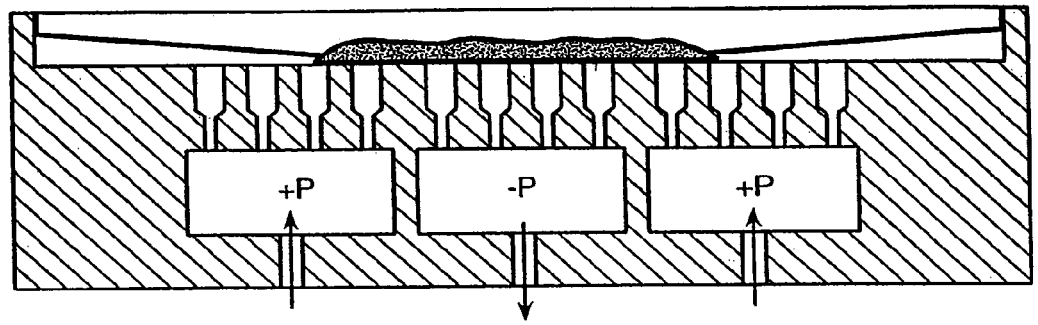
FIG._10D
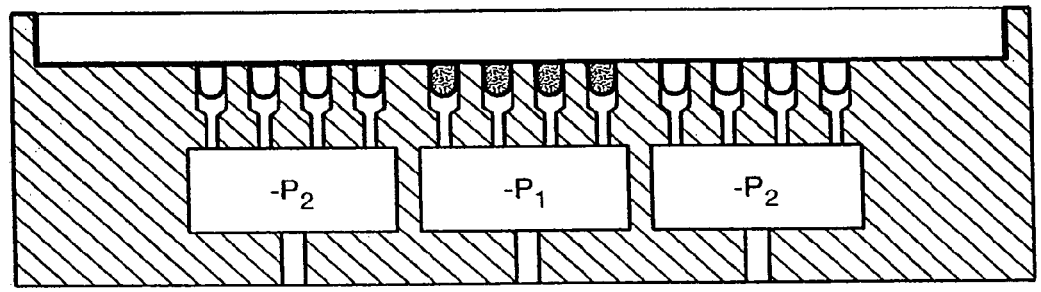
FIG._10E
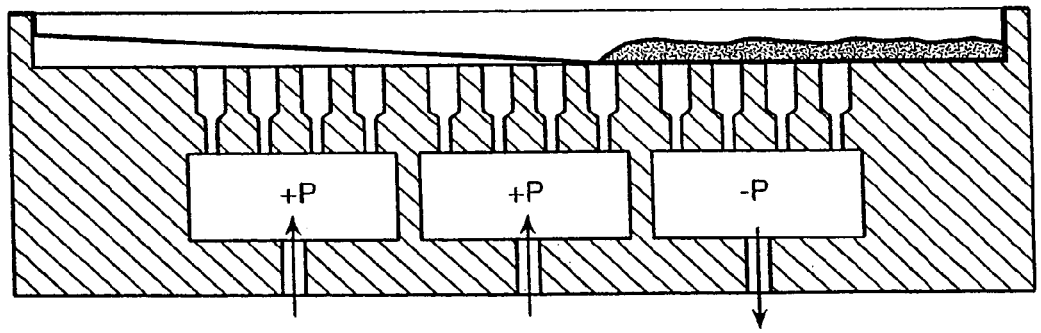
FIG._10F

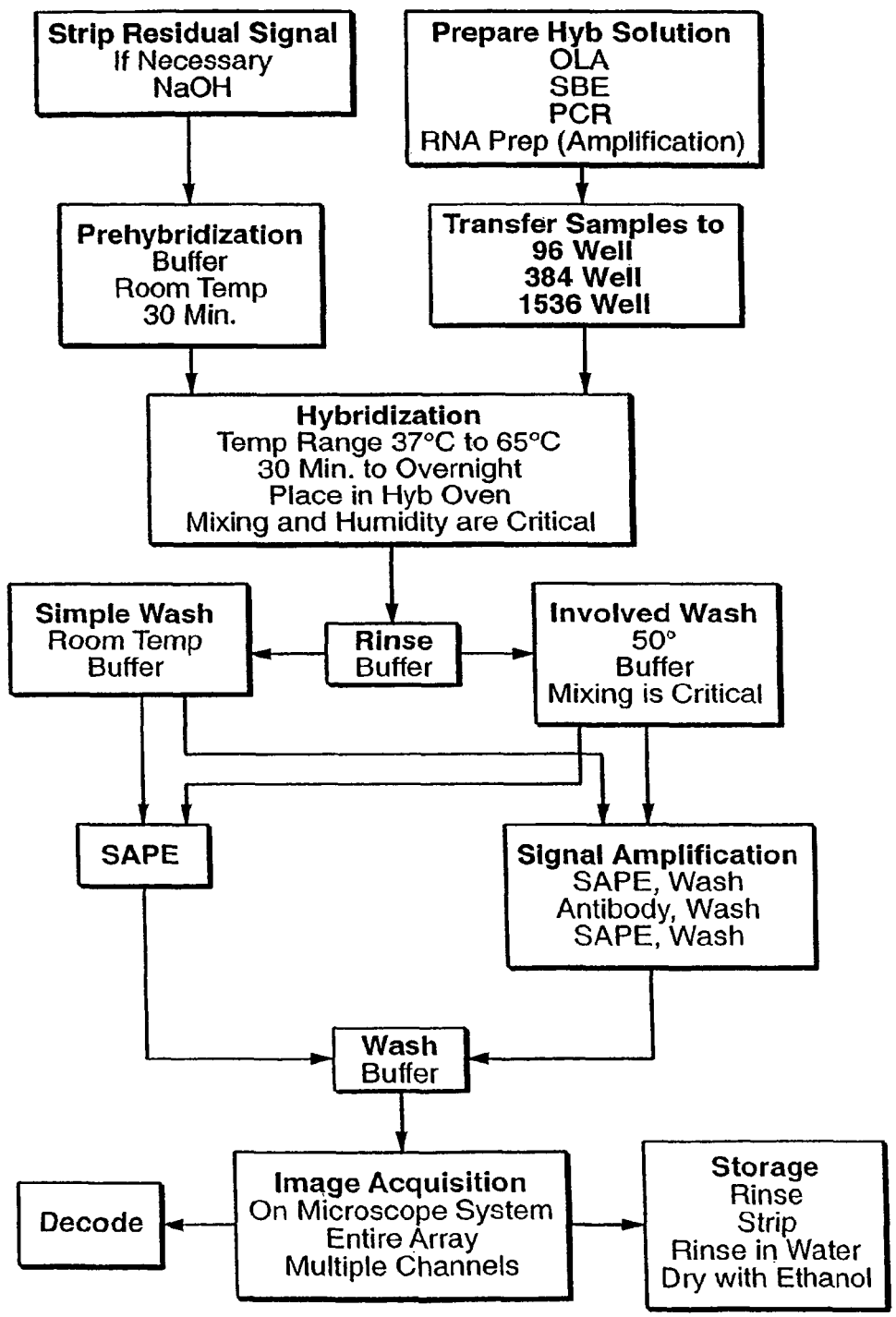
FIG._11

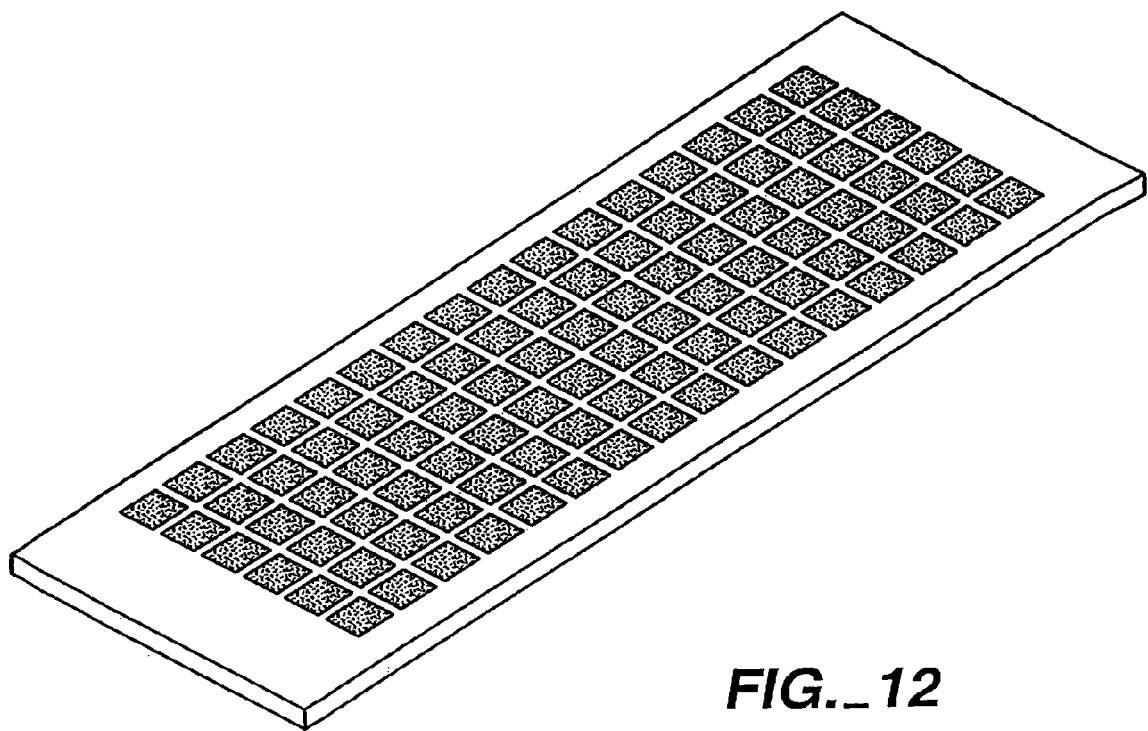
FIG._12

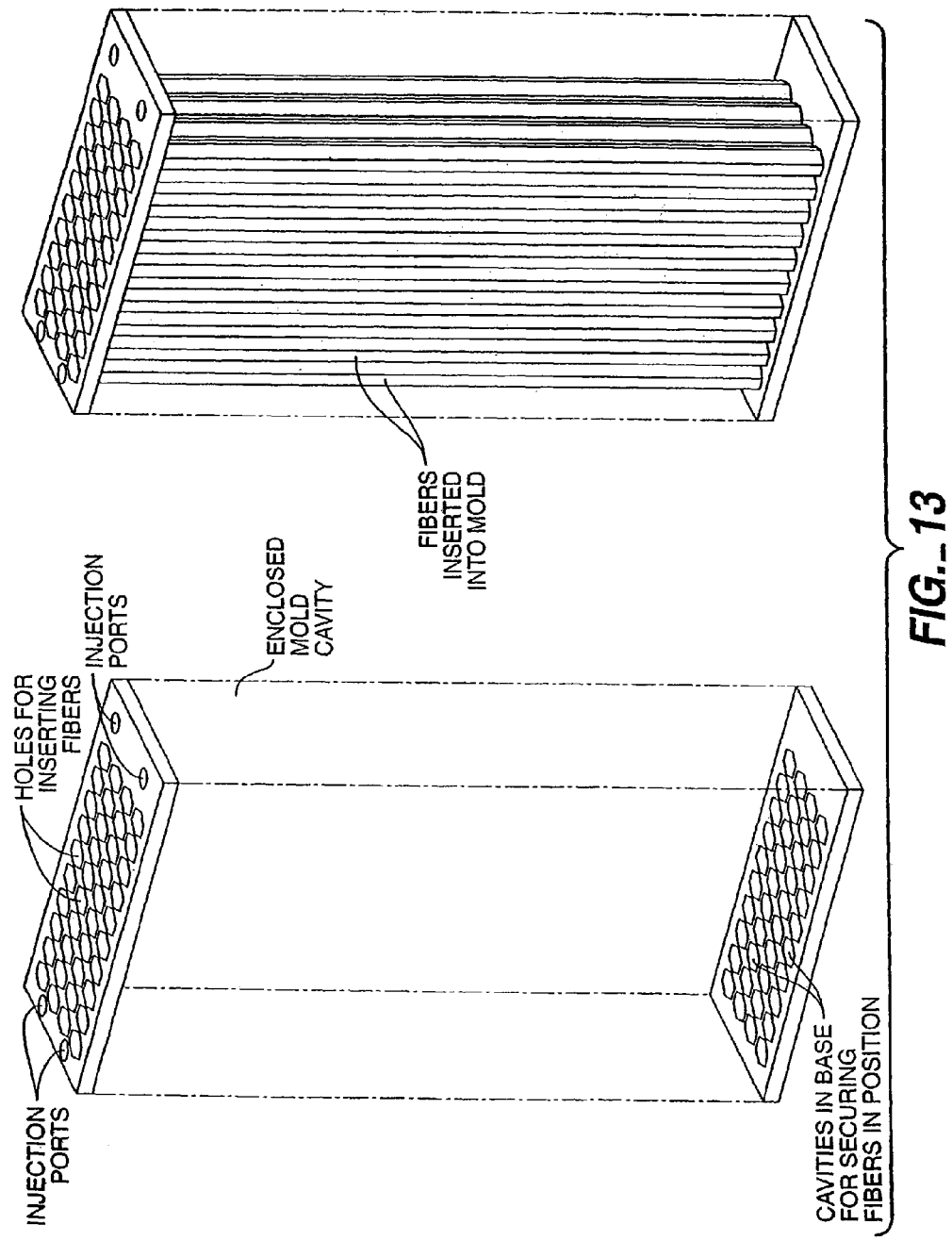
FIG._13

METHODS OF DETECTING TARGETS ON AN ARRAY

RELATED APPLICATIONS

This application is a continuation of U.S. application Ser. No. 10/856,039 filed May 27, 2004, which is a continuation of U.S. application Ser. No. 09/931,271, filed Aug. 16, 2001, now U.S. Pat. No. 6,770,441, issued Aug. 3, 2004, which is a continuation-in-part of U.S. application Ser. No. 09/782,588, filed Feb. 12, 2001, now abandoned, which is a non-provisional application of and claims priority to Provisional Application No. 60/181,631, filed Feb. 10, 2000, all of which are incorporated by reference in their entireties.

BACKGROUND OF THE INVENTION

1. Field of the Invention

The invention relates to methods of detecting a target analyte in a biological sample using composite microsphere arrays having first and second assay locations. Preferred target analytes include nucleic acid, and more specifically, nucleic acid having one or more single nucleotide polymorphisms (SNPs).

2. Description of the Related Art

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, quantum dots etc.

Of particular use in these sensors are detection mechanisms utilizing luminescence. Recently, the use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in C.R.C. Critical Reviews In Analytical Chemistry, Vol. 19, 1988, pp. 135-173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series, Vol.* 403, 1989, p. 252, and Wolfbeis, O. S., *Fiber Optic Chemical Sensors*, Ed. CRC Press, Boca Raton, Fla., 1991, 2nd Volume.

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

U.S. Ser. Nos. 08/818,199 and 09/151,877 describe array compositions that utilize microspheres or beads on a surface of a substrate, for example on a terminal end of a fiber optic bundle, with each individual fiber comprising a bead containing an optical signature. Since the beads go down randomly, a unique optical signature is needed to "decode" the array; i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

In addition, compositions comprising silicon wafers comprising a plurality of probe arrays in microtiter plates have been described in U.S. Pat. No. 5,545,531.

SUMMARY OF THE INVENTION

Embodiments of the invention relate to methods of detecting a target analyte in a biological sample, comprising providing a composite array comprising a substrate having a surface; a first and a second assay location on said surface, wherein said assay locations comprise a population of microspheres, and wherein said microspheres comprise bioactive agents; a physical partition separating said first assay location from said second assay location; adding said biological sample to said first assay location under conditions sufficient to allow said target analyte to bind to said bioactive agents; and detecting the binding of said bioactive agents to said target analyte.

In more specific embodiments, the binding of the bioactive agents to the target analyte can be detected by a change in an optical signature of the microspheres. Target analytes and bioactive agents can include a nucleic acid, for example.

In other embodiments, the microspheres can include labeled single-stranded nucleic acid sequences hybridized to said bioactive agents. In other embodiments, microspheres can be randomly distributed on said surface at said assay locations. In further aspects, microspheres can be separated by a distance of less than 25 µm. In more specific embodiments, the microspheres can be separated by a distance of less than 15 µm.

Methods herein, can further comprise detecting a target analyte in a second biological sample by adding said second biological sample to said second assay location and thereafter detecting the binding of said bioactive agents to said target analyte. In certain aspects the substrate can include a microscope slide.

In further embodiments, the first and second assay locations can be separately sealed to form hybridization chambers. In an advantageous embodiment, the hybridization chambers include flexible membranes.

The physical partitions described herein can be a non-permanent sealant, such as rubber, silicon, petroleum jelly, wax and parafilm. In other embodiments, the physical partition is a ridge or rim of sufficient width and height to prevent the bioactive agents from moving from the first assay location to the second assay location. In still further aspects, the physical partition can be a trough of sufficient width and depth to prevent the bioactive agents from moving from the first assay location to the second assay location.

In advantageous embodiments, the physical partition is a gasket. More particularly, the gasket can be adapted to fit within an indentation or channel on the substrate.

In other embodiments, the target analyte includes a detectable optical label, such as a fluorophore, for example.

Advantageous biological samples can include blood, for example. Additionally, bioactive agents can include a detectable optical label, such as a fluorophore, for example.

Further methods include detecting a target nucleic acid in a biological sample, wherein said target nucleic acid includes one or more single nucleotide polymorphisms (SNPs) at one or more predetermined positions, comprising providing a composite array comprising a substrate having a surface; a population of microspheres, wherein said microspheres are linked to capture probes configured to bind to said target nucleic acid at said one or more predetermined positions; a first and second assay location on said surface, wherein said assay locations comprise said population of microspheres; a physical partition separating said first assay location from said second assay location; adding said biological sample to said first assay location under conditions sufficient to allow said target nucleic acid to bind to said capture probes; and detecting the binding of said target nucleic acid to said capture probes.

In more specific embodiments, the binding of said capture probes to said target nucleic acid can be detected by a change in an optical signature of the microspheres. Advantageously, the microspheres can be randomly distributed on said surface at said assay locations.

In other embodiments, the microspheres can be separated by a distance of less than 25 μm, or by a distance of less than 15 μm.

Methods herein, can further comprise detecting a target analyte in a second biological sample by adding the second biological sample to the second assay location and thereafter detecting the binding of the capture probes to the target analyte.

In particular embodiments, the substrate can include a microscope slide.

Further embodiments, include adding a SNP allele-specific probe, configured to hybridize to said target nucleic acid, wherein the SNP allele-specific probe is labeled with a fluorophore.

Additional aspects of the teachings herein include using a target nucleic acid having one or more SNPs causatively linked to a human disease, such as Alzheimer's disease.

Further methods include using microspheres having labeled single-stranded nucleic acid sequences hybridized to the capture probes. In particular aspects, the capture probes can include a detectable optical label, such as a fluorophore, for example.

The invention also provides array compositions comprising a rigid support; a molded layer with at least a first assay location comprising discrete sites, where the molded layer is adhered to the rigid support; a layer of bonding agent adhering the rigid support to the molded layer; and a population of microspheres comprising at least a first and a second subpopulation, where the first subpopulation comprises a first bioactive agent and the second subpopulation comprises a second bioactive agent where the microspheres are randomly distributed on the sites.

The invention also provides a method for making an array composition containing at least a first assay location having discrete sites comprising the steps of contacting a surface of a template structure, the surface comprising one or more sets of projections, with a moldable material; removing the moldable material from the surface of the template structure, whereby the removed moldable material forms a molded layer with at least a first assay location comprising discrete sites; adhering the molded layer to a rigid support; and randomly distributing microspheres on the molded layer such that individual discrete sites comprise microspheres, where the microspheres comprise at least a first and a second subpopulation, where the first subpopulation comprises a first bioactive agent and the second subpopulation comprises a second bioactive agent.

BRIEF DESCRIPTION OF THE FIGURES

FIGS. 1A, 1B, 1C, 1D and 1E depict several different "two component" system embodiments of the invention. In FIG. 1A, a bead array is depicted. The first substrate 10 has array locations 20 with wells 25 and beads 30. The second substrate 40 has assay locations 45. An optional lens or filter 60 is also shown; as will be appreciated by those in the art, this may be internal to the substrate as well. FIG. 1B is similar except that beads are not used; rather, array locations 20 have discrete sites 21, 22, 23, etc. that may be formed using spotting, printing, photolithographic techniques, etc. FIGS. 1C-F depict the use of a plurality of first substrates. FIG. 1C depicts a "bead of beads" that may have additional use for mixing functions. FIG. 1D depicts a plurality of bead arrays and FIG. 1E depicts a plurality of non-bead arrays. FIG. 1F depicts the use of binding functionalities to "target" first substrates 10 to locations on the second substrate 40; as will be appreciated by those in the art, this may be done on flat second substrates or on compartmentalized second substrates. FIG. 1F utilizes binding ligand pairs 70/70', 71/71', 72/72', etc. These may be either chemical functionalities or biological ones, such as are described for IBL/DBL pairs, such as oligonucleotides, etc.

FIGS. 2A and 2B depict two different "one component" systems. FIG. 2A depicts a bead array, with the substrate 50 having assay locations 45 with wells 25 comprising beads 30. FIG. 2B depicts a non-bead array; each assay location 45 has discrete sites 21, 22, 23, etc.

FIG. 3 depicts clustering in hyperspectral alpha space (a1=I1/SIi, a2=I2/SIi, a3=I3/SIi, etc.). A set of 128 different bead types present on a fiber bundle were decoded with by hybridizing set of complementary oligonucleotides labeled with four dyes: Bodipy-493, Bodipy-R6G, Bodipy-TXR, and Bod-564 (only one dye per oligonucleotide). Shown is the second stage of a four stage decode in which 4013 beads were decoded. Ovals are drawn around zones of hue clusters.

FIG. 4 Illustrates a two color decoding process wherein either FAM-labeled or Cy3-labeled oligo complements are use to "paint" (label) the different bead types on the array.

FIG. 5 depicts the decoding 128 different bead types with four colors and four decode stages. (inset shows a single decode stage using four different dyes to decode 16 bead types.)

FIG. 6 depicts grey scale decoding of 16 different bead types. (A) Combinatorial pooling scheme for complementary decoding oligos. A (B) Two independent normalizing images were acquired, and the resulting bead intensities compared. (C) The alpha values (ratio of bead intensity in indicated decode stage to intensity in normalization image) are plotted for three decodes stage described in (A).

FIG. 7 schematically depicts the lid and base plate. A. Depicts the lid 80 and base plate 90 of the hybridization chamber. Ports 82 in the lid allow for fiber optic bundles 84 to be inserted through the lid and contact the sample in the wells of the microtiter plate 86 in the base cavity 88 of the base plate 90. B. Depicts the base cavity 88 of the base plate 90.

FIG. 8 schematically depicts the hybridization chamber including the lid 80 and base plate 90. Also shown are the peripheral seal 94, the clamp 96 and clamp receptacle 98, fiber optic bundles 84 inserted through the lid and into the well of the microtiter plate 86.

FIG. 9 depicts a base plate with holes 102. A Depicts the holes 102 in the base plate. B Depicts channels 100 connecting the holes 102.

FIG. 10 depicts variable solution volume and localization on the membrane caused by pressure and/or vacuum. A. +P indicates pressure; –P indicates vacuum. Upward bending of the membrane in response to pressure in all chambers and holes. B. Fluid is moved to the left side of the membrane when vacuum is applied to the left chambers and pressure is applied to the middle and right chambers. C. When vacuum is first applied to the left section, fluid fills the wells. When vacuum is subsequently applied to the middle and right chambers, empty wells are formed. D. Fluid moves to the center of the membrane when vacuum is applied to the center and pressure is applied to left and right chambers. E. Fluid fills in wells formed by high vacuum in the center. Empty wells form on the left and right when low vacuum is applied. F. Fluid moves to the right when vacuum is applied to the right chamber and pressure is applied to the left and middle chambers.

FIG. 11 depicts a flow chart of a representative assay scheme that finds use with the hybridization chamber.

FIG. 12 depicts an array of arrays in a microscope slide format.

FIG. 13 depicts a mold for making arrays.

FIG. 14 depicts formation of a submaster structure and use of the submaster structure to form a molded layer adhered to a rigid support in accordance with an embodiment of the method of the invention.

FIG. 16A depicts direct attachment; the capture probe 120 hybridizes to a first portion of the target sequence 125. FIG. 16B depicts the use of a capture extender probe 130 that has a first portion that hybridizes to the capture probe 120 and a second portion that hybridizes to a first domain of the target sequence 125. FIG. 16C shows the use of an adapter sequence 135, that has been added to the target sequence, for example during an amplification reaction as outlined herein.

DETAILED DESCRIPTION OF THE INVENTION

Overview

Figure 14A:
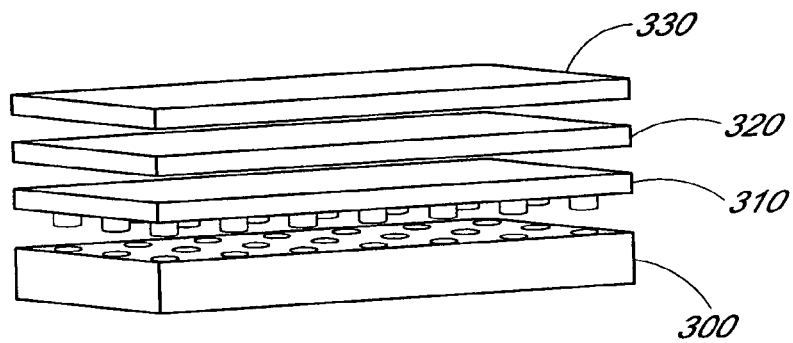
In FIG. 14A a master structure 300 is used to form a submaster structure 310 which can be coated with a bonding agent 320 and adhered to a rigid support 330.

The present invention is directed to the formation of very high density arrays that can allow simultaneous analysis, i.e. parallel rather than serial processing, on a number of samples. This is done by forming an "array of arrays", i.e. a composite array comprising a plurality of individual arrays, that is configured to allow processing of multiple samples. For example, each individual array can be present within each well of a microtiter plate. Thus, depending on the size of the microtiter plate and the size of the individual array, very high numbers of assays can be run simultaneously; for example, using individual arrays of 2,000 distinct species (with high levels of redundancy built in) and a 96 well microtiter plate, 192,000 experiments can be done at once; the same arrays in a 384 microtiter plate yields 768,000 simultaneous experiments, and a 1536 microtiter plate gives 3,072,000 experiments.

Composite arrays of the present invention are not limited to the configuration of a microtiter plate, and can be formed to have any of a variety of dimensions and designs, as described below. The composite arrays of the present invention are produced using a process designed for production-scale manufacture of surfaces with fine features (i.e., features as small as sub-micron scale). Briefly, this process, which is also contemplated herein as an embodiment of the present invention, includes contacting a template structure with a moldable material, where the template structure has one or more sets of projections on its surface. The moldable material is then removed from the template structure as a molded layer, which is then adhered to a rigid support. The resultant composite array will contain surface features of the molded layer that are complementary to that of the template structure and contain at least one array of discrete sites, and will also have sufficient rigidity to permit accurate optical interrogation of the discrete sites.

Generally, the array compositions of the invention can be configured in several ways. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing bioactive agents can then be loaded into the bead wells in each assay location as is more fully described below. It should be noted that while the disclosure herein emphasizes the use of beads, beads need not be used in any of the embodiments of the invention; the bioactive agents can be directly coupled to the array locations. For example, other types of arrays are well known and can be used in this format; spotted, printed or photolithographic arrays are well known; see for example WO 95/25116; WO 95/35505; PCT US98/09163; U.S. Pat. Nos. 5,700,637; 5,807,522 and 5,445,934; and U.S. Ser. Nos. 08/851,203 09/187,289; and references cited within, all of which are expressly incorporated by reference. In one component systems, if beads are not used, preferred embodiments utilize non-silicon wafer substrates.

The present invention is generally based on previous work comprising a bead-based analytic chemistry system in which beads, also termed microspheres, carrying different chemical functionalities are distributed on a substrate comprising a patterned surface of discrete sites that can bind the individual microspheres. The beads are generally put onto the substrate randomly, and thus several different methodologies can be used to "decode" the arrays. In one embodiment, unique optical signatures are incorporated into the beads, generally using fluorescent dyes, that can be used to identify the chemical functionality on any particular bead. This allows the synthesis of the candidate agents (i.e. compounds such as nucleic acids and antibodies) to be divorced from their placement on an array; i.e., the candidate agents may be synthesized on the beads, and then the beads are randomly distributed on a patterned surface. Since the beads are first coded with an optical signature, this means that the array can later be "decoded", i.e.

after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art. These methods are generally outlined in PCT US98/05025; PCT US98/21193; PCT US99/20914; PCT US99/14387; and U.S. Ser. Nos. 08/818, 199; 09/315,584; and 09/151,877, all of which are expressly incorporated herein by reference. In addition, while the discussion herein is generally directed to the use of beads, the same configurations can be applied to cells and other particles; see for example PCT US99/04473.

In these systems, the placement of the bioactive agents is generally random, and thus a coding/decoding system is required to identify the bioactive agent at each location in the array. This may be done in a variety of ways, as is more fully outlined below, and generally includes: a) the use of a decoding binding ligand (DBL), generally directly labeled, that binds to either the bioactive agent or to identifier binding ligands (IBLs) attached to the beads; b) positional decoding, for example by either targeting the placement of beads (for example by using photoactivatible or photocleavable moieties to allow the selective addition of beads to particular locations), or by using either sub-bundles or selective loading of the sites, as are more fully outlined below; c) selective decoding, wherein only those beads that bind to a target are decoded; or d) combinations of any of these. In some cases, as is more fully outlined below, this decoding may occur for all the beads, or only for those that bind a particular target analyte. Similarly, this may occur either prior to or after addition of a target analyte.

Once the identity (i.e. the actual agent) and location of each microsphere in the array has been fixed, the array is exposed to samples containing the target analytes; although as outlined below, this can be done prior to or during the analysis as well. The target analytes will bind to the bioactive agents as is more fully outlined below, resulting in a change in the optical signal of a particular bead.

Array

Accordingly, the present invention provides array compositions comprising a molded layer with a surface comprising one or more assay locations. By "array" herein is meant a plurality of candidate agents in an array format; the size of the array will depend on the composition and end use of the array. Arrays containing from about 2 different bioactive agents (e.g., different beads) to many millions can be made, with very large fiber optic arrays being possible. Generally, the array will comprise from two to as many as a billion or more, depending on the size of the beads and the substrate, as well as the end use of the array; thus very high density, high density, moderate density, low density and very low density arrays may be made. Preferred ranges for very high density arrays are from about 10,000,000 to about 2,000,000,000, (with all numbers being per square centimeter) with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being preferred, and from about 20,000 to about 50,000 being especially preferred. Low density arrays are generally less than 10,000, with from about 1,000 to about 5,000 being preferred. Very low density arrays are less than about 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 µm or less (with beads of 200 nm possible) can be used, and very small fibers are known, it is possible to have as many as 40,000-50,000 or more (in some instances, 1 million) different fibers and beads in a 1 $mm^2$ fiber optic bundle, with densities of greater than 15,000,000 individual beads and fibers (again, in some instances as many as 25-50 million) per 0.5 $cm^2$ obtainable.

By "composite array" or "combination array" or grammatical equivalents herein is meant a plurality of individual arrays, as outlined above. The number of arrays in a composite array is not necessarily limited to any particular number, and will be determined according to any of a variety of factors considered by one skilled in the art, including corresponding equipment, number of samples to be tested, convenience of experimental design, and the like. For example, the number of individual arrays can be set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

As will be appreciated by one skilled in the art, a configuration of a composite array is not limited to the dimensions of a microtiter plate. A composite array configuration may be a single array, or may be a one-dimensional composite of arrays, i.e. a composite array having only one array in a first dimension and a plurality of arrays in a second dimension. Furthermore, a composite array can be a square, e.g., 2×2, 3×3, etc., or any other configuration, including, but not limited to, concentric circles, spiral, rectangular, triangular, and the like. Preferably, the composite of arrays contain regularly spaced arrays in lattice configuration. In a preferred embodiment, the composite of arrays forms a square or rectangular lattice.

By "substrate" or other grammatical equivalents herein is meant a rigid structure containing at least one assay location having discrete sites. In a preferred embodiment, a substrate of the invention array composition contains a combination of a rigid support and a molded layer adhered thereto, where the molded layer contains at least one assay location having discrete sites. In a preferred embodiment the substrate is in the form or dimensions of a standard microscope slide.

As used herein, a "molded layer" refers to a structural component of the substrate that contains discrete individual sites appropriate for the attachment or association of beads, and which is amenable to at least one detection method. As outlined below, typically the discrete sites of the molded layer are formed using a template structure, such as a template structure having one or more sets of projections, which impresses the discrete sites into the moldable material. The molded layer can generally be any thickness which permits any structural features such as discrete sites and fluid barriers to be maintained and functional. In one embodiment, the thickness of the layer will be determined according to the desired optical properties of the molded layer, as discussed below. The molded layer will usually be at least about 10 µm in thickness and can be 1 µm or more in thickness. Typically, the molded layer will range from about 50 µm to about 500 µm in thickness.

As will be appreciated by those in the art, the possible compositions that can be used to form a molded layer are quite varied. In a particularly preferred embodiment, a molded layer comprises a material that can be molded to form discrete individual sites and can be subsequently hardened to maintain the form of the discrete individual sites. A molded layer will typically be selected to have one or more of the following properties: resistant to microcracking; resistant to moisture uptake; having a low thermal expansion coefficient; having low fluorescence; robust and non-deformable; capable of being rigid; capable of being robust and non-deformable; capable of being planar; capable of permanently adhering to an underlying rigid support without use of a bonding agent; capable of permanently adhering to an underlying rigid support with use of a bonding agent; capable of retaining microspheres. Possible molded layer compositions include, but are not limited to resins, including polyimides, epoxies, and the like; plastics, including polycarbonate, acrylics, polystyrene and copolymers of styrene and other materials, polypropylene, polyethylene, polybutylene, polyurethanes, TeflonJ, and the like; polysaccharides; nylon; nitrocellulose; or a variety of other polymers. Exemplary molded layer compositions are disclosed in U.S. Pat. No. 4,582,885, which is herein incorporated by reference. In a preferred embodiment the molded layer is a resin, most preferably an epoxy. In another preferred embodiment the molded layer is made of a thermosetting or thermoplastic polymer. In yet another embodiment of the invention the molded layer is a plastic, most preferably polycarbonate.

In another embodiment, in addition to the above properties of a molded layer, a molded layer is further suitable for large-scale production, having characteristics such as being inexpensive, easily formed in large quantities, capable of setting rapidly; capable of being rapidly adhered to a rigid support; capable of being stored for long periods of time, and the like. In one embodiment, the molded layer is a polymer with well-characterized molding properties. Examples of such polymers include resins such as epoxies and polycarbonate.

In one preferred embodiment, the molded layer is sufficiently rigid such that it need not be adhered to a rigid support in order to retain flatness or planarity. Thus, the invention also provides a rigid molded layer. In this embodiment, the array composition of the invention can comprise a molded layer, and need not also comprise a rigid support nor the corresponding bonding agent for bonding the molded layer to the rigid support. Such a rigid molded layer will, in addition to having properties of a molded layer, have one or more properties of a rigid support as discussed herein. Preferably, a rigid molded layer will be capable of being substantially flat or planar. In addition, a rigid molded layer is preferably flat or planar such that substantially all discrete sites can be accurately and simultaneously optically interrogated. Rigid molded layers can be formed from a variety of materials including polymers such as thermosetting plastics and polycarbonates; a preferred material is polycarbonate.

In another embodiment, the molded layer will be selected according to the desired optical properties of the molded layer. The desired optical properties will be determined according to one or more of a variety of factors, including but not limited to, the type of radiation to be detected, the type and position of the detector, the manner of carrying out excitation (if desired), the strength of the detected signal, the proximity of the discrete sites, and the like. For example, a molded layer can be selected to have particular properties with respect to excitory or detectable radiation such as: having low autofluorescence; being transparent; being absorbent; being selectively absorbent, for example, to one or more wavelengths of light; being selectively transparent, for example of a narrow range of wavelengths, such as a filter; being opaque; or being reflective. In general, the molded layer allows optical detection and does not itself appreciably fluoresce.

In another embodiment, the molded layer can comprise a layer with desired optical properties, such as a reflective layer, which can be employed to enhance signal collection from the arrays. Such a reflective layer can be formed from, for example, a metal layer. Examples of reflective layers are generally described in U.S. Pat. Nos. 5,080,465 and 5,999,318, which are herein incorporated by reference. Such a molded layer comprising more than one layers is discussed below.

In a preferred embodiment, the molded layer comprises a compound that prolongs the desired optical properties of the molded layer. For example, the molded layer can comprise a compound that prolongs the transparency of the molded layer that has been exposed to ultraviolet light or other radiation. A molded layer can also comprise a compound that, for example reduces oxidation-mediated degradation of the optical properties of the molded layer.

In a preferred embodiment, the molded layer is selected according to the hydrophobicity properties of the sample-containing solvent used in methods of the invention for detecting a target analyte. For example, if an aqueous solvent is used, the molded layer will be sufficiently hydrophilic to permit the sample to contact the microspheres in the discrete sites. Similarly, if a hydrophobic or apolar solvent, such as hexanes, toluene, ether, and the like, is used, the molded layer will be sufficiently apolar to permit the sample to contact the microspheres in the discrete sites.

In a preferred embodiment, the molded layer is selected according to a desired level of wetability of the discrete sites. As used to herein, wetability refers to the ability of the entire area of a surface to come into contact with an aqueous or polar solvent which has been placed thereon. The wetability can be achieved in any of a number of ways, including selecting a composition for the entire molded layer which has the desired wetability properties, selecting a molded layer comprising a layer with the desired wetability properties; and modifying the surface of the discrete sites to improve wetability of the discrete sites. Methods of modifying the surface of discrete sites to improve wetability include, but are not limited to acid etching, ion bombardment, and acid/tin etching such as that disclosed in U.S. Pat. No. 3,666,527.

In another embodiment, the molded layer can be selected to increase the ability for a nonpolar or hydrophobic solvent to come into contact with the discrete sites on the surface of the molded layer. This can be achieved in any of a number of ways, including selecting a composition for the entire molded layer which has the desired hydrophobic contacting properties, selecting a molded layer comprising a layer with the desired hydrophobic contacting properties; and modifying the surface of the discrete sites to improve hydrophobic contacting properties of the discrete sites.

In one embodiment, in addition to a molded layer, a substrate also contains a rigid support. As used herein, a "rigid support" refers to a structural component of a substrate that causes a substrate to be inflexible or to retain structural memory. That is, a rigid support will either substantially prevent the substrate from deforming or will, upon deformation of the substrate, cause a substrate to substantially return to the substrate's intended shape. As will be recognized by one skilled in the art, "substantially prevent", "substantially return" and like terms refer to structural properties where the shape of the structure is maintained or reinstated in such a way as to permit the desired optical interrogation of the invention arrays, in accordance with the methods taught and cited herein. In a preferred embodiment, a rigid support is flat or planar such that substantially all discrete sites of an array can be accurately and simultaneously detected. In another preferred embodiment, a rigid support is inflexible, such as, for example, a glass slide. In addition, the rigid support can serve to keep the molded layer in a planar or flat configuration. As is known in the art, many detection techniques, for example, fluorescence detection, rely on very shallow depth of field detection methods using, for example, CCD cameras and confocal microscopes. Since many molded materials cannot be made sufficiently flat or planar for such detection methods, a rigid support is used to maintain the molded layer in a flat or planar configuration.

A rigid support can be formed from any of a variety of materials and will be selected according to the desired properties of the rigid support, including, but not limited to the above-discussed structural properties and other structural properties such as flatness, strength, stiffness, low thermal expansion coefficient, optical properties and chemical properties such as molded layer compatibility. For example, a rigid structure can be selected to have optical properties that include, but are not limited to having low autofluorescence, or being transparent, selectively transparent, absorptive, selectively absorptive, opaque or reflective. In addition, a metal or metal-coated rigid structure can be employed to enhance signal collection from the arrays.

Compositions for a rigid support which demonstrate the above properties include metals, such as aluminum, iron, steel, various alloys, and the like; ceramics; composites such as fiberglass; silicon or other semiconductor materials; glass; rigid plastics or polymers; and the like.

In a preferred embodiment, a substrate containing discrete sites is formed according to the method of the invention, as described in detail below. Briefly, this method includes the steps of: contacting a surface of a template structure, which surface has one or more sets of projections, with a moldable material; then removing the moldable material from the surface of the template structure, such that the removed moldable material forms a molded layer with at least a first assay location having discrete sites; and then adhering the molded layer to a rigid support.

In a preferred embodiment of the method of the invention the invention further includes the step of randomly distributing microspheres on the molded layer such that individual discrete sites comprise microspheres, where the microspheres comprise at least a first and a second subpopulation, where the first subpopulation comprises a first bioactive agent and the second subpopulation comprises a second bioactive agent.

In addition, the arrays can be prepared by microfabrication techniques as are known in the art. Such techniques include, but are not limited to, injection molding, hot-embossing, UV lithography, surface micromachining, photopolymerization, etching, microstereolithography and electroplating.

In addition, the shape of the sites or wells on the molded layer can be modified to alter the signal production. That is, the wells can be square, round or polygonal in shape. These surface modifications and additional surface modifications to improve signal output and/or detection are described in more detail in U.S. Ser. No. 09/651,181, filed Aug. 30, 2000 and PCT/US00/23830, filed Aug. 30, 2000, both of which are expressly incorporated herein by reference.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics. In some embodiments, silicon wafer substrates are not preferred. In one embodiment the substrate is in the shape of or is a microscope slide (see FIG. 12).

That is, in a preferred embodiment, the substrate is a microscope slide or a substrate of substantially the same dimensions as a standard microscope slide. As one of ordinary skill in the art appreciates, a microscope slide is approximately about 3" or about 7.5 cm, by about 1" or 2.5 cm by a thickness of about 0.04" or about 1 mm, although different dimensions could be used. Thus, in a preferred embodiment, the substrate of the present invention is approximately 7.5 cm by 2.5 cm by approximately 1 mm (FIG. 12). An advantage of using substrates of this size is that existing instrumentation, i.e. detectors can be used to analyze signals on the substrate. That is, existing scanning-based instrumentation including, but not limited to, that sold by General Scanning, Molecular Dynamics, Gene Machine, Genetic Microsystems, Vysis, Axon and Hewlett-Packard can be used to analyze arrays of the present invention.

The substrate will comprise one or more assay locations, i.e. the location where the assay for the detection of a target analyte will occur. A substrate that contains a first assay location can also contain a set of discrete sites into which microspheres can be located, forming an array location. A substrate that contains a first and a second assay locations can contain two sets of discrete sites which can contain microspheres and thus form two array locations. In one embodiment, the first and second assay locations are separated by a fluid barrier. When used in reference to separating assay locations, a "fluid barrier" refers to a physical or physicochemical structure or coating which prohibits or prevents flow of a liquid between a first and second assay location. In one embodiment, the assay locations are physically separated from each other; for example, a first and second assay location can have a wall physically blocking a liquid sample from flowing between first assay and second assay locations.

In some configurations, the assay locations can be separated by physico-chemical barrier coating, which acts to prohibit a sample from passing across the coating due to incompatibility of the barrier coating with the liquid. For example, a physico-chemical barrier can comprise a hydrophobic or apolar material which prohibits aqueous or polar liquids from flowing over the hydrophobic or apolar material. In another example, a physico-chemical barrier can comprise a hydrophilic or polar material which prohibits hydrophobic or apolar liquids from flowing over the hydrophilic or polar material. Typically, this physico-chemical barrier will have a low propensity to interact with the flowing liquid relative to the propensity of the assay location to interact with the flowing liquid, which assay location contains the discrete sites.

As discussed above, the assay locations, need not be limited to the configuration of a microtiter plate. That is, any separable location on a substrate serves as an assay location. By separable location is meant a location on a substrate that is physically separated from other regions on the substrate. The physical separation can be any border between assay locations. The separation can be a partition, structure or coating, or alternatively, the separation can simply be spacing between assay locations sufficient at least to distinguish one from the other. When it is desired to maintain separate solutions in each assay location, there need only be sufficient separation such that reagents delivered to one assay location will not cross contaminate another assay location. However, in some embodiments, such a physical barrier is not necessary, or in some instances, not even desired. As such, the assay locations need only be separated enough to distinguish one from the other. When partitions or borders are used between assay locations, preferred borders include but are not limited to hydrophobic regions surrounding an assay location; ridges or rims of sufficient width and height to prevent sample migration between assay locations; or troughs of sufficient width and depth to prevent sample migration between assay locations. In some embodiments, the borders are made of gaskets including, but not limited to rubber or silicon. That is, In a preferred embodiment, the border comprises a sealing mechanism to prevent leakage of the sample or reagents between wells of the substrate. As will be appreciated by those in the art, this may take on a variety of different forms. In one embodiment, there is a gasket on the substrate comprising the array, comprising sheets, tubes or strips. Alternatively, there may be a rubber or silicone strip or tube used. In one embodiment the substrate contains an indentation or channel into which the gasket fits. Furthermore, adhesives can be used to attach the gasket to the substrate. When hydrophobic regions are used to surround an assay location, the hydrophobic regions effectively contain or force the solutions to localize over the sites contained within the region surrounded by the hydrophobic region. In some embodiments the borders or partitions are made of printable materials including, but not limited to gels.

Also, in some embodiments, it is desirable to provide channels for fluid flow between wells. In this embodiment, the channels can be etched into the substrate as described herein. In an alternative embodiment, printing techniques are used for the creation of desired fluid guiding pathways; that is, patterns of printed material can permit directional fluid transport. Thus, the build-up of "ink" can serve to define a flow channel. In addition, the use of different "inks" or "pastes" can allow different portions of the pathways having different flow properties. Multi-material fluid guiding pathways can be used when it is desirable to modify retention times of reagents in fluid guiding pathways. Furthermore, printed fluid guiding pathways can also provide regions containing reagent substances, by including the reagents in the "inks" or by a subsequent printing step. See for example U.S. Pat. No. 5,795,453, herein incorporated by reference in its entirety.

In a particularly preferred embodiment fluid channels, barriers, or combinations of both are formed in the molded layer during process of forming the discrete sites in the molded layer, in accordance with the method of the invention. In this method, the channels, barriers, or combinations of both comprise the same material as the material of the molded layer.

In an alternative embodiment, the fluid barriers can be added in a step subsequent to formation of the molded layer. In this method, the fluid barrier can comprise the same material as the molded layer or any other material useful for forming a fluid barrier, and can particularly be useful when the fluid barrier comprises a physico-chemical fluid barrier.

In one embodiment, the assay locations are depressed regions in the substrate. As described herein the depressed regions, or assay locations contain discrete sites or wells.

In a preferred embodiment assay locations on the substrate are fiber optic bundles. That is, the fiber optic bundles are attached to or inserted through the substrate, as described in more detail below, to form discrete assay locations. Although not required in all embodiments, in some embodiments the fiber optic bundles are physically separated from one another by partitions that include but are not limited to those described above, e.g. hydrophobic regions, ridges or troughs. Alternatively, each fiber bundle is separated by sufficient distance to distinguish one from the other.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulable; that is, one strand generally cannot be physically separated at any point along its length from another fiber strand.

In a preferred embodiment, the assay locations comprise a plurality of discrete sites. Thus, the assay location is the same as the array location, as described herein. In this embodiment, at least one portion of the molded layer is modified to contain discrete, individual sites for later association of microspheres (or, when microspheres are not used, for the attachment of the bioactive agents). These discrete sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate.

However, it should be noted that these sites on an invention substrate may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. In a preferred embodiment, the depression in the surface of the substrate comprise depressions in the molded layer of an invention substrate that comprises a molded layer and a rigid support. In such an embodiment, the depressions in the molded layer will comprise the discrete sites of an assay location, and the depressions and discrete sites will be formed simultaneously in the method of the invention which comprises use of a template structure to form the surface of the molded layer. Also contemplated herein, depressions in the substrate may be formed using a variety of techniques generally known in the art, including, but not limited to, photolithography, stamping techniques and microetching techniques. As will be appreciated by those in the art, the technique used will depend on the composition and shape of the substrate.

In a preferred embodiment, the sites or wells are separated with spaces between each other. As is appreciated by those skilled in the relevant art, bead spacing is determined by calculating the distance between centers. Varying the spacing between sites results in the formation of arrays of high density, medium density or lower density. High density arrays are characterized as having sites separated by less than about 5 to 15 µm. Medium density arrays have sites separated by about 15 to 30 µm, while low density arrays have sites separated by greater than 30 µm. Generally, the sites are separated by less than 100 µm; preferably less than 50 µm and most preferably less than 15-20 µm. A particular advantage of spacing wells apart is that commercial scanners can be used to analyze the arrays. That is, the resolution of scanners varies and arrays can be formed that allow for detection on high or low resolution scanners. For high density arrays, high resolution scanners (<5 µm) can be employed. These scanners effectively analyze arrays with close spacing (<15 µm) between features, i.e. beads. For lower resolution scanners (>5 µm), increased bead spacing, i.e. >10 µm can be utilized, with from 15 to 20 µm being preferred. In both cases, various software packages are used, such as but not limited to, GENEPIX software package by AXON instruments or others that are provided with conventional fluorescent microscope scanning equipment. In a preferred embodiment, the software employs contrast-based or other image processing algorithms to resolve the beads and extract signal intensity information (see also U.S. Ser. No. 09/651,181, filed Aug. 30, 2000 and PCT/US00/23830, filed Aug. 30, 2000, both of which are expressly incorporated herein by reference).

While in the above described embodiment the spacing between features is accomplished by physically altering the spacing of the sites on the substrate, in an alternative embodiment, when beads in bead wells form the array, density is modulated by adding to a population of beads comprising bioactive agents, a population of beads that do not comprise a bioactive agent. That is, a population of beads with no bioactive agent, and in some embodiments no detectable signal or label, is added to at least one population of beads that does comprise a bioactive agent. The beads lacking a bioactive agent, i.e. "blank beads", dilute the concentration of beads with a bioactive agent. When applied to or distributed on a substrate, this results in increased spacing between beads with bioactive agents. That is, in the absence of blank beads, beads with bioactive agents will fill substantially all of the wells on a substrate at an average density of not more than one bead per well. When the spacing of wells is close, only high resolution scanners effectively analyze the array. However, upon the addition of a population of blank beads, blank beads will be distributed with the beads that have bioactive agents thereby increasing the distance between beads with bioactive agents. Thus, in a preferred embodiment, the distance between centers of beads with bioactive agents is at least 5 µm; more preferably between 10 to 50 µm; and most preferably between 15 to 25 µm.

In one embodiment, the ratio between beads with bioactive agents and blank beads is adjusted to achieve proper density of beads with bioactive agents on the array. The ratio depends on the desired spacing between beads. That is, when it is desired to have beads with bioactive agents n beads apart, the ratio beads with bioactive agents to blank beads is $n^2$ That is, if it is desired to have beads with bioactive agents separated by six blank beads, the ratio of beads with bioactive agents to blank beads is $1:6^2$ or 1:36. While in some embodiments it may only be necessary to include a small number of blank beads, i.e. the ratio is about 10:1 or greater, in preferred embodiments, the ratio is at least 1:36 or more, with 1:100 being particularly preferred.

In an alternative embodiment, the array comprises a first population of beads with a first bioactive agent and a second population of beads with a second population of bioactive agents. When modulating the spacing of beads on an array so that conventional scanners can be used, it is useful in this embodiment for each population of beads to be labeled or tagged with different tags. The tags are preferably detectable in distinct channels. As such, in this embodiment, only one population of beads is analyzed at a time. Accordingly, the beads that are not being analyzed serve as spacer beads although they do contain a bioactive agent and can be analyzed in a different channel. As such, the spacing of the beads from each population will be adequately spaced for analysis, while the number of beads to be analyzed is increased relative the above-described assay that uses blank beads. That is, when analyzing the first population of beads in a first channel, which does not detect the second population of beads, the second population of beads serve as spacing beads or blank beads. The second population of beads serves to increase the spacing between the first population of beads. In turn, when analyzing the second population of beads in a second channel, the first population of beads serves as spacing or "blank" beads that separate the second population of beads.

Accordingly, the present invention also includes an array as described above and a detector. In a preferred embodiment the array is in the detector. In a particularly preferred embodiment the substrate is formatted to the shape of a microscope slide and includes a molded layer containing the assay locations and array locations and at least one array location is in the detector.

In a preferred embodiment, physical alterations are made in a surface of the substrate to produce the sites. In a preferred embodiment, for example, when a first substrate contains more than one assay locations and a second substrate is a fiber optic bundle containing more than one array locations, the surface of the second substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

Figure 14B:
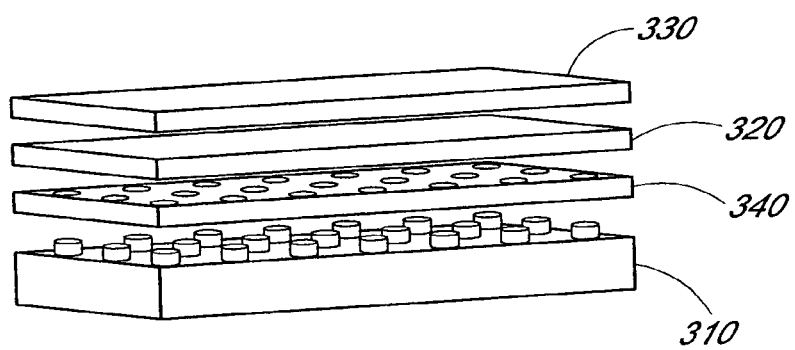
In FIG. 14B a submaster structure 310 acts as a template structure to form a molded layer 340 which can be coated with a bonding agent 320 and adhered to a rigid support 330.

The invention also provides a method for making a substrate containing one or more assay locations having discrete sites. This method is carried out by contacting a surface of a template structure with a moldable material, where the surface comprising one or more sets of projections. The moldable material is removed from the surface of the template structure, such that the removed moldable material forms a molded layer with at least a first assay location comprising discrete sites. This molded layer is adhered to a rigid support. FIG. 14B shows an example of how a template structure 310 can be used to form the molded layer 340 which can be adhered to the rigid support 330.

The method of the present invention draws from the methodology used in the replication process for forming ruled diffraction gratings. The general teachings of the formation of ruled diffraction gratings can be found, for example, in the Diffraction Grating Handbook, 4th ed. by Thermo RGL (formerly known as Richardson Grating Laboratory) available directly from Thermo RGL. Although these references will serve as general resource, it will be appreciated that the considerations for the method of forming molded layers formed in accordance with the present invention will differ from those for a method of forming ruled gratings since the principle purpose of the invention molded layers is not high precision dispersion of polychromatic light into its monochromatic components. For example, the requirement for low tolerance for flaws forming diffraction gratings (for example, to improve wavelength resolving power and reduce scattering and ghosts) will not be so stringent in the method of the invention. The important factors in forming a molded layer in accordance with the method of the invention include: forming discrete sites separated by as little as 5 μm, preferably in a pattern, where the discrete sites are each preferably depressions capable of accommodating a microsphere; forming discrete sites that are non-deformable and highly uniform; and forming the discrete sites in a manner that will permit a suitable detection system to optically interrogate discrete sites individually. Accordingly, one skilled in the art will recognize that a flaw in one or a few discrete sites will not appreciably change the effectiveness of an array of the invention.

The method of the invention includes a step of contacting a surface of a template structure with a moldable material. As used herein a "template structure" refers to a model form whose surface is used as a mold to create an inverse replica of the template structure surface. Preferably, the template structure contains one or more sets of projections on its surface. The sets of projections of the template structure will create sets of impressions in the moldable material upon contact of the template structure and the moldable material. These sets of impressions ultimately correspond to discrete sites present in a molded layer. Accordingly, a template structure that contains one or more sets of projections will be used to form a molded layer containing one or more sets of discrete sites; similarly, a template structure that contains two or more sets of projections will be used to form a molded layer containing two or more sets of discrete sites. The template structure can further contain additional projections which can create impressions in the moldable material corresponding in the molded layer to channels for the flow of fluids, including a fluid sample, along the surface of the molded layer. Further, the impressions can correspond to any other desired depressed feature on the substrate surface as discussed above. The template structure can also contain depressions on its surface. The depressions of the template structure will create projections in the moldable material upon contact of the template structure and the moldable material. These projections can ultimately correspond to, for example, physical fluid barriers present in a molded layer. Further, the projections can correspond to any other desired raised feature on the substrate surface as discussed above.

The moldable material which contacts the template structure in the method of the invention is any material that adopts and is capable of maintaining the shape of the molded layer after removing the moldable material from the surface of the template structure. The moldable material will comprise materials discussed above in describing the molded layer, including resins such as expoxides, polyimides, and the like.

In the step of contacting a surface of a template structure with a moldable material carried out in the method of the invention, the contacting can be of any form, duration and extent which results in formation of one or more sets of discrete sites in the resultant molded layer. For example, a moldable material can contact a surface of a template structure by spraying the moldable material onto the template structure, where the moldable material is a liquid in a stream, spray or mist form. Alternatively, the surface of the template structure can be dipped into a tank containing liquid moldable material, or can be pressed into a partially solidified moldable material which can be shaped to complement the surface of the template structure contacting the moldable material. In one embodiment, the template structure has a cylindrical shape, and the template structure is contacted with a moldable material, the moldable material is permitted to solidify until the shape of the moldable material is capable of remaining unchanged, and then the moldable material is unrolled from the cylinder as a molded layer. In a preferred embodiment, when the template structure is cylindrical, the method of contacting the template structure is a continuous process in which at a first portion of the cylinder, the cylinder is contacted with a moldable material and at a second portion of the cylinder, solidified moldable material is removed from the cylinder as a molded layer.

A template structure can be either a master structure or a submaster structure. A "master structure", as used herein, refers to the original mold formed by a process other than the molding method of the invention. One skilled in the art will recognize that a variety of methods can be used for forming the master structure, including, but not limited to physical etching (e.g., diamond etching), photoresist etching, or any other method capable of forming a detailed design on a substance useful as a template structure in the method of the invention. In addition to use of a master structure in the method of the invention as a template structure, a submaster structure can also be used as a template structure in the method of the invention. As used herein, a "submaster structure" refers to a template structure that has been formed according to the method of the invention or in a similar molding process such that the design of the template structure originates from a separate, master structure. A submaster structure can be formed directly using a master structure as the template structure in a method such as the method of the invention. Additionally, a second submaster structure can be formed from using a first submaster structure as the template structure in a method such as the method of the invention. A submaster structure formed from a master structure is referred to as a first generation submaster structure. A submaster structure formed from a first generation submaster structure is referred to as a second generation submaster structure.

It is within the scope of the present invention that a template structure can be a submaster structure from any of a large number of generations. One skilled in the art will appreciate that the number of submaster generations available for use as template structures in the method of the invention will correspond to the degree to which the original design of the master structure is maintained from generation to generation. While some elements of the original design of the master structure can be lost, damaged or distorted between generations, it will be recognized that only those elements that are important to the desired use of the invention substrate array composition will be considered in determining the value of a submaster generation or a particular submaster structure as a template structure in the method of the invention. Such elements include, but are not limited to: formation of discrete sites separated by as little as 5 µm, preferably in a pattern, where the discrete sites are each preferably depressions capable of accommodating a microsphere having a diameter that varies from about 0.5 µm to about 50 µm, preferably from about 1 µm to about 5 µm; and forming the discrete sites in a manner that will permit a suitable detection system to optically interrogate discrete sites individually. Although the number of generations for which submasters are useful can be very large, such as 50, typically submaster structures used as template structures in the method of the invention will be 20 generation submaster structures or less, preferably 10 generations or less, more preferably 6 generations or less.

Figure 15:
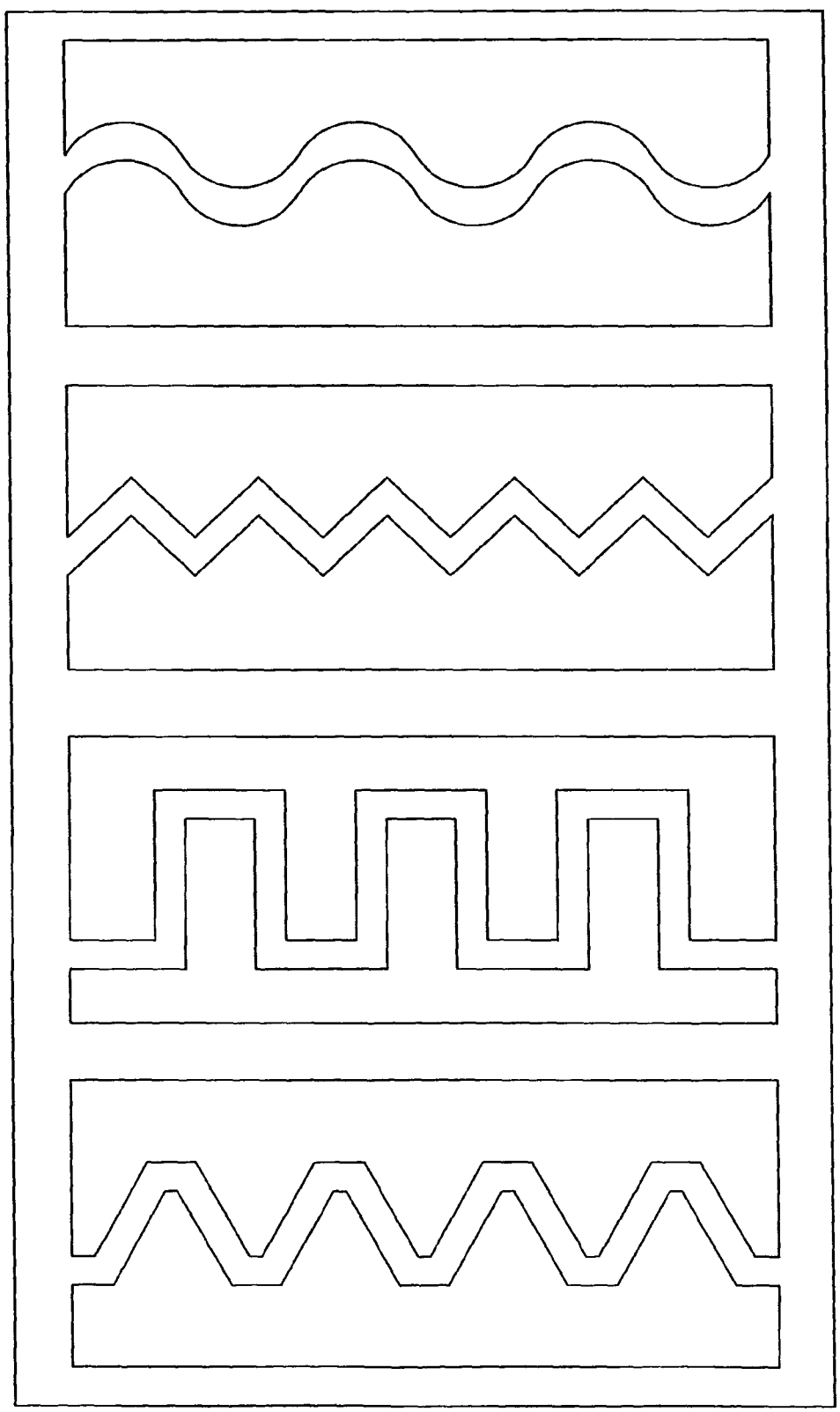
FIG. 15 depicts a series of configurations in which the template structure can be either an even or odd generation submaster structure.
Figure 16A:
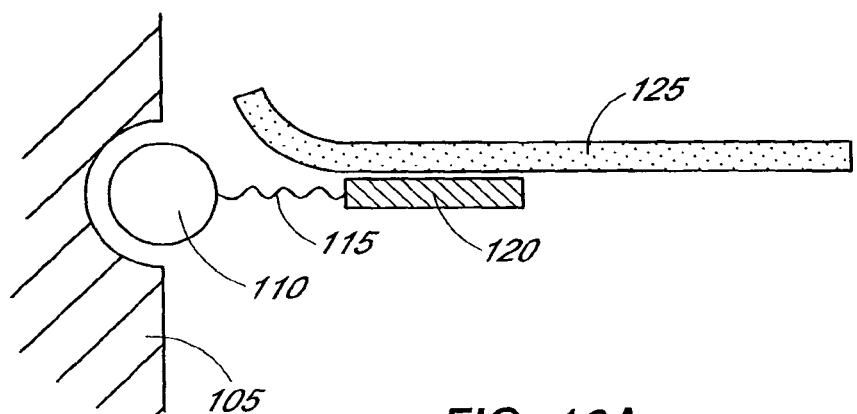
FIGS. 16A, 16B and 16C depict three different embodiments for attaching a target sequence to an array. The solid support 105 has microsphere 110 with capture probe 120 linked via a linker 115.
Figure 16B:
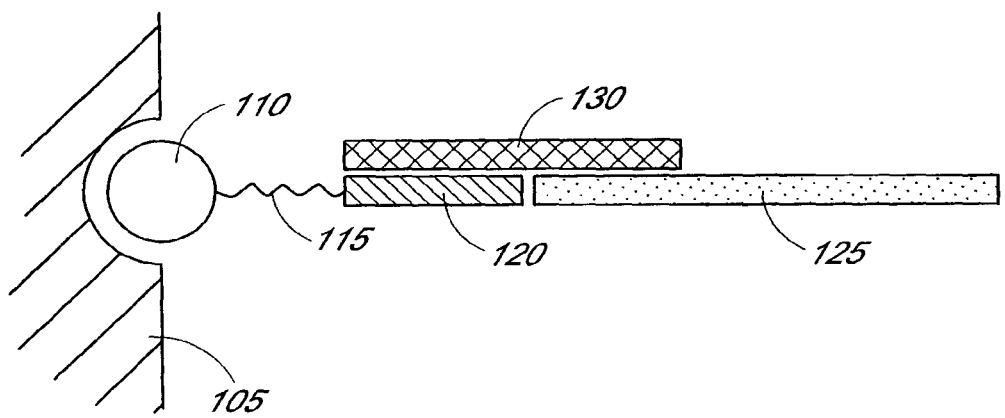
Figure 16C:
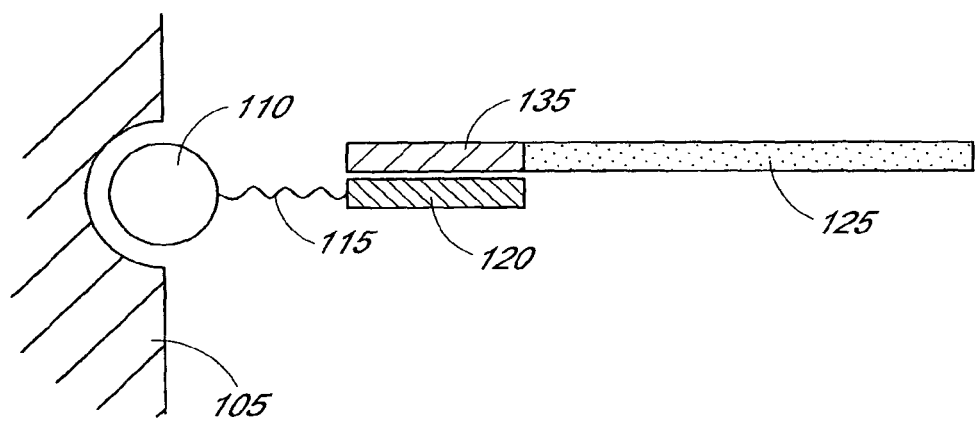

One skilled in the art will appreciate that by using a submaster to create multiple submasters in the next generation, a large number of multi-generation submasters can be formed. For example, if a submaster of each generation is used to form 10 submasters of the next generation and 6 generations of submasters are formed, more than 1 million submasters will result. Accordingly, formation of the template structure used in the method of the invention will typically occur by forming a multiple-generation submaster structure, according to the number of desired template structures and the capability of forming multi-generation submaster structures. One skilled in the art will also appreciate that each odd-numbered submaster generation (first generation, third generation, fifth generation, etc.) will have the inverse form of the original design of the master structure, and each even-numbered submaster generation (second generation, fourth generation, etc.) will have a replica of the original design of the master structure. When the master structure represents the desired design of the molded layer formed using the method of the invention, one skilled in the art will know that odd-numbered submaster generations are to be used as the template structure in the method of the invention (see, for example FIG. 14). Similarly, when the master structure represents the inverse design of the desired design of the molded layer formed using the method of the invention, even-numbered submaster generations are to be used as the template structure in the method of the invention. When the when either the actual design or the inverse design can be the desired design of the molded layer, for example, when the design of the master structure is substantially equivalent to the inverse design of the master structure (for example, an egg-crate design or equivalent, see FIG. 15), one skilled in the art will recognize that all generations of submaster structure can be used as template structures in the method of the invention.

In a preferred embodiment, prior to the step of contacting the surface of the template structure with a moldable material, a releasing agent is applied to the surface of the template structure. As used herein a "releasing agent" is any compound, composition, or other substance, which aids in the separation of the moldable material from the surface of the template structure in forming a molded layer. Useful releasing agents include silicone oil, polyvinyl alcohol, fluorinated silane or other known releasing agent. Selection of the type and amount of a releasing agent will depend on several easily determinable factors such as the strength of the template structure and of the moldable material, the environmental conditions of the contacting and molding process, the degree of tolerance for distortions or imperfections in the molded layer, and the like.

In another preferred embodiment, a molded layer actually contains two or more layers. This embodiment will find particular utility when it is desirable for a molded layer to possess particular chemical or physical properties. In this instance, the molded layer contains at least one layer that provides and maintains the shape of the molded layer (the "shape layer") and at least one layer that provides the desired properties on the surface of the molded layer (the "active layer"). The shape layer will comprise materials discussed above, and include resins such as expoxides, polyimides, and the like. The active layer can provide chemical properties such as permitting a bioactive agent or other molecule to be chemically bound thereto, or physical properties such as affinity for particular fluids, desired optical properties, and the like. The active layer can also be selected to have properties for favorable interaction with sample-containing solvents or for favorable wetability properties, as described above. The active layer can also serve as a protective layer to prevent the underlying shape layer from degradation as a result of, for example, irradiation, fluid contact, oxidation, and the like. In another embodiment, the active layer can be selected according to desired optical properties, such as a reflective layer, which can be employed to enhance signal collection from the arrays. Such a reflective layer can be formed from, for example, a metal layer such as a layer of silver, aluminum or chromium. Exemplary active layers include, but are not limited to, glass, quartz, fused silica, magnesium fluoride, and the like.

The active layer can, but need not, contribute to maintaining the shape of the molded layer; accordingly, the active layer can quite thin (i.e., <1 µm), though typically the active layer will be about 0.1 µm. The shape layer is typically thicker than the active layer, having any thickness sufficient to insure that the shape layer maintains the shape of the molded layer. This thickness of the shape layer will usually be at least about 10 µm in thickness and can be 1 µm or more in thickness. Typically, the shape layer will range from about 50 µm to about 500 µm in thickness.

In another embodiment, the active layer can itself comprise two layers, three layers, or more. For example, an active layer can comprise a layer having desired optical properties such as reflectance, and an overlying layer which serves as a protective layer to prevent the underlying optical active layer from degradation. Any of a number of multiple active layer combinations can be used in the present invention, as will be apparent to one skilled in the art. For example, the active layer can comprise a reflective layer such as a silver, aluminum or chromium layer, and further comprise an overlying layer that prevents the underlying optical layer from degradation.

The method of the invention also includes a step of removing the moldable material from the surface of the template structure to form a molded layer, where the molded layer has at least one assay location having discrete sites. At some point which can occur before or after removing the moldable material from the surface of the template structure, the moldable material will transition to a state in which the shape of the moldable material is substantially unchanged; transition to this state represents the formation of the molded layer. A moldable material having a shape that is substantially unchanged refers to a state of the moldable material where its shape does not change in such a way as to alter the intended properties of the resultant molded layer; for example, the size or shape of the discrete sites is not changed in such a way that the changes intended properties of accommodating a microsphere, or transmitting or reflecting luminescence, or the like. Generally, the step of removing the moldable material from the surface of the template structure will be carried out in such a way as to permit the moldable material to maintain a shape that is fully complementary to the template structure, and thus, the moldable material is removed from the surface of the template structure in the form of the molded layer.

In another embodiment, the molded material will undergo a change of shape after removal from the template structure. This can be, for example, a rounding or smoothing of features formed in the moldable material that are complementary to the projections of the template structure, which can result in improved microsphere interaction properties, improved optical properties, or other desired property.

Once the features (i.e., discrete sites, fluid barriers, fluid channels, and the like) formed in the molded material are substantially unchanged, the moldable material is then termed the molded layer. Although the molded layer is characterized as having substantially unchanged features, it will be understood that the molded layer is not required to be rigid or retain structural memory beyond that of maintaining the shape of the features. For example, in one embodiment of the invention, a molded layer can be a flexible film containing discrete sites. Such a flexible film can be stored in a compact form, such as in rolled form on a spool, as stacked sheets, or any other configuration for convenient storage. A substrate containing one or more assay locations having discrete sites is formed in accordance with the invention by adhering this flexible molded layer to a rigid structure, as will be further discussed below.

The moldable material or a molded layer in flexible form, can comprise a substance that can be subjected to a hardening step to decrease the deformability of the moldable material or molded layer. The hardening step can be carried out using any of a variety of substances known to be useful for hardening including: heat treatment; radiation treatment using radiation such as UV radiation, particle beam radiation; chemical treatment using an oxidative substance or other chemically reactive substance; and the like. The hardening step can be carried out to any extent desired to convey to the moldable material or molded layer the desired structural properties, including carried out to completion where the resultant molded layer is inflexible. In one embodiment of the invention, the hardening step is carried out prior to the step of removing the moldable material from the surface of the template structure. In another embodiment, the hardening step is carried out after adhering the molded layer to the rigid support.

The molded layer formed in accordance with the method of the invention is adhered to a rigid support. As discussed above, a rigid support is a structural component of a substrate that causes a substrate to be inflexible or to retain structural memory. By adhering the molded layer to the rigid support, the molded layer can retain a shape that is optically interrogatable. The step of adhering the molded layer to the rigid support is carried out by contacting the molded layer directly to the rigid support or by coating either the molded layer or the rigid support with a bonding agent and then contacting the molded layer/bonding agent to the rigid support or rigid support/bonding agent to the molded layer. The result of the adhering step will be to cause the molded layer to be attached to the rigid support, preferably such that it does not rotate, bubble, warp, curl, tear, or otherwise deform in a manner which adversely influences the ability to optically interrogate the discrete sites or which adversely influences the flow of fluids over the molded layer and selected assay locations therein. In a preferred embodiment, the moldable layer is adhered to the rigid support by directly contacting the molded layer to the rigid support.

A bonding agent useful in the adhering step of the method of the invention can be any substance that is capable of securing the attachment of the molded layer to the rigid support without adversely influencing the ability to optically interrogate the discrete sites and which does not cause the adverse degradation of the rigid support or the molded layer. When a bonding agent is used, it will preferably form a thin, even coating (about 1 µm in thickness) between the molded layer and the rigid support. Alternatively, only portions of either the rigid support or the molded layer are coated with the bonding agent. For example, the bonding agent can be placed only in portions of either the rigid support or the molded layer, or both, such that the bonding agent does not lie in a position that will cause excitory radiation or a detectable signal to pass through the bonding agent during the optical interrogation of the discrete sites. Such an example includes placement of the bonding agent in locations on the rigid support or moldable layer, or both, that do not lie directly beneath the discrete sites of the molded layer. In such an instance, a bonding agent need not be limited to a substance that does not influence the optical interrogation of the discrete sites. In another example, the bonding agent can be placed in a variety of partially-coating configurations, such as serpentine, concentric circles or ovals, spiral, and the like.

As will be appreciated by one skilled in the art, when the molded layer is coated with the bonding agent, the back surface of the molded layer will be coated; that is, the surface coated with the bonding agent is the surface of the molded layer not containing the formed features such as discrete sites, fluid barriers, fluid channels, and the like. Suitable bonding agents include, but are not limited to, liquid epoxies; glues or adhesives that are added to either the molded layer or the rigid support; sheets of epoxies; rolls of epoxy tape, glues or adhesives in gel form or attached to a solid support; solvents which dissolve a small portion of the surface of the rigid support or molded layer and result in adherence of the molded layer to the rigid support upon evacuation of the solvent; compounds which become permanently adhesive upon heat setting, photo-setting, UV setting, and the like; and any other adhesive substance known in the art.

In another embodiment, the surface of the substrate is modified to contain modified sites, particularly chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites.

In addition, biologically modified sites may be used to attach beads to the substrate. For example, binding ligand pairs as are generally described herein may be used; one partner is on the bead and the other is on the substrate. Particularly preferred in this embodiment are complementary nucleic acid strands and antigen/antibody pairs.

Furthermore, the use of biological moieties in this manner allows the creation of composite arrays as well. This is analogous to the system depicted in FIG. 1F, except that the substrate 10 is missing. In this embodiment, populations of beads comprise a single binding partner, and subpopulations of this population have different bioactive agents. By using different populations with different binding partners, and a substrate comprising different assay or array locations with spatially separated binding partners, a composite array can be generated. This embodiment also a reuse of codes, as generally described below, as each separate array of the composite array may use the same codes.

As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

As noted above, arrays of the present invention and in particular, arrays of the one-component system are formed by altering the surface of a substrate so that it contains discrete sites or wells. Preferably the wells are formed to contain not more than one microsphere as described herein. As noted herein, in a one-component system, in a preferred embodiment the assay locations (which also form the array locations in the one-component system) are formed in the molded layer. As such, in an alternative embodiment, the invention provides improved methods for making arrays comprising a molded layer formed using a template structure.

In another preferred embodiment the assay locations are fiber optic bundles. As such, in a related alternative embodiment, the invention provides improved methods for making arrays comprising a segment of a fiber optic bundle on at least one discrete site on an array.

In general in this embodiment, at least one, but generally a plurality of fiber optic bundles is attached to or inserted through the planar substrate to form the array of arrays on a planar substrate. When the fiber optic bundle is attached to the substrate, the method includes providing a fiber optic bundle of length L, wherein L can in theory be any length, and cutting the bundle, by methods as are known in the art such as, but not limited to the use of a diamond saw or water jets, to form a plurality of small fiber optic bundle segments. The segments are then attached to the array by methods that include, but are not limited to placing the segments in a pre-formed well sized to accommodate the bundle segments attaching with adhesives, or melting the substrate such that the fiber optic bundle is embedded into the substrate.

In an alternative embodiment, the method includes inserting at least one fiber optic bundle through a block of substrate material such as plastic or ceramic and then cutting the substrate including the bundle, to the desired thickness (see FIG. 13). As such, a cross-sectional portion of the fiber bundle is framed by the substrate material. Generally, at least a first and a second bundle will be inserted into the substrate material. Generally, the bundles will be in an array format as described herein. As one of skill in the art appreciates, this method markedly facilitates the production of a large number of uniform array of arrays. That is, in theory, there is no upper limit to the length of the fiber bundle or thickness. As such, very long bundles can be inserted into very thick substrate blocks, i.e. up to or even thicker than 1 meter. For example, when one considers that the typical thickness of the substrate of an array is less than about 0.5 cm, a 1 m block (into which a potentially 1 m bundle is inserted) results in the formation of at least about 200 uniform array of arrays.

In this method, the fiber bundle(s) is inserted into the substrate substantially perpendicularly to the plane of the surface of the block. Generally, the substrate is drilled or machined to form an orifice into which the bundle is inserted. In some embodiments, the orifice is lined with a sealant or gasket which surrounds the bundle. Alternatively, a sealant or epoxy is applied to the substrate surrounding the bundles after the block is cut to form the plurality of substrates. In some embodiments this is advantageous as the sealant may not only prevent leaks of any assay solutions or beads through the substrate around the bundle, but also the sealant forms a barrier around the bundle that isolates a bundle from the other bundles. That is, once the arrays are formed, a substance is applied to the surface of the substrate surrounding at least a first fiber optic bundle; the substance not only anchors the fiber bundle in place, but forms a partition separating the different fiber bundles. In some embodiments the substance, i.e. epoxy, does not form a partition, but rather holds the fiber bundle in place.

In an alternative embodiment a fiber optic bundle is placed into a liquid or molten solution of a substance that will be the substrate. That is, in this embodiment, the substrate is made from a meltable material such as, but not limited to plastic or wax. In a preferred embodiment the substrate is made from thermosetting or thermoplastic polymers. In one embodiment, at least one fiber optic bundle is retained by one end by a holder and immersed into the molten substrate solution.

The use of a molten substrate finds a number of uses in forming the substrate of the array. A particular advantage is the ability to add substances to the molten solution that will be incorporated into the substrate once hardened. That is, substances can be added to modify properties of the substrate such as rendering it reflective or opaque. In a particularly preferred embodiment carbon black is added to the liquid substrate substance. The addition of carbon black causes the resulting substrate to be opaque.

It is understood that container may take any shape, and that a heating mechanism may be implemented in a variety of fashions. However it is the function of container and heating mechanism to create and retain a bath of molten substrate into which at least those portions of the array of bundles projecting from temporary holder may be immersed or submerged. In a preferred embodiment the container is of the same dimensions as a microscope slide such that the resulting substrate is the same size as a microscope slide.

The molten substrate will fill the space between individual bundles. The heat source is turned off and the substrate is allowed to harden, and the temporary holder is removed. Bundles are embedded within the substrate, for at least a fraction of the length L of the bundles. The substrate is then cut as described above to form a plurality of substrates containing fiber bundles.

In some embodiments, the exposed ends of the bundles are machined or processed, typically by lapping and polishing to planarize the surface of the ends. Concave well regions may be formed in the surface of exposed ends of each strand, and a bead deposited in each well, or into a substantial number of the wells, as described herein.

Note that the individual bundles are retained in tight registration with each other by the solidified substrate. The longitudinal axis of each bundle will remain substantially parallel to each other, and substantially perpendicular to the plane of the top surface of substrate.

In one embodiment an advantage of the substrate is that individual bundles may be removed and replaced, if necessary. For example, one or more bundles might become damaged. Rather than discard the entire array, when a meltable substrate like wax is used, the damaged bundles may be removed by heating the substrate surrounding the bundles in question. For example, a thin walled hollow tube, whose inner diameter exceeds the outer diameter D of a the bundle to be removed, can be heated and pushed into and through the wax probe, to surround the bundle in question. This localized heating enables the damaged bundle to be removed and replaced with a new or different bundle, around which molten wax can then be deposited to retain the replacement bundle within the substrate.

In a preferred embodiment, the invention also includes a substrate holder. The substrate holder is a device into which the substrate fits. The holder allows for easy handling of the array. In addition, the holder provides rigidity to prevent warping of the substrate/array. While the holder can be formed from any rigid substance, in a preferred embodiment the holder is metal.

In a preferred embodiment the holder comprises a metal frame that surrounds each edge of the substrate, i.e. the microscope slide array. In some embodiments the holder comprises a lid that optionally includes hinges to allow for opening and closing of the lid. A hinged lid as such facilitates insertion and removal of the array from the holder. While the lid can be made of any material, it is preferably a translucent material that allows for detection of signals from the array.

In an alternative embodiment the holder further comprises a base to which the frame is attached. The base may be any rigid material, but in a preferred embodiment is translucent. Alternatively the base is metal. What is important is that the holder remain rigid and prevent the substrate from warping.

As will be appreciated by those in the art, there are a number of possible configurations of the system, as generally depicted in the Figures. In addition to the standard formats described herein, a variety of other formats may be used. For example, as shown in FIGS. 1C-1F, "pieces" of substrates may be used, that are not connected to one another. Again, these may be the same arrays or different arrays. These pieces may be made individually, or they may be made as a large unit on a single substrate and then the substrate is cut or separated into different individual substrates. Thus, for example, FIGS. 1C and 1D depict a plurality of bead arrays that are added to the wells of the second substrate; FIG. 1C is a "bead of beads" that is configured to maximize mixing. FIG. 1D utilizes a plurality of planar first substrates; as will be appreciated by those in the art, these may or may not be attached to the second substrate. In one embodiment, no particular attachment means are used; alternatively, a variety of attachment techniques are used. For example, as outlined for attachment of beads to substrates, covalent or non-covalent forces may be used, including the use of adhesives, chemistry, hydrophobic/hydrophilic interactions, etc. In addition, the substrate may be magnetic and held in place (and optionally mixed) magnetically as well. Thus, for example, as depicted in FIG. 1F, binding moieties can be used; these can be covalent linkages or non-covalent linkages. They may be used simply for attachment, or for targeting the first substrate arrays to particular locations in or on the second substrate. Thus, for example, different oligonucleotides may be used to target and attach the first substrate to the second.

In a preferred embodiment, there are optical properties built into the substrate used for imaging. Thus, for example, "lensing" capabilities may be built into the substrate, either in a one component or two component system. For example, in a one component system, the portion below of one or more of the assay locations, either within the molded layer or within the rigid support, may have unique or special optical components, such as lenses, filters, etc.

In addition, preferred embodiments utilize configurations that facilitate mixing of the assay reaction. For example, preferred embodiments utilize two component systems that allow mixing. That is, in some embodiments, the arrays project from the block and can be used as a "stick" that stirs the reaction to facilitate good mixing of the assay components, increase the kinetics of the reaction, etc. As will be appreciated by those in the art, this may be accomplished in a variety of ways. In a preferred embodiment, the first and second substrates are configured such that they can be moved relative to one another, either in the X-Y coordinate plane, the X-Z coordinate plane, the Y-Z coordinate plane, or in three dimensions (X-Y-Z). Preferred embodiments utilize a block jig that allows the block to move freely in either the plane of the plate or orthogonal to it. This is particularly useful when the reaction volumes are small, since standard mixing conditions frequently do not work well in these situations.

In addition to this, or in place of it, there may be additional mixing components as part of the system. For example, there may be exogeneous mixing particles added; one embodiment for example utilizes magnetic particles, with a magnet that is moved to force mixing; for example small magnetic mixing bars and magnetic stir plates may be used.

Alternatively, mixing in either one or two component systems can be accomplished by sealing the system and shaking it using standard techniques, optionally using mixing particles.

In a preferred embodiment, the system is configured to reduce evaporation and facilitate small sample size and handling. That is, the system is closed or sealed by enclosing a defined space to maintain control over the small sample volumes. In this regard the invention provides a hybridization chamber that encompasses or encloses the array and/or sample. As is more fully outlined below, preferred embodiments utilize the hybridization chambers comprising a base plate and alignment moieties that find particular use in the two-component system, although they also find use in the one-component system.

One advantage of the enclosed system is that it reduces or dampens vibration. That is, because of the small sample volume, the arrays may be susceptible to disturbances caused by vibration, for example, by platform shaking, motor vibration, or air circulation. By enclosing the array, and placing the array on the base plate, the samples and arrays are less susceptible to disturbances caused by vibration as the base plate dampens the vibration.

An additional advantage of this aspect of the invention is that the enclosed array allows for the use of increasingly small volumes. In an open array format, small sample volumes may evaporate resulting in a variety of problems including sample variation, alteration and inconsistent concentration of solutes in the solution. For example, when small sample volumes are present in different assay locations, differential evaporation of the solution may result in dramatically altered solute concentration. Such differences may alter hybridization kinetics, for example, and make it difficult to interpret and compare results obtained from such open arrays. However, by enclosing the array, for example in the hybridization chamber outlined herein, such sample variance is minimized thereby rendering the data obtained from the enclosed array more reliable. Accordingly, any of the methods described herein, find use with the hybridization chamber.

Also, the enclosed array allows for prolonged assay/incubation times relative to incubation times in an open array. Again, the sealed or enclosed array prevents sample evaporation, allowing for prolonged incubation periods.

In addition, the enclosed array facilitates mixing of the sample, when necessary. In general, when using small sample volumes, adequate mixing of the sample may be difficult to achieve. However, as is more fully outlined below, in one embodiment the hybridization chamber facilitates mixing when flexible membranes are used with a pneumatic device that provides vacuum and/or pressure.

When a "two-component" system is used, a hybridization chamber may be used. That is, both of the components i.e. the substrate comprising a plurality of assay locations and the substrate comprising a plurality of array locations, are enclosed within the hybridization chamber. In a preferred embodiment, these components include but are not limited to a fiber optic array and a multi-well microtiter plate that are enclosed in the hybridization chamber.

In a preferred embodiment the hybridization chamber contains a base plate upon which or into which one of the components is placed. By base plate is meant any platform or holder onto which one of the array components is placed. The base plate may be made of any material including plastic, glass or metal or any materials outlined herein for substrates; when the base plate is metal, it is preferably made of aluminum. Aluminum provides for a light weight yet durable base plate. In addition, aluminum allows for efficient and/or rapid heat transfer to the chamber. However, when the base plate is made of plastic or glass, the component is directly contacted with the base plate. Alternatively, metal sheets or templates may be inserted into or placed on the base plate. The metal sheets or templates can be designed to hold any of a variety of shapes to accommodate a variety of component sizes and/or shapes. As previously described, metal offers the advantage of being a rapid and efficient heat conductor.

In one embodiment the base plate contains at least one depression or base cavity into which the array component is placed. That is, when a microtiter plate is the component, for example, the depression or base cavity is formed such that the microtiter plate is placed directly into it and preferably fits tightly to avoid extra vibration and allow efficient heat transfer. The depression may be molded into the base plate. In addition, the base plate may contain multiple depressions or cavities such that multiple separate array components are placed on a single base plate. Alternatively, the base plate may be flat, and preferably comprise hooks or other attachment moieties to keep the arrays in place.

In addition preferred embodiments utilize a lid with the hybridization chamber. The lid can be made of any material (again, as listed for substrates herein), but glass, plastics or metal is preferred. The lid is preferably matched to the base plate such that when the lid is placed on the base plate, a closed chamber is formed.

In another embodiment the lid comprises at least one component placement port. By component placement port is meant a site in the lid to which a component is immobilized. That is, the placement port allows for attachment of one of the components to the lid. In a preferred embodiment, the port is a hole in the lid through which the component is inserted. For example, when a fiber optic bundle is the component, the bundle is inserted through the port. In this embodiment, the port additionally comprises a sealant surrounding the attachment site, such that an airtight seal is formed between the component, i.e. the distal end of the fiber optic bundle, and the lid. This sealant may be any material including silicon, rubber, plastic, etc., as outlined below. Alternatively, the seal may be a gel-based substance such as petroleum jelly, or a film based substance such as PARAFILM.

In an additional embodiment, the lid comprises a plurality of ports in the lid. That is, when multiple components are to be used, it is necessary to have a separate port for each component. For example, when multiple fiber optic bundles are used, each fiber optic bundle is placed in a separate port. However, although it is possible for each fiber optic bundle to be inserted into one port at a time, it is also possible for the same fiber optic bundle to be inserted into different ports successively. That is, there is nothing to limit the number of ports into which a component is inserted successively. For example, as shown in FIG. 7A the lid 80 contains multiple ports 82 into which fiber optic bundles 84 are placed. The lid is then placed onto a microtiter plate 86 in the base cavity 88 of the base plate 90. A base plate 90 is depicted in FIG. 7B and shows the base plate 90 and base cavity 88.

In a preferred embodiment, the port seal reduces or prevents solution cross contamination. That is, the seal surrounding the individual port/component forms a seal against the base plate or array component such that the solution from the sample corresponding to a particular port/component is separated or sealed from the other components.

In an alternative embodiment, not all ports are filled with components at all times. When it is appropriate or desired to have less than maximal filling of the ports, plugs can be inserted into the ports that do not contain components. In this manner, the lid still forms an airtight seal with the base plate, despite the presence of ports without components. The plugs can be in the form of a rubber stopper, a gasket, a film, a gel and the like.

In a preferred embodiment around the periphery of the chamber between the lid and base plate resides a sealant. The sealant may be of any material that results in an airtight seal being formed between the lid and base plate. In a preferred embodiment, the sealant is formed of rubber, such as a rubber or silicon gasket or O-ring 94 (see FIG. 8). The sealant may be fixed to either the lid or baseplate. To this end, the sealant may be permanently affixed to the lid or baseplate. Alternatively, the sealant may fit into a groove in either the lid or base plate. As such, the sealant is immobilized to the lid or base plate, but the immobilization is not necessarily permanent. Alternatively, the sealant may be formed from a liquid sealant such as petroleum jelly or from a pliable film material such as PARAFILM or other waxes.

In a preferred embodiment, when a two-component system is used, the hybridization chamber further comprises alignment moieties. By alignment moieties is meant a feature of the chamber that facilitates alignment of the lid with the base plate. The importance of the alignment moieties resides not only in the alignment of a single lid and base plate, but also reproducible alignment of multiple lids and base plates. That is, the alignment moieties facilitate the physical alignment between any array components and any multiple well microtiter plate configuration. When fiber optic bundles in the lid are to be aligned with a microtiter plate on the base plate, the alignment moieties allow for alignment of the vertical center axis of the fiber bundle with their corresponding well center axis. In a preferred embodiment, alignment is such that all fiber bundles clear, i.e. do not touch, the inner walls of the wells. This alignment may be important for sequential imaging.

In another embodiment, the alignment moieties facilitate the physical alignment between any array components and a detection instrument, such as a microscope.

In one embodiment the alignment moiety is a complementary male/female fitting. The male fitting may be affixed to the lid or base plate, although it need not be permanently affixed. When a male fitting is used as an alignment moiety in either the base plate or lid of the chamber, it is preferable that the opposite chamber piece contain a slot or hole (female fitting) into which the male fitting is inserted. One of ordinary skill in the art appreciates the variations of this male/female fitting that find use with the invention. In this regard, the features may be indexer pins or bumps on one chamber piece and holes or complementary grooves on the other piece.

In a preferred embodiment, fiducials are used; see U.S. Ser. Nos. 60/119,323, and 09/500,555 and PCT/US00/03375, hereby incorporated by reference in their entirety.

In an alternative embodiment, the chamber may also contain clamp features to maintain secure contact between the lid and base plate. The advantage of clamping is to distribute uniform loading throughout the chamber to accomplish uniform seal compression. By "clamp features" or "clamps" is meant any feature that allows for the application and maintenance of increased pressure or a seal between the lid and base plate. In one embodiment, the clamp feature includes a rotating stud/receptacle mechanism. That is, a stud 96 is inserted into a receptacle 98 and rotated to depress the lid and base plate together (see FIG. 8). Alternatively, the mechanism may include a hook and latch mechanism. One of ordinary skill in the art appreciates the number of clamping mechanisms that find use with the invention. In addition, one of ordinary skill in the art appreciates that the method of clamping is not limited to manual clamping. As such, it may also be automated.

In an alternative embodiment, the chamber includes features around the periphery for handling the chamber. In a preferred embodiment the features are slots that are wide enough to permit a users fingers to manually handle the chamber/array. In an alternative embodiment, the features are slots, grooves, handles and the like and may find particular use in automatic or robotic movement of the chambers. These additional features may also be distributed asymmetrically to facilitate robotic handling.

As described above, an advantage of the hybridization chamber is that small sample volumes can be used without the loss of sample solution. In a further embodiment, the chamber may contain one or more reservoirs to hold additional solutions. As such, the hybridization chamber also functions as a humidity chamber. The inclusion of additional solution in the reservoir further prevents evaporation of sample.

In an alternative embodiment, for example when no microtiter plate is used, the sample may be applied to a membrane that is on the surface of a base plate. Advantages of using the membrane include ease of cleaning or even disposing of the membrane after each use and the flexible membrane will not damage pipette tips or fiber optic tips due to contacting the tips with the bottom of the sample well.

In this embodiment, the base plate contains a series of small openings 102, for example in microplate format (FIG. 9A). Thus, the membrane is depressed into the openings forming separate assay locations. A variety of membranes are useful with the invention. What is important is that the membrane is flexible. In some embodiments it may be desired to have a chemically inert membrane, while in some embodiments it may be desirable to have a membrane to which assay components will interact, for example nylon, nitrocellulose membranes and the like.

In a preferred embodiment, channels connect each of the openings (FIG. 9B). The channels 100 may connect to a pneumatic device that produces vacuum and/or pressure.

Thus, when vacuum is applied, the membrane deforms into the openings 102 to form small pockets or wells. The sample can then be applied to the pockets. By applying different amounts of vacuum to the membrane through the openings, the volume of the well formed by the deformed membrane and fluid height can be changed. Furthermore, applying intermittent vacuum to the membrane through the channel can also agitate or mix the liquid in the wells. Such a mixing method is advantageous because the entire system does not have to be vibrated and stir bars or tumblers are not required. Furthermore, when subsets of openings are connected to different channels, different subsets can be mixed independently in the same base plate.

When positive pressure is applied, the membrane deforms up or stays flat depending on the magnitude of the pressure, whether there is a load on top of the membrane and the size and shape of the opening. This has significant advantages particularly in washing or cleaning of the chamber.

When pressure and vacuum are applied to different ports in certain sequences, small amounts of solutions can be made to migrate to different portions of the membrane. That is, as shown in FIG. 10A-F, differential application of pressure and vacuum results in a membrane that is elevated in some places and depressed in other places. Thus, a solution that is applied to the membrane will migrate to the lower sections of the membrane. This has the advantage of allowing incubations of a sample on the membrane to proceed for precise times. That is following the particular time, vacuum can be released and if necessary pressure applied to remove the solution. This will allow the incubation in small sections to achieve uniform incubation time between the first and last wells across an array.

Advantages of regulating sample volume through the application of vacuum or pressure, include reducing consumption volume of reagents, such as hybridization solutions; increasing the ease of mixing small sample volumes and increasing the ease of cleaning the membrane.

In a preferred embodiment the channels connect to common fluid handling devices to pump in or suck out sample solutions such as hybridization mixtures or wash fluids. Again, in one embodiment all openings are connected to a single channel. As such, all wells are treated with the same solution. Alternatively, subpopulations of openings are connected to different channels allowing for differential application of solutions to the subpopulations.

When the channels are connected to fluid handling devices, it will be necessary to include a feature for the application and removal of the liquid from the sample. That is, for liquid to be added and removed through the opening in the base plate, the membrane must be penetrated to allow the fluid to be moved. In this regard, a needle, for example, is useful for puncturing the membrane to apply and remove the fluid. When needles are used, it may be necessary to use a resealable membrane, or apply a sealant to the puncture location to prevent undesired leakage of the solution.

In some embodiments the chamber includes heat transfer features. That is, when elevated temperatures are required or desired, the chamber is designed to maintain elevated temperatures. In one embodiment, this includes the application of an insulating material to the chamber. Then, when prewarmed solution is introduced into the chamber, the elevated temperature is maintained. That is, the solution can be easily heated outside of the chamber prior to being pumped into the chamber. The simple chamber geometry will facilitate the maintenance of equal temperatures between liquid in different wells.

In an alternative embodiment, the chamber includes a heating mechanism to maintain the elevated temperature in the chamber. In one embodiment, the chamber is heated uniformly by the heating apparatus. In an alternative embodiment, the heating apparatus heats different sections of the chamber independently.

As described above, the use of metal such as aluminum on the base plate facilitates heat transfer because the metal is a fast and efficient conductor of heat.

When a "one-component" system is used, a lid and a sealing mechanism can be used. That is, as described above, the lid forms an airtight seal with the base plate. Thus, like the lid above, the lid of the "one-component" system also includes a sealant between the lid and base plate. In one embodiment, the lid and base plate also include alignment moieties as described above for the "two-component" system. Alternatively, in one embodiment the chamber of the one-component system does not include alignment moieties. In this respect, the necessity for stringent alignment of the lid and base plate in the one-component system is lower than that for the two-component system. That is, because the one-component system does not have array components in the lid to be aligned with array locations on the base plate, alignment is not as stringent. However, alignment may still be important for imaging.

Furthermore, as described above, the lid of the chamber in the one-component system can be made of glass, plastic or metal. Again, the use of metal facilitates the maintenance of temperature as the metal is a fast and efficient heat conductor.

In addition, the system may comprise additional elements as well. These include a holder or holders for the probes or fiber optic bundles. Such holders are more fully described in U.S. Ser. No. 60/135,089, filed May 20, 1999, and Ser. No. 09/574,962 filed May 19, 2000, and PCT US00/13772 filed May 19, 2000. In addition, the system may include cells as described in U.S. Ser. Nos. 09/033,462 and 09/260,963 and PCT/US99/04473. In addition, the system may include fiducials as described in U.S. Ser. Nos. 60/119,323, and 09/500,555 and PCT/US00/03375, all of which are expressly incorporated herein by reference.

In a preferred embodiment, the methods and compositions of the invention comprise a robotic system. Systems can be directed to the use of 96 (or more) well microtiter plates, but as will be appreciated by those in the art, any number of different plates or configurations of arrays may be used. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of the plates containing the one or more arrays; automated lid handlers to remove and replace lids for wells on non-cross contamination plates; tip assemblies for sample distribution with disposable tips; washable tip assemblies for sample distribution; 96 well or other configuration loading blocks; cooled reagent racks; plate pipette positions (optionally cooled); stacking towers for plates and tips; and computer systems.

Fully robotic systems include automated liquid- and particle-handling, including high throughput pipetting to perform all steps of screening applications. This includes liquid, and particle manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid and particle transfers.

In a preferred embodiment, chemically derivatized particles, plates, tubes, magnetic particle, or other solid phase matrix with specificity to the ligand or variant proteins are used. The binding surfaces of plates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-assay location plates, multi-tubes, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of the heat exchangers such as controlled blocks or platforms to provide accurate temperature control of incubating samples from 4° C. to 100° C.

In a preferred embodiment, Interchangeable pipet heads (single or multi-channel) with single or multiple magnetic probes, affinity probes, or pipetters robotically manipulate the liquid and particles. Multi-well or multi-tube magnetic separators or platforms manipulate liquid and particles in single or multiple sample formats.

In some preferred embodiments, the instrumentation will include CCD cameras to capture and transform data and images into quantifiable formats; and a computer workstation. These will permit data analysis. CCD cameras used in the method of the invention will permit simultaneous detection of one or more subpopulations of beads. The CCD cameras used in detection can be coupled with additional optics devices including lenses, fiber optics, image intensifiers, and the like, for amplifying, focusing, reducing or expanding the images produced in the detection methods of the invention. One skilled in the art will be readily able to determine the detector and optics required according to the desired screening methods and the dimensions of the invention composite of arrays.

In other embodiments, the instrumentation will include confocal microscopes. Confocal microscopes used in the method of the invention will permit simultaneous imaging of one or more subpopulations of beads. The confocal microscope will typically be configured for receiving a composite array of the present invention which is formatted to the dimensions of a microscope slide.

Exemplary detection instruments useful with the composite array of the invention are well known in the art and include, for example, the GenePix 4000B Array Scanner from Axon Instruments, Inc., GSI Scanarray 3000 from GSI Luminomics, arrayWoRx Microarray Scanner from Applied Precision, and the like.

In one embodiment of the invention, the array composition will be attached via a liquid and/or vapor tight seal to a fluid flow device. Such a fluid flow device will permit sample, solvent, probes, rinsing solutions, reacting solutions, and the like, to flow over the discrete sites and the microspheres positioned thereon. Thus, a fluid flow device will be capable of carrying out functions such as those disclosed above with regard to the pneumatic device or robotic device, or other such devices known in the art. Fluid flow devices known in the art include flow cells such as those provided by manufacturers such as Mindrum Precision, Inc., Rancho Cucamonga, Calif.; and Upchurch Scientific, Oak Harbor, Wash.

In a preferred embodiment of the invention, the array composition of the invention is attached to a fluid flow device and positioned with respect to a detection instrument such as a confocal microscope or a CCD camera in such a way as to permit numerous iterations of sample loading, detection, rinsing, and the like, without requiring the array composition to be moved or manipulated in any manner beyond fluid flow through the fluid flow device.

The hardware used in the apparatus and detection methods of the invention preferably orients the invention composite arrays with respect to the detector optics or to the CCD camera or other optical detection device such that substantially all discrete sites (i.e., 80% or more, preferably 90% or more, more preferably 95% or more) of an array, and, in a preferred embodiment, all arrays (i.e., 80% or more, preferably 90% or more, more preferably 95% or more), can be accurately and simultaneously detected. The present invention provides a composite array, typically containing a rigid support, which composite array is sufficiently rigid to permit the various discrete sites on the composite array to be positioned for accurate, simultaneous measurement by, for example, all discrete sites being oriented at the same distance from the optics or detector.

Accordingly, detection methods which include the use of instruments such as CCD cameras and confocal microscopes will find increased efficacy when the substrate, such as an invention composite array, is planar and the detector is positioned substantially parallel to the substrate such that a plurality of signals from the discrete sites can be measured. Thus, the array composition of the present invention will be substantially planar and flat to within about 20 µm. As referred to herein, substantially planar means that about 80% of the discrete sites lie in the same plane, within a non-planarity tolerance of about 20 µm. Preferably, about 90% of the discrete sites will lie in the same plane, within the above tolerance; more preferably, about 95% of the discrete sites lie in the same plane; most preferably about 98% of the discrete sites lie in the same plane.

The above non-planarity tolerance will typically have a flatness or planarity to within about 20 µm. The flatness or planarity of the substrate can correspond to the flatness of the discrete sites within the active area of the detection device, or can alternatively correspond to the flatness or planarity of the discrete sites throughout the entire substrate. Flatness or planarity within a particular distance refers to the characteristic of a substrate in which discrete sites differ by no more than the specified distance along the dimension perpendicular to the plane of the substrate. For example, discrete sites that are flat or planar to within about 20 µm are the discrete sites which are sufficiently close to the plane of the substrate such that each discrete site is no more than 20 µm "higher" than another discrete site (where height is measured as a distance along the dimension perpendicular to the plane of the substrate). In one embodiment the discrete sites have a flatness or planarity such that they preferably lie within the depth of field of the detection device. Preferably, the non-planarity tolerance will be within about 10 µm. More preferably, the non-planarity tolerance will be within about 5 µm. Most preferably the non-planarity tolerance will be within about 1 µm.

In a preferred embodiment, the composite arrays of the invention utilize fiducials to allow comparison of sequential data images of the arrays. Such a fiducial can be a bead with a unique optical signature or other characteristic. Alternatively, the substrate or composite array may have other types of physical fiducials, such one or more defined edges that have characteristic optical properties that can be either spaced along the edge(s) or comprise the entire edge. Alternatively, the fiducials can be an inherent characteristic of the array; for example, small irregularities in the sites (features) of the array can be exploited to serve as fiducials, generating a "fiducial template". Other such fiducials and methods for using arrays comprising fiducials are taught in U.S. Ser. No. 09/500,555, which is herein incorporated by reference.

The flexible hardware and software allow instrument adaptability for multiple applications. The software program modules allow creation, modification, and running of methods. The system diagnostic modules allow instrument alignment, correct connections, and motor operations. The customized tools, labware, and liquid and particle transfer patterns allow different applications to be performed. The database allows method and parameter storage. Robotic and computer interfaces allow communication between instruments.

In a preferred embodiment, the robotic workstation includes one or more heating or cooling components. Depending on the reactions and reagents, either cooling or heating may be required, which can be done using any number of known heating and cooling systems, including Peltier systems.

In a preferred embodiment, the robotic apparatus includes a central processing unit which communicates with a memory and a set of input/output devices (e.g., keyboard, mouse, monitor, printer, etc.) through a bus. The general interaction between a central processing unit, a memory, input/output devices, and a bus is known in the art. Thus, a variety of different procedures, depending on the experiments to be run, are stored in the CPU memory.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type. By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers, Ind. is a helpful guide.

The beads need not be spherical; irregular particles may be used. In addition, the beads may be porous, thus increasing the surface area of the bead available for either bioactive agent attachment or IBL attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

In some embodiments, each microsphere comprises a bioactive agent, although as will be appreciated by those in the art, there may be some microspheres which do not contain a bioactive agent, depending on the synthetic methods. Alternatively, as described herein, in some embodiments it is desirable that a population of microspheres does not contain a bioactive agent. By "candidate bioactive agent" or "bioactive agent" or "chemical functionality" or "binding ligand" as used herein describes any molecule, e.g., protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 Daltons. Bioactive agents comprise functional groups necessary for structural interaction with proteins, particularly hydrogen bonding, and typically include at least an amine, carbonyl, hydroxyl or carboxyl group, and preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and peptides.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents is used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984); Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphosphoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowski, et al., *Angew. Chem. Intl. Ed. English*, 30:423 (1991); Letsinger, et al., *J. Am. Chem. Soc.*, 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

In a preferred embodiment, the bioactive agents are libraries of clonal nucleic acids, including DNA and RNA. In this embodiment, individual nucleic acids are prepared, generally using conventional methods (including, but not limited to, propagation in plasmid or phage vectors, amplification techniques including PCR, etc.). The nucleic acids are preferably arrayed in some format, such as a microtiter plate format, and beads added for attachment of the libraries.

Attachment of the clonal libraries (or any of the nucleic acids outlined herein) may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

In a preferred embodiment, affinity capture is used to attach the clonal nucleic acids to the beads. For example, cloned nucleic acids can be derivatized, for example with one member of a binding pair, and the beads derivatized with the other member of a binding pair. Suitable binding pairs are as described herein for IBL/DBL pairs. For example, the cloned nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can then be used to add the nucleic acid to the surface.

Preferred attachments are covalent, although even relatively weak interactions (i.e. non-covalent) can be sufficient to attach a nucleic acid to a surface, if there are multiple sites of attachment per nucleic acid. Thus, for example, electrostatic interactions can be used for attachment, for example by having beads carrying the opposite charge to the bioactive agent.

Similarly, affinity capture utilizing hybridization can be used to attach cloned nucleic acids to beads. For example, as is known in the art, polyA+RNA is routinely captured by hybridization to oligo-dT beads; this may include oligo-dT capture followed by a cross-linking step, such as psoralen crosslinking. If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

In general, special methods are required to decode clonal arrays, as is more fully outlined below.

As described above generally for proteins, nucleic acid bioactive agents may be naturally occurring nucleic acids, random nucleic acids, or "biased" random nucleic acids. For example, digests of prokaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., *Molecular Cloning: A Laboratory Manual*, 2d Edition, 1989, and *Short Protocols in Molecular Biology*, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

The target sequence may also be comprised of different target domains; for example, in "sandwich" type assays as outlined below, a first target domain of the sample target sequence may hybridize to a capture probe or a portion of capture extender probe, a second target domain may hybridize to a portion of an amplifier probe, a label probe, or a different capture or capture extender probe, etc. In addition, the target domains may be adjacent (i.e. contiguous) or separated. For example, when OLA techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. In addition, as will be appreciated by those in the art, the probes on the surface of the array (e.g. attached to the microspheres) may be attached in either orientation, either such that they have a free 3' end or a free 5' end; in some embodiments, the probes can be attached at one or more internal positions, or at both ends.

As outlined herein, the invention provides a number of different primers and probes. By "primer nucleic acid" herein is meant a probe nucleic acid that will hybridize to some portion, i.e. a domain, of the target sequence. The size of the primer nucleic acid may vary, as will be appreciated by those in the art, in general varying from 5 to 500 nucleotides in length, with primers of between 10 and 100 being preferred, between 15 and 50 being particularly preferred, and from 10 to 35 being especially preferred, depending on the use and amplification technique. In addition, the different amplification techniques may have further requirements of the primers, as is more fully described below.

In general, either direct or indirect detection of the target products can be done. "Direct" detection as used in this context, as for the other reactions outlined herein, requires the incorporation of a label, in this case a detectable label, preferably an optical label such as a fluorophore, into the target sequence, with detection proceeding as outlined below. In this embodiment, the label(s) may be incorporated in a variety of ways: (1) the primers comprise the label(s), for example attached to the base, a ribose, a phosphate, or to analogous structures in a nucleic acid analog; (2) modified nucleosides are used that are modified at either the base or the ribose (or to analogous structures in a nucleic acid analog) with the label(s); these label-modified nucleosides are then converted to the triphosphate form and are incorporated into a newly synthesized strand by a polymerase; (3) modified nucleotides are used that comprise a functional group that can be used to add a detectable label; (4) modified primers are used that comprise a functional group that can be used to add a detectable label or (5) a label probe that is directly labeled and hybridizes to a portion of the target sequence can be used. Any of these methods result in a newly synthesized strand or reaction product that comprises labels, that can be directly detected as outlined below.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as SBE, OLA, invasive cleavage reactions, etc; in addition, these techniques may be used with many of the other techniques described herein. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents.

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow good attachment, sufficient flexibility to allow good interaction with the target molecule, and to avoid undesirable binding reactions. In a preferred embodiment, the bioactive agents are synthesized directly on the beads. As is known in the art, many classes of chemical compounds are currently synthesized on solid supports, including beads, such as peptides, organic moieties, and nucleic acids.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, a-haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems*, 7(4):275-308 (1991), expressly incorporated herein). Proteinaceous candidate agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj. Chem.* 3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the candidate agents may be attached in a variety of ways, including those listed above. Preferably, the manner of attachment does not significantly alter the functionality of the candidate agent; that is, the candidate agent should be attached in such a flexible manner as to allow its interaction with a target. In addition, these types of chemical or biological functionalities may be used to attach arrays to assay locations, as is depicted in FIG. 1F, or individual sets of beads.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, Kcl). This is stirred on a stir bed for approximately 2 hours at room temperature. The microspheres are then rinsed with ultrapure water plus 0.01% tween 20 (surfactant)-0.02%, and rinsed again with a pH 7.7 PBS plus 0.01% tween 20. Finally, the enzyme is added to the solution, preferably after being prefiltered using a 0.45 mm Amicon micropure filter.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" as used herein with respect to IBL/DBL binding is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$-$10^{-6}$ M$^{-1}$, with less than about $10^{-5}$ to $10^{-9}$ M$^{-1}$ being preferred and less than about $10^{-7}$-$10^{-9}$ M$^{-1}$ being particularly preferred.

IBL-DBL binding pairs are known or can be readily found using known techniques. For example, when the IBL is a protein, the DBLs include proteins (particularly including antibodies or fragments thereof (FAbs, etc.) or small molecules, or vice versa (the IBL is an antibody and the DBL is a protein). Metal ion—metal ion ligands or chelators pairs are also useful. Antigen-antibody pairs, enzymes and substrates or inhibitors, other protein-protein interacting pairs, receptor-ligands, complementary nucleic acids (including nucleic acid molecules that form triple helices), and carbohydrates and their binding partners are also suitable binding pairs. Nucleic acid—nucleic acid binding proteins pairs are also useful, including single-stranded or double-stranded nucleic acid binding proteins, and small molecule nucleic acid binding agents. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

Alternatively, in a preferred embodiment, the IBL and the bioactive agent are the same moiety; thus, for example, as outlined herein, particularly when no optical signatures are used, the bioactive agent can serve as both the identifier and the agent. For example, in the case of nucleic acids, the bead-bound probe (which serves as the bioactive agent) can also bind decoder probes, to identify the sequence of the probe on the bead. Thus, in this embodiment, the DBLs bind to the bioactive agents. This is particularly useful as this embodiment can give information about the array or the assay in addition to decoding. For example, as is more fully described below, the use of the DBLs allows array calibration and assay development. This may be done even if the DBLs are not used as such; for example in non-random arrays, the use of these probe sets can allow array calibration and assay development even if decoding is not required.

In a preferred embodiment, the microspheres do not contain an optical signature. That is, as outlined in U.S. Ser. Nos. 08/818,199 and 09/151,877, previous work had each subpopulation of microspheres comprising a unique optical signature or optical tag that is used to identify the unique bioactive agent of that subpopulation of microspheres; that is, decoding utilizes optical properties of the beads such that a bead comprising the unique optical signature may be distinguished from beads at other locations with different optical signatures. Thus the previous work assigned each bioactive agent a unique optical signature such that any microspheres comprising that bioactive agent are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

In the present invention, "decoding" refers to identifying one or more bioactive ligands located in an invention array. Decoding can be carried out using any of a variety of methods, including using optical signatures, decoding binding ligands that are added during a decoding step, or a combination of these methods. The decoding binding ligands will bind either to a distinct identifier binding ligand partner that is placed on the beads, or to the bioactive agent itself, for example when the beads comprise single-stranded nucleic acids as the bioactive agents. The decoding binding ligands are either directly or indirectly labeled, and thus decoding can occur by detecting the presence of the label. By using pools of decoding binding ligands in a sequential fashion, it is possible to greatly minimize the number of required decoding steps.

Thus, the present invention need not rely solely on the use of optical properties to decode the arrays, although in some instances it may. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use in combination with optical signatures one beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants However, as is more fully discussed below, the size of the array may be further increased if another parameter is included such as concentration or intensity; thus for example, if two different concentrations of the IBL are used, then the array size increases as $3^{10}$. Thus, in this embodiment, each individual bioactive agent in the array is assigned a combination of IBLs, which can be added to the beads prior to the addition of the bioactive agent, after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labeled DBL allows the user to distinguish between the two beads.

Once the microspheres comprising the candidate agents and the unique IBLs are generated, they are added to the substrate to form an array. It should be noted that while most of the methods described herein add the beads to the substrate prior to the assay, the order of making, using and decoding the array can vary. For example, the array can be made, decoded, and then the assay done. Alternatively, the array can be made, used in an assay, and then decoded; this may find particular use when only a few beads need be decoded. Alternatively, the beads can be added to the assay mixture, i.e. the sample containing the target analytes, prior to the addition of the beads to the substrate; after addition and assay, the array may be decoded. This is particularly preferred when the sample comprising the beads is agitated or mixed; this can increase the amount of target analyte bound to the beads per unit time, and thus (in the case of nucleic acid assays) increase the hybridization kinetics. This may find particular use in cases where the concentration of target analyte in the sample is low; generally, for low concentrations, long binding times must be used.

In addition, adding the beads to the assay mixture can allow sorting or selection. For example, a large library of beads may be added to a sample, and only those beads that bind the sample may be added to the substrate. For example, if the target analyte is fluorescently labeled (either directly (for example by the incorporation of labels into nucleic acid amplification reactions) or indirectly (for example via the use of sandwich assays)), beads that exhibit fluorescence as a result of target analyte binding can be sorted via Fluorescence Activated Cell Sorting (FACS) and only these beads added to an array and subsequently decoded. Similarly, the sorting may be accomplished through affinity techniques; affinity columns comprising the target analytes can be made, and only those beads which bind are used on the array. Similarly, two bead systems can be used; for example, magnetic beads comprising the target analytes can be used to "pull out" those beads that will bind to the targets, followed by subsequent release of the magnetic beads (for example via temperature elevation) and addition to an array.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for association of the beads. This may be done in a variety of buffers, including aqueous and organic solvents, and mixtures. The solvent can evaporate, and excess beads removed.

In a preferred embodiment, when non-covalent methods are used to associate the beads to the array, a novel method of loading the beads onto the array is used. This method comprises exposing the array to a solution of particles (including microspheres and cells) and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the particles (beads, cells, etc.). The surface may comprise wells, as is described herein, or other types of sites on a patterned surface such that there is a differential affinity for the sites. This differential affinity results in a competitive process, such that particles that will associate more tightly are selected. Preferably, the entire surface to be "loaded" with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising samples, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stiffing or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to associate the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules.

Thus, after the array is made, it is "decoded" in order to identify the location of one or more of the bioactive agents, i.e. each subpopulation of beads, on the substrate surface. FIG. 11 depicts a flow chart exemplifying, but not limiting, the assays that can be performed with the arrays and hybridization chamber of the invention.

In a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags, or mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached bioactive agent may be done directly, for example using mass spectroscopy.

Alternatively, the identification may occur through the use of identifier moieties ("IMs"), which are similar to IBLs but need not necessarily bind to DBLs. That is, rather than elucidate the structure of the bioactive agent directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a non-fluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of association of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every bioactive agent is determined using decoder binding ligands (DBLs). As outlined above, DBLs are binding ligands that will either bind to identifier binding ligands, if present, or to the bioactive agents themselves, preferably when the bioactive agent is a nucleic acid or protein.

In a preferred embodiment, as outlined above, the DBL binds to the IBL.

In a preferred embodiment, the bioactive agents are single-stranded nucleic acids and the DBL is a substantially complementary single-stranded nucleic acid that binds (hybridizes) to the bioactive agent, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include luminescent labels. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs. Suitable labels include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, FITC, PE, cy3, cy5 and others described in the 6th Edition of the Molecular Probes Handbook by Richard P. Haugland, hereby expressly incorporated by reference.

In one embodiment, the label is a molecule whose color or luminescence properties change in the presence of the IBL, due to a change in the local environment. For example, the label may be: (1) a fluorescent pH indicator whose emission intensity changes with pH; (2) a fluorescent ion indicator, whose emission properties change with ion concentration; or (3) a fluorescent molecule such as an ethidium salt whose fluorescence intensity increases in hydrophobic environments.

A label can also include a semiconductor nanocrystal, also known as a quantum dot. Semiconductor nanocrystal compositions and applications are known in the art, as is demonstrated in the teachings of U.S. Pat. Nos. 5,571,018; 5,505,928; 5,262,357; 5,990,047; 6,207,392; and EP 0 990 903, each of which is incorporated by reference in their entirety. Quantum dot labels will find particularly preferred use for applications such as large-scale multiplexing, continued use of the label, broad wavelength irradiation, narrow wavelength detection, particle or high energy beam irradiation, distance-sensitive assays, and the like.

Accordingly, the identification of the location of the individual beads (or subpopulations of beads) is done using one or more decoding steps comprising a binding between the labeled DBL and either the IBL or the bioactive agent (i.e. a hybridization between the candidate probe and the decoder probe when the bioactive agent is a nucleic acid). After decoding, the DBLs can be removed and the array can be used; however, in some circumstances, for example when the DBL binds to an IBL and not to the bioactive agent, the removal of the DBL is not required (although it may be desirable in some circumstances). In addition, as outlined herein, decoding may be done either before the array is used in an assay, during the assay, or after the assay.

In one embodiment, a single decoding step is done. In this embodiment, each DBL is labeled with a unique label, such that the number of unique labels is equal to or greater than the number of bioactive agents (although in some cases, "reuse" of the unique labels can be done, as described herein; similarly, minor variants of candidate probes can share the same decoder, if the variants are encoded in another dimension, i.e. in the bead size or label). For each bioactive agent or IBL, a DBL is made that will specifically bind to it and contains a unique label, for example one or more fluorochromes. Thus, the identity of each DBL, both its composition (i.e. its sequence when it is a nucleic acid) and its label, is known. Then, by adding the DBLs to the array containing the bioactive agents under conditions which allow the formation of complexes (termed hybridization complexes when the components are nucleic acids) between the DBLs and either the bioactive agents or the IBLs, the location of each DBL can be elucidated. This allows the identification of the location of each bioactive agent; the random array has been decoded. The DBLs can then be removed, if necessary, and the target sample applied.

In a preferred embodiment, the number of unique labels is less than the number of unique bioactive agents, and thus a sequential series of decoding steps are used. To facilitate the discussion, this embodiment is explained for nucleic acids, although other types of bioactive agents and DBLs are useful as well. In this embodiment, decoder probes are divided into n sets for decoding. The number of sets corresponds to the number of unique tags. Each decoder probe is labeled in n separate reactions with n distinct tags. All the decoder probes share the same n tags. Each pool of decoders contains only one of the n tag versions of each decoder, and no two decoder probes have the same sequence of tags across all the pools. The number of pools required for this to be true is determined by the number of decoder probes and the n. Hybridization of each pool to the array generates a signal at every address comprising an IBL. The sequential hybridization of each pool in turn will generate a unique, sequence-specific code for each candidate probe. This identifies the candidate probe at each address in the array. For example, if four tags are used, then 4×n sequential hybridizations can ideally distinguish 4n sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

As will be appreciated by one of ordinary skill in the art, hybridization or incubation times vary. Generally, hybridization or incubation times last from seconds to minutes or up to hours or days or more. When the hybridization chamber as described herein is utilized, hybridization or incubation times can be increased relative to incubation times without the hybridization chamber.

An example is illustrative. Assuming an array of 16 probe nucleic acids (numbers 1-16), and four unique tags (four different fluors, for example; labels A-D). Decoder probes 1-16 are made that correspond to the probes on the beads. The first step is to label decoder probes 1-4 with tag A, decoder probes 5-8 with tag B, decoder probes 9-12 with tag C, and decoder probes 13-16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc. As will be appreciated by those in the art, the decoder probes can be made in any order and added in any order.

In one embodiment, the decoder probes are labeled in situ; that is, they need not be labeled prior to the decoding reaction. In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent or quantum dot. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead. The dyes may be chromophores or phosphors but are preferably fluorescent dyes or quantum dots, which due to their strong signals provide a good signal-to-noise ratio for decoding. Suitable dyes for use in the invention include those listed for labeling DBLs, above.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same labels (i.e. telephone numbers) of other subarrays, that are separated by virtue of the location of the subarray. Thus, for example, the same unique labels can be reused from bundle to bundle. Thus, the use of 50 unique labels in combination with 100 different subarrays can form an array of 5000 different bioactive agents. In this embodiment, it becomes important to be able to identify one bundle from another; in general, this is done either manually or through the use of marker beads; these can be beads containing unique tags for each subarray, or the use of the same marker bead in differing amounts, or the use of two or more marker beads in different ratios.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, generally through the use of DBLs. The second sublibrary is then added, and the location of each bioactive agent is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target analytes different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes or "families" of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

In a preferred embodiment, decoding of self-assembled random arrays is done on the bases of pH titration. In this embodiment, in addition to bioactive agents, the beads comprise optical signatures, wherein the optical signatures are generated by the use of pH-responsive dyes (sometimes referred to herein as "pH dyes") such as fluorophores. This embodiment is similar to that outlined in PCT US98/05025 and U.S. Ser. No. 09/151,877, both of which are expressly incorporated by reference, except that the dyes used in the present invention exhibits changes in fluorescence intensity (or other properties) when the solution pH is adjusted from below the pKa to above the pKa (or vice versa). In a preferred embodiment, a set of pH dyes is used, each with a different pKa, preferably separated by at least 0.5 pH units. Preferred embodiments utilize a pH dye set of pKa's of 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11, and 11.5. Each bead can contain any subset of the pH dyes, and in this way a unique code for the bioactive agent is generated. Thus, the decoding of an array is achieved by titrating the array from pH 1 to pH 13, and measuring the fluorescence signal from each bead as a function of solution pH.

In a preferred embodiment, there are additional ways to increase the number of unique or distinct tags. That is, the use of distinct attributes on each bead can be used to increase the number of codes. In addition, sequential decoding allows a reuse of codes in new ways. These attributes are independent of each other, thus allowing the number of codes to grow exponentially as a function of the number of decoding steps and the number of attributes (e.g. distinct codes). However, by increasing the amount of decoding information obtained in a single decoding step, the number of decoding steps is markedly reduced. Alternatively, the number of distinct codes is markedly increased. By increasing the number of attributes per decoding step, fewer decoding steps are required for a given number of codes. Thus, in a preferred embodiment, a variety of methods are used to generate a number of codes for use in the process of decoding the arrays, while minimizing the necessary decoding steps. For example, a variety of different coding strategies can be combined: thus, different "colors", combinations of colors ("hues"), different intensities of colors or hues or both, etc. can all be combined.

In a preferred embodiment DBLs rely on attaching or embedding a quantitative or discrete set of physical attributes to the bead, i.e. labeling the bead. Preferred physical attributes of a bead include but are not limited to: surface "smoothness" or "roughness", color (Fluorescent and otherwise), color intensity, size, detectable chemical moieties, chemical reactivity, magnetization, pH sensitivity, energy transfer efficiency between dyes present, hydrophobicity, hydrophilicity, absorptivity, charge, pH sensitivity, etc.

A bead decoding scheme includes assigning/imbuing a single quantifiable attribute to each bead type wherein each bead type differs in the quantifiable value of that attribute. For instance, one can attach a given number of fluorophores to a bead and quantitate the number of attached fluorophores in the decoding process; however, in practice, attaching a "given amount" of an attribute to a bead and accurately measuring the attribute may be problematic. In general, the goal is to reduce the coefficient of variation (CV). By coefficient of variation is meant the variability in labeling a bead in successive labelings. This CV can be determined by labeling beads with a defined given number of label (fluorophore, for example) in multiple tests and measuring the resulting signal emitted by the bead. A large CV limits the number of useable and resolvable "levels" for any given attribute.

A more robust decoding scheme employs ratiometric rather than absolute measurements for segmenting a quantitative attribute into codes. By ratiometric decoding is meant labeling a bead with a ratio of labels (i.e. 1:10, 1:1, and 10:1). In theory any number of ratios can be used so long as the difference in signals between the ratios is detectable. This process produced smaller CVs and allowing more attribute segmentation within a given dynamic range. Thus, in a preferred embodiment, the use of ratiometric decoding reduces the coefficient of variability.

In addition, as will be appreciated by those in the art, ratiometric decoding can be accomplished in a different way. In this embodiment, rather than add a given number of DBLs with a first dye (or dye combination) intensity in the first decoding reaction and a second number with a second dye intensity in the sequential second decoding reaction, this ratiometric analysis may be done by using a ratio of labeled:unlabelled DBLs. That is, given a set saturating concentration of decoding beads, for example 100,000 DBLs/reaction, the first intensity decoding step may be done by adding 100,000 labeled DBLs and the second step can be done by adding 10,000 labeled DBLs and 90,000 unlabeled DBLs. Equilibrium dictates that the second step will give one tenth the signal intensity.

Because of the spread in values of a quantitatively measured attribute value, the number of distinct codes is practically limited to less than a dozen or so codes. However, by serially "painting" (i.e. temporarily attaching an attribute level to a bead) and "stripping" (removing the attribute level) a bead with different attribute values, the number of possible codes grows exponentially with the number of serial stages in the decoding process.

An example is illustrative. For instance, nine different bead types and three distinguishable attribute distributions (Table 1). "Painting" (labeling) the beads with different attribute values in a combinatorially distinct pattern in the two different stages, generates a unique code for each bead type, i.e. nine distinct codes are generated. Thus, in a preferred embodiment beads are labeled with different attributes in a combinatorially distinct pattern in a plurality of stages. This generates unique codes for each bead type. Examples of different attributes are described above. Labeling of beads with different attributes is performed by methods known in the art.

TABLE 1

Serial decode generates unique codes using a small number of attribute levels

| stage 1 Bead Type | stage 2 attribute value | attribute value | Code |
|---|---|---|---|
| 1 | L | L | (L, L) |
| 2 | L | M | (L, M) |
| 3 | L | H | (L, H) |
| 4 | M | L | (M, L) |

TABLE 1-continued

Serial decode generates unique codes using a small number of attribute levels

| stage 1 Bead Type | stage 2 attribute value | attribute value | Code |
|---|---|---|---|
| 5 | M | M | (M, M) |
| 6 | M | H | (M, H) |
| 7 | H | L | (H, L) |
| 8 | H | M | (H, M) |
| 9 | H | H | (H, H) |

Number of unique codes = Number of attributes * Number of stages

Fluorescent colors are a particularly convenient attribute to use in a decoding scheme. Fluorescent colors can be attached to any agent that recognizes an IBL to form a labeled DBL. The discussion is directed to oligonucleotides (including nucleic acid analogs) as the DBLs. A fluorescently labeled oligonucleotide is a particularly useful DBL since it can specifically and reversibly "paint" (label) any desired subset of beads with a particular color simply by the process of hybridization and dehybridization (i.e. to the DBL with a complementary sequence). Moreover, fluorescence is easily imaged and quantitated using standard optical hardware and software. In order to "paint" a given bead type with a particular color, the bead type must be labeled with a unique hybridizable DNA sequence (IBL) and the decoding solution must contain the color-labeled complement of that sequence.

One consideration in implementing a decoding scheme is to minimize the number of images collected. In a color-based scheme, the number of images collected is the product of the number of colors and the number of stages. The number of images can be reduced by "painting" a bead with multiple colors for each given stage. By assigning multiple colors to a bead, the number of effective codes is increased. As an example, in a 24 bit three color scheme (e.g. red, green, blue) coloring process used by computers, a total of 256*256*256=16.7 million different "hues" can be generated from just three colors (red, green, blue).

Thus, in a preferred embodiment DBLs are labeled with a combination of colored fluorophores. As such, this method finds use in increasing the number of available codes for labeling DBLs using only a handful of different dyes (colors). Increasing the number of codes available at each decoding step will greatly decrease the number of decoding steps required in a given decoding process.

In one embodiment a population of oligonucleotides encoding a single DBL is labeled with a defined ratio of colors such that each bead to which the DBL binds is identified based on a characteristic "hue" formulated from the combination of the colored fluorophores. In a preferred embodiment two distinct colors are used. In a preferred embodiment, three or more distinct dyes (colors) are available for use. In this instance the number of differentiable codes generated by labeling a population of oligonucleotides encoding a single DBL with any given color is three. However by allowing combinations of colors and color levels in the labeling, many more codes are generated.

For decoding by hybridization, a preferred number of distinguishable color shades is from 2 to 2000; a more preferred number of distinguishable color shades is from 2 to 200 and a most preferred number of distinguishable color shades is from 2 to 20. Utilizing three different color shades (intensities) and three colors, the number of different hues will be $3^4=81$. Combining a hue with sequential decoding allows a virtually limitless number of codes to be generated.

As previously described, the DBL can be any agent that binds to the IBL. In a preferred embodiment, a single DBL is labeled with a pre-determined ratio of colors. This ratio is varied for each DBL thus allowing for a unique "hue" for each DBL labeled as such. Following treatment of the beads with the DBL, the bead is analyzed to determine the "hue" associated with each bead, thereby identifying the bead with its associated bioactive agent.

For instance, with four primary colors and two intensity levels (color is present or absent), fifteen different hues/stage are possible. If four dyes and three different intensity levels are used (absent, half-present, fully present), then 73 different hues/stage are possible. In this case, acquisition of only 4 color images is sufficient to obtain information on 73 different coding hues.

In a preferred embodiment, the present invention provides array compositions comprising a first substrate with a surface comprising discrete sites. Preferred embodiments utilize a population of microspheres distributed on the sites, and the population comprises at least a first and a second subpopulation. Each subpopulation comprises a bioactive agent, and, in addition, at least one optical dye with a given pKa. The pKas of the different optical dyes are different.

In a preferred embodiment, when for example the array comprises cloned nucleic acids, there are several methods that can be used to decode the arrays. In a preferred embodiment, when some sequence information about the cloned nucleic acids is known, specific decoding probes can be made as is generally outlined herein.

In a preferred embodiment, "random" decoding probes can be made. By sequential hybridizations or the use of multiple labels, as is outlined above, a unique hybridization pattern can be generated for each sensor element. This allows all the beads representing a given clone to be identified as belonging to the same group. In general, this is done by using random or partially degenerate decoding probes, that bind in a sequence-dependent but not highly sequence-specific manner. The process can be repeated a number of times, each time using a different labeling entity, to generate a different pattern of signals based on quasi-specific interactions. In this way, a unique optical signature is eventually built up for each sensor element. By applying pattern recognition or clustering algorithms to the optical signatures, the beads can be grouped into sets that share the same signature (i.e. carry the same probes).

In order to identify the actual sequence of the clone itself, additional procedures are required; for example, direct sequencing can be done. By using an ordered array containing the clones, such as a spotted cDNA array, a "key" can be generated that links a hybridization pattern to a specific clone whose position in the set is known. In this way the clone can be recovered and further characterized.

Alternatively, clone arrays can be decoded using binary decoding with vector tags. For example, partially randomized oligos are cloned into a nucleic acid vector (e.g. plasmid, phage, etc.). Each oligonucleotide sequence consists of a subset of a limited set of sequences. For example, if the limits set comprises 10 sequences, each oligonucleotide may have some subset (or all of the 10) sequences. Thus each of the 10 sequences can be present or absent in the oligonucleotide. Therefore, there are $2^{10}$ or 1,024 possible combinations. The sequences may overlap, and minor variants can also be represented (e.g. A, C, T and G substitutions) to increase the number of possible combinations. A nucleic acid library is cloned into a vector containing the random code sequences. Alternatively, other methods such as PCR can be used to add the tags. In this way it is possible to use a small number of oligo decoding probes to decode an array of clones.

In a preferred embodiment, discriminant analysis and cluster algorithms and computer apparatus are used to analyze the shown in FIG. 3, the location of the centroids and their distances from one another are indicated in Table 2.

TABLE 2

| dye/channel | Centroid position | | | | Distance between centroids | | | |
|---|---|---|---|---|---|---|---|---|
| | Blue | Green | Yellow | Red | Bod-493 | Bod-R6G | Bod-564 | Bod-TXR |
| Bod-493 | 0.63 | 0.22 | 0.11 | 0.03 | 0.00 | | | |
| Bod-R6G | 0.03 | 0.51 | 0.37 | 0.09 | 0.72 | 0.00 | | |
| Bod-564 | 0.06 | 0.04 | 0.57 | 0.32 | 0.81 | 0.55 | 0.00 | |
| Bod-TXR | 0.09 | 0.05 | 0.04 | 0.82 | 0.99 | 0.93 | 0.73 | 0.00 | decoding data from the arrays of the invention. The potentially large number of codes utilized in the invention, coupled with the use of different intensities and "hues" of fluorophores in multi-step decoding processes requires good classification of the data. The data, particularly intensity data, is acquired in a multi-step process during which beads are reversibly labeled (for example by hybridizing dye-labeled complementary decoding oligonucleotides to the IBL probes on the beads, or the formation of binding ligand pairs for non-nucleic acid IBL-DBL pairs) with different colors or mixtures of colors ("hues") at each stage. The challenge is to accurately classify a bead as to which color with which it was painted at each step. The more closely related the labels are to one another (as determined by the optical imaging system), the more difficult the classification.

The proximity of the dyes as seen by the imaging system is determined by the spectral properties of the decoding dyes and the spectral channel separation of the imaging system. Better color separation is achieved by employing fluorescent dyes with narrow emission spectra, and by employing an optical system with narrow band pass excitation and emission filters which are designed to excite the dye "on peak" and measure its emission "on peak". The process of optically imaging the dyes on the beads is similar to the human vision process in which our brain sees color by measuring the ratio of excitation in the three different cone types within our eye. However, with an optical imaging system, the number of practical color channels is much greater than the three present in the human eye. CCD based imaging systems can "see" color from 350 nm up to 850 nm whereas the cones in the eye are tuned to the visible spectrum from 500-600 nm.

The problem of decoding bead arrays is essentially a discriminant analysis classification problem. Thus, in a preferred embodiment, an analysis of variance in hyperspectral alpha space is performed on a known set of bead colors or hues. The center of the bead clusters in alpha space are termed the centroids of the clusters, and the scatter of the points within a cluster determines the spread of the cluster. A robust classification scheme requires that the distance between the centroids of the different bead classes (hues) is much greater than the spread of any cluster class. Moreover, the location of the centroids should remain invariant from fiber to fiber and from experiment to experiment.

Thus, in a preferred embodiment, a hue "zone" is defined as a region in alpha space surrounding the hue centroid and extending out to the spread radius of the cluster. Given a reference set of hue centroids and spread radii, as determined empirically, the classification of a new set of data can be accomplished by asking whether a given bead point falls closest to or within the "zone" of a hue cluster. This is accomplished by calculating the Mahalanobis distance (in this case, it is simply a Euclidean distance metric) of the bead point from the centroids of the different hue classes. For the data For classifying the different beads into a particular hue class, a Euclidean distance cutoff of 0.3 was chosen. The closest two centroids, the Bod-R6G and Bod-564 (dist=0.55), have a slight overlap in their decoding zones when using a Euclidean or Mahalanobis distance of 0.3. An improvement in classification can be achieved by decreasing this distance, and by weighting the different coordinate axes appropriately.

Accordingly, the present invention provides computer methods for analyzing and classifying the color of a bead. The classification of the color of the bead is done by viewing the bead in hyperspectral "alpha" space (a1=I1/SIi, a2=I2/SIi, a3=I3/SIi, etc.) in which each coordinate axis represents the fraction of the bead intensity within a given imaging channel. For instance, if four imaging channels are used to image the beads, the color or hue of a bead can be represented by a point in 3-D alpha space (the fourth dimension is not necessary since Sai=1). Given a set of different primary dyes by which to label the beads, the number of hues that can be generated from these dyes is unlimited since the dyes can be combined in varying ratios and in varying combinatorial patterns. The number of practical hues is experimentally determined by the separation of the different hue clusters in hyperspectral alpha space.

FIG. 3 shows a hyperspectral alpha plot of beads labeled with four different hues imaged in four separate imaging channels. Note that the beads form four distinct clusters. The fact that these four clusters are well separated allows a robust decode classification scheme to be implemented.

In a preferred embodiment, a quality control analysis of the decoding process is done. This is achieved by performing a cluster analysis of alpha space for each decoding stage. The number of clusters determined will be fixed by the expected number of hues. The positions of the cluster centroids will be monitored and any deviations from the expected position will be noted.

Thus the invention provides an apparatus for decoding the arrays of the invention. In addition to the compositions outlined herein, the apparatus includes a central processing unit which communicates with a memory and a set of input/output devices (e.g., keyboard, mouse, monitor, printer, etc.) through a bus. The general interaction between a central processing unit, a memory, input/output devices, and a bus is known in the art. One aspect of the present invention is directed toward the hyperspectral "alpha" space classification system stored in the memory.

The classification system program includes a data acquisition module that receives data from the optical reader or confocal microscope (or other imaging system). In general, the classification program also includes an analysis module, that can analyze the variance in hyperspectral alpha space, calculate the centroids of the clusters, calculate the scatter of the cluster (the spread) and define the hue zone and distance cutoff. In general, the analysis module will further determine whether a data point falls within the hue zone by calculating the Mahalanobis distance.

Finally, the analysis module will analyze the different sequential decoding information to finally assign a bioactive agent to a bead location.

In this way, sequential decoding steps are run, with each step utilizing the discriminant analysis calculations to assign each bead in the array to a hue cluster at each step. The buildup of the sequential decoding information allows the correlation of the location of a bead and the chemistry contained on it.

Once made, the compositions of the invention find use in a number of applications. In a preferred embodiment, the compositions are used to probe a sample solution for the presence or absence of a target analyte, including the quantitation of the amount of target analyte present. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (e.g. a drug candidate) is sought.

Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, a-fetoprotein, thyroxin, thyroid stimulating hormone (TSH), antithrombin, antibodies to pharmaceuticals (including antiepileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus*; *Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis*, *M. leprae*; *Clostridium*, e.g. *C. botulinum*, *C. tetani*, *C. difficile*, *C. perfringens*; *Cornyebacterium*, e.g. *C. diphtheriae*; *Streptococcus*, *S. pyogenes*, *S. pneumoniae*; *Staphylococcus*, e.g. *S. aureus*; *Haemophilus*, e.g. *H. influenzae*; *Neisseria*, e.g. *N. meningitidis*, *N. gonorrhoeae*; *Yersinia*, e.g. *G. lamblia Y. pestis*, *Pseudomonas*, e.g. *P. aeruginosa*, *P. putida*; *Chlamydia*, e.g. *C. trachomatis*; *Bordetella*, e.g. *B. pertussis*; *Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-a and TGF-b), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progesterone, testosterone; and (4) other proteins (including a-fetoprotein, carcinoembryonic antigen CEA.

In addition, any of the biomolecules for which antibodies may be detected may be detected directly as well; that is, detection of virus or bacterial cells, therapeutic and abused drugs, etc., may be done directly.

In a preferred embodiment, the target analyte is a nucleic acid. These assays find use in a wide variety of applications, as is generally outlined in U.S. Ser. Nos. 60/160,027; 60/161, 148; 09/425,633; 60/160,917 and 60/244,119, all of which are expressly incorporated herein by reference.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" as used herein with respect to bioactive agent/ligand binding is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$ to $10^{-6}$ $M^{-1}$, with less than about $10^{-5}$ to $10^{-9}$ $M^{-1}$ being preferred and less than about $10^{-7}$ to $10^{-9}$ $M^{-1}$ being particularly preferred.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc., which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

Once made, the compositions of the invention find use in a number of applications. In a preferred embodiment, the compositions are used to probe a sample solution for the presence or absence of a target sequence, including the quantitation of the amount of target sequence present.

The compositions of the invention are useful for any of a variety of nucleic acid assays including SNP identification, sequencing, amplification, genotyping, nucleic acid quantitation, and the like; methods for carrying out such assays are taught in U.S. Ser. No. 60/244,119, which is herein incorporated by reference.

In more specific embodiments, the teachings herein are useful for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art; in particular, single base extension (SBE) and pyrosequencing techniques are particularly useful with the compositions of the invention.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different fluorophor, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimized for every probe simultaneously. Therefore, a competitive assay system can be used to help compensate for non-optimal conditions for mismatch discrimination.

In a preferred embodiment, dideoxynucleotide chain-termination sequencing is done using the compositions of the invention. In this embodiment, a DNA polymerase is used to extend a primer using fluorescently labeled ddNTPs. The 3' end of the primer is located adjacent to the SNP site. In this way, the single base extension is complementary to the sequence at the SNP site. By using four different fluorophors, one for each base, the sequence of the SNP can be deduced by comparing the four base-specific signals. This may be done in several ways. In a first embodiment, the capture probe can be extended; in this approach, the probe must either be synthesized 5'-3' on the bead, or attached at the 5' end, to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased stringency which is particularly helpful for the analysis of complex samples.

Accordingly, in one embodiment the invention provides a method of preparing a universal array as described above. In addition, the invention provides a method of linking a variety of molecules to a universal bead. That is, the method includes attaching an adapter sequence to a target analyte to form an adapter/target analyte complex. This complex is then immobilized to a bead to which an adapter has been attached. In a preferred embodiment the adapter is a hairpin adapter. A particular advantage of the present invention is that universal adapter beads can be prepared in bulk. That is, there is no need to prepare different adapter beads because the adapters are the same. In addition, because the association of the bead adapters and adapter/target analyte complexes is based on affinity, the immobilized complexes are more resistant to the presence of impurities.

Accordingly, the present invention includes a method of affinity purifying a target analyte. The method includes attaching an adapter to the target analyte to form an adapter/target analyte complex and isolating the complex by hybridization to a bead adapter. In a preferred embodiment the adapter is a hairpin adapter.

In an additional embodiment the invention provides a method of regulating the packing density of target analytes linked to the bead surface. The method includes adding adapters that are free from a target analyte (dummy adapter) but hybridize with the bead-based adapter. This dummy adapter will hybridize with a fraction of the bead-based adapters, depending on the concentration. As such, the dummy adapters serve as spacers.

In an additional embodiment the invention provides a method of selecting full length sequences. That is the invention provides a method of isolating target sequences from their 5' terminus. As is known in the art, obtaining the 5' end of a target sequence can at times be challenging. However, the present invention allows for the selection of full length sequences. When the adapter is designed such that the 3' terminus is recessed for ligation, the hybridization and ligation reaction can be used to select for full-length products from a 3' to 5' chemical synthesis of an oligonucleotide. Only full-length, 5' phosphorylated products will be able to link covalently to the adapter. If the reaction is performed under conditions where non-covalently linked molecules are transiently stable, full-length molecules are selected from the mixture of other sequences. That is, following hybridization and ligation of the full-length target sequence, the non-covalently bound products are removed. The remaining sequences are full-length sequences. In effect, a solid-phase affinity-based purification of full-length products is performed.

In one embodiment the invention provides for specific array formats. That is, arrays are designed with an eye to monitoring a particular factor in a target sample. Such factors include the presence of microorganisms in a sample, the presence of recombinant molecules in a sample, the presence of contamination in a sample, and the like. In particular, the invention provides an array for the detection of genetically modified foods. That is, nucleic acid arrays are constructed to detect a subset or all known genetically modified variants of crop or livestock species including commercially important species such as, corn or cattle. The arrays would contain elements or combinations of elements that would uniquely identify each GM (genetically modified) strain of the organism in question. Such elements might identify any of the following signatures for a given strain: the presence of transgenes, the absence of deleted genes, the boundaries created by such deletions or insertions, and the like. DNA is extracted from food products or other samples of the tested organisms, and hybridized to the array. The combination of hybridizing signals or absence of hybridizing signals identifies the GMOs (genetically modified organisms) present in the sample.

A GMO array allows food manufacturers to examine the quality control of each lot of incoming ingredients or outgoing products to ensure that only the intended strains are included. Likewise, industrial farms would be able to use such arrays to check their seed lots, and manufacturers of GMO-free products would use such arrays to validate that their product is truly GMO free.

In an additional embodiment the array can be designed to detect reporter genes in a target species. As is known in the art, reporter genes are genes whose products generate easily detected signals such as luminescence, fluorescence, or measurable biochemical products. They are used for a wide range of applications in biotechnology, including monitoring the acquisition of transgenic DNA, measuring promoter activity, and many others. Because they are useful for so many purposes, a small number of reporter genes have been inserted into a variety of species, including those that are widely studied, such as bacteria, fungi, plants, invertebrates and vertebrates, including cultured cells of humans.

Developing a microarray for a new organism or even a new subset of genes from the same organism presents the need to rapidly develop reliable protocols for sample preparation and array validation. Organisms and even different tissues in an organism differ in their biochemical composition and rates of degradation of RNA, all of which make necessary developing and validating new procedures for sample preparation and storage for each new biological system under investigation. Accordingly, the invention provides a method of calibrating sensor arrays.

In one embodiment the invention provides a method of generating standardized array elements for the detection of reporter genes. The method includes developing a collection of sensors, each specifically detecting a particular reporter gene or reporter gene product. The sensors are characterized to determine the sensitivity and dynamic range with which they detect their targets. Concurrent with or prior to the development of an array for a new organism or a new tissue type, the standard sensors is used to establish sample preparation procedures. The samples would then be hybridized to the array and the quality of the specimen preparations could be monitored by the detection of the reporter gene transcript.

In one embodiment when a new array is made, a replicate batch of the reporter gene sensors is cosynthesized with the sensors in the new array. In testing the array, both the newly synthesized sensors and the well-characterized standard sensors used in the previous pilot experiments are loaded onto the array with the organism-specific sensors. If a hybridization failure occurs with the new array, the behavior of the two groups of sensors would facilitate the tracing of the problem. If all the sensors fail, it suggests a problem in the sample. If the cosynthesized sensors fail but the original sensors work, it suggests a problem in the synthesis of the new array. Because reporter gene activity is by definition easily monitored, one obtains an independent measurement of the reporter gene's activity in the source tissue; in this way it is possible to eliminate variation in expression levels as a reason for failing to obtain or detect hybridization signals in the array.

All references cited herein are incorporated by reference in their entireties.

What is claimed is:

1. A method of forming a fluidics chamber, said method comprising the steps of:
    a) randomly distributing a population of microspheres to an array substrate having a surface comprising a plurality of depressions, wherein said population of microspheres comprises at least a first and second subpopulation of microspheres comprising a target nucleic acid, said first subpopulation having a target nucleic acid that is different from the target nucleic acid of the second subpopulation;
    b) providing a population of blank microspheres and randomly distributing said population of blank microspheres to the array substrate, wherein the microspheres are present in a ratio of microspheres comprising a target nucleic acid to $n^2$ blank microspheres, wherein n is the number of blank microspheres separating the microspheres comprising target nucleic acid;
    c) applying a force to said substrate, thereby moving microspheres to the bottoms of the depressions;
    d) mating the substrate to a lid, said lid having at least one inlet port and one outlet port; and
    e) clamping said lid to said substrate a sealant being disposed between said lid and said substrate, thereby forming a fluidics chamber.

2. The method of claim 1, wherein depressions of said substrate have a diameter that is dimensioned to accommodate not more than a single microsphere comprising a target nucleic acid.

3. The method of claim 1, wherein the target nucleic acid comprises a genome fragment or a copy of a genome fragment.

4. The method of claim 1, wherein a target nucleic acid is attached to a microsphere.

5. The method of claim 4, wherein the attachment is mediated using biotin.

6. The method of claim 1, further comprising attaching a first fluidics line to the inlet port and attaching a second fluidics line to the outlet port.

7. The method of claim 6 further comprising applying fluid through said fluidics lines.

8. The method of claim 1, wherein the depressions are regularly spaced.

9. The method of claim 1, wherein the space between depressions is greater than 5 μm.

10. The method of claim 1, wherein the space between depressions is less than 15 μm.

11. The method of claim 1, wherein said force is a magnetic force.

12. The method of claim 1, wherein said substrate is optically coupled to a CCD camera.

13. The method of claim 1, wherein said clamping step is automated.

14. The method of claim 1, wherein said clamping step comprises engaging a hook and latch mechanism.

15. The method of claim 1, wherein said clamping step comprises engaging a rotating stud and receptacle mechanism.

16. The method of claim 1, further comprising aligning said substrate with said lid using an alignment moiety.

17. The method of claim 16, wherein said alignment moiety comprises a notch.

18. The method of claim 1, wherein said sealant is selected from the group consisting of rubber and silicon.

19. The method of claim 18, wherein said sealant comprises a gasket.

20. The method of claim 1, wherein said inlet port and said outlet port are each fitted with a seal.

21. The method of claim 20, wherein said seal comprises an o-ring.

22. The method of claim 1, wherein the array substrate comprises a fiber optic bundle.

23. The method of claim 1, wherein applying force to said substrate results in filling depressions at an average density per depression of not more than one microsphere comprising a target nucleic acid.

24. The method of claim 1, wherein said surface is substantially planar.

25. The method of claim 1, wherein the microspheres are present in a ratio of at least 1:100 microspheres comprising a target nucleic acid to blank microspheres.

26. The method of claim 25, wherein the microspheres are present in a ratio of at least 10:1 microspheres comprising a target nucleic acid to blank microspheres.

27. The method of claim 22, wherein the fiber optic bundle is embedded within the substrate.

28. The method of claim 1, wherein the substrate is opaque.

29. The method of claim 1, further comprising combining the subpopulations of microspheres comprising nucleic acids with the population of blank microspheres prior to randomly distributing the combined population to the array substrate.

* * * * *